United States Patent
Pearson et al.

(10) Patent No.: US 6,462,023 B1
(45) Date of Patent: *Oct. 8, 2002

(54) CYTOSTATIC AGENTS

(75) Inventors: Lindsey Ann Pearson; Andrew Paul Ayscough; Philip Huxley; Alan Drummond, all of Oxford (GB)

(73) Assignee: British Biotech Pharmaceuticals, Ltd., Oxford (GB)

(*) Notice: Subject to any disclaimer, the term of this patent is extended or adjusted under 35 U.S.C. 154(b) by 0 days.

This patent is subject to a terminal disclaimer.

(21) Appl. No.: 09/100,539

(22) Filed: Jun. 19, 1998

Related U.S. Application Data

(63) Continuation-in-part of application No. 08/925,584, filed on Sep. 8, 1997, now Pat. No. 6,169,075, which is a continuation-in-part of application No. PCT/GB98/00754, filed on Mar. 12, 1988.

(30) Foreign Application Priority Data

Sep. 10, 1996 (GB) .............................. 9618899
Jun. 24, 1997 (GB) .............................. 9713202

(51) Int. Cl.$^7$ ................................ C07K 5/06
(52) U.S. Cl. ...................... 514/19; 560/312; 562/445; 514/506
(58) Field of Search .................. 514/19, 506; 562/445; 560/312

(56) References Cited

U.S. PATENT DOCUMENTS

| | | | |
|---|---|---|---|
| 4,599,361 A | 7/1986 | Dickens et al. | |
| 5,183,900 A | 2/1993 | Galardy et al. | 548/495 |
| 5,256,657 A | 10/1993 | Singh et al. | 514/228.2 |
| 5,270,326 A | 12/1993 | Galardy et al. | 514/323 |
| 5,872,152 A | 2/1999 | Brown et al. | 514/575 |

FOREIGN PATENT DOCUMENTS

| | | |
|---|---|---|
| EP | 231 081 | 8/1987 |
| EP | 236 872 | 9/1987 |
| EP | 274 453 | 7/1988 |
| EP | 489 577 | 6/1992 |
| EP | 489 579 | 6/1992 |
| EP | 497 192 | 8/1992 |
| EP | 574 758 | 12/1993 |
| EP | 575 844 | 12/1993 |
| WO | WO 90/05716 | 5/1990 |
| WO | WO 90/05719 | 5/1990 |
| WO | WO 91/02716 | 3/1991 |
| WO | WO 92/09563 | 6/1992 |
| WO | WO 92/13831 | 8/1992 |
| WO | WO 92/17460 | 10/1992 |
| WO | WO 92/21360 | 12/1992 |
| WO | WO 92/22523 | 12/1992 |
| WO | WO 93/09090 | 5/1993 |
| WO | WO 93/09097 | 5/1993 |
| WO | WO 93/14112 | 7/1993 |
| WO | WO 93/24449 | 9/1993 |
| WO | WO 93/20047 | 10/1993 |
| WO | WO 93/24475 | 12/1993 |
| WO | WO 94/02446 | 2/1994 |
| WO | WO 94/02447 | 2/1994 |
| WO | WO 94/21612 | 9/1994 |
| WO | WO 94/21625 | 9/1994 |
| WO | WO 94/24140 | 10/1994 |
| WO | WO 94/25434 | 11/1994 |
| WO | WO 94/25435 | 11/1994 |
| WO | WO 95/04033 | 2/1995 |
| WO | WO 95/04715 | 2/1995 |
| WO | WO 95/04735 | 2/1995 |
| WO | WO 95/06031 | 3/1995 |
| WO | WO 95/09841 | 4/1995 |
| WO | WO 95/12603 | 5/1995 |
| WO | WO 95/19956 | 7/1995 |
| WO | WO 95/19957 | 7/1995 |
| WO | WO 95/19961 | 7/1995 |
| WO | WO 95/19965 | 7/1995 |
| WO | WO 95/22966 | 8/1995 |
| WO | WO 95/23790 | 9/1995 |
| WO | WO 97/18183 | 5/1997 |
| WO | WO 97/19053 | 5/1997 |
| WO | 98/11063 | * 3/1998 |

OTHER PUBLICATIONS

Cawston et al. "Mammalian Collagenases," *Meth. In Enzymol.*, 711–722 (1981).

Cawston et al., "A Rapid and Reproducible Assay for Collagenase Using [1–$^{14}$C]Acetylated Collagen," *Ana. Biochem.*, 99:340–345 (1979).

Cawston et al., "Purification of Rabbit Bone Inhibitor of Collagenase," *Biochem. J.* 195:159–165 (1981).

Devlin et al., "Studies Concerning the Antibiotic Actinonin, Part III. Synthesis of Structural Analogues of Actinonin by the Anhydride–Imide Method," *J.C.S. Perkin Trans I*, 830–841 (1975).

Sellers, "Separation in Latent Forms of Distinct Enzymes that When Activated Degrade Collagen, Gelatin and Proteoglycans," *Biochem. J.* 171:493–496 (1978).

(List continued on next page.)

*Primary Examiner*—Christopher S. F. Low
*Assistant Examiner*—David Lukton
(74) *Attorney, Agent, or Firm*—Eugene C. Rzucidlo; Greenberg Traurig LLP

(57) ABSTRACT

The present invention provide compounds exemplified by 2(R or S)-[2R-(S-Hydroxy-hydroxycarbamoyl-methyl)-4-methyl-pentanoylamine]-2-phenyl-ethanoic acid cyclopentyl ester; 2(R or S)-(3S-Hydroxycarbamoyl-2R-isobutyl-hex-5-enoylamino)-2-phenylethanoic acid isopropyl ester; 2(R or S)-[2R-(S-Hydroxycarbamoyi-methoxy-methyl)-4-methyl-pentanoylamino]-3-phenylethanoic acid cyclopentyl ester; 2(R or S)-(3S-Hydroxycarbamoyl-2R-isobutyl-hex-5-enoylamino)-2-(4-methoxyphenyl)ethanoic acid cyclopentyl ester; 2(R or S)-(3S-Hydroxycarbamoyl-2R-isobutyl-hex-5-enoylamino)-2-(thien-2-yl)ethanoic acid cyclopentyl ester; and 2(R or S)-(3S-Hydroxycarbamoyl-2R-isobutyl-hex-5-enoylamino)-2-(thien-3-yl)ethanoic acid cyclopentyl ester are cytostatic agents. Methods of treating proliferative cell growth disorders as well a methods of inhibiting hyperproliferative cells are also disclosed.

32 Claims, No Drawings

OTHER PUBLICATIONS

Woessner, "Matrix Metalloproteinases and their Inhibitors In Connecitve Tissue Remodeling," *FASEB J.*, 5:2145–2154 (1991).

Bourdel, "New Hydroxamate Inhibitors of Neurotensin–degrading Enzymes," *Int. J. Peptide Protein Res.*, 48:148–155 (1996).

Broughton, "Studies Concerning the Antibiotic Actinonin. Part VIII. Structure–Activity Relationships in the Actinonin Series," *J. Chem. Soc.*, 9:857–860 (1975).

Cawston, et al., "Mammalian Collagenases," *Meth. In Enzymol.*, 80:711–722 (1981).

Cawston, et al., "A Rapid and Reproducible Assay for Collagenase Using [1–$^{14}$C]Acetylated Collagen," *Ana. Biochem.*, 99:340–345 (1979).

Cawston, et al., "Purification of Rabbit Bone Inhibitor of Collagenase," *Biochem. J.*, 195:159–165 (1981).

Devlin, et al., "Studies Concerning the Antibiotic Actinonin. Part III. Synthesis of Structural Analogues of Actinonin by the Anhydride–Imide Method," *J.C.S. Perkin Trans I*, 830–841 (1975).

Sellers, "Separation in Latent Forms of Distinct Enzymes that When Activated Degrade Collagen, Gelatin and Proteoglycans," *Biochem. J*, 171:493–496 (1978).

Woessner, "Matrix Metalloproteinases and their Inhibitors in Connective Tissue Remodeling," *FASEB J.*, 5:2145–2154 (1991).

* cited by examiner

CYTOSTATIC AGENTS

The present application is a continuation-in-part of pending U.S. Ser. No. 08/925,584, filed Sep. 8, 1997, now U.S. Pat. No. 6,169,075 and PCT application PCT/GB98/00754, filed Mar. 12, 1988.

The invention relates to therapeutically active esters and thioesters, processes for preparing them, pharmaceutical compositions containing the same, as well as their uses, i.e., treating proliferative cell growth disorders and inhibiting cells characterized by with hyper-proliferative cell growth. A particular use contemplated by the compounds of the invention lies is the in vitro and in vivo inhibition of growth and proliferation of hyper-proliferative tumourgenic cells such as melanoma and/or lymphoma cells.

BACKGROUND OF THE INVENTION

Anti-Proliferative Agents

There is a need in cancer therapy for therapeutic compounds, which are inhibitors of the proliferation of tumour cells. One compound, which is known to have such activity, is 5-fluorouracil (5-FU).

Anti-Metastatic and Anti-Invasive Agents

Compounds which have the property of inhibiting the action of the metalloproteinase enzymes involved in connective tissue breakdown and remodeling, such as fibroblast collagenase (Type 1), PMN-collagenase, 72 kDa-gelatinase, 92 kDa-gelatinase, stromelysin, stromelysin-2 and PUMP-1 (known as "matrix metalloproteinases", and herein referred to as MMPs) have been proposed and are being tested in the clinic for the treatment of solid tumours.

Cancer cells are particularly adept at utilizing MMPs to achieve rapid remodeling of the extracellular matrix, thereby providing space for tumour expansion and permitting metastasis. Accordingly, MMP inhibitors should minimize these processes and thus slow or prevent cancer progression.

A known class of MMP inhibitors having a hydroxamic acid group as the zinc-binding group may be presented by the structural formula (IA)

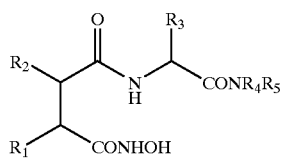

(IA)

in which the groups $R_1$ to $R_5$ are variable in accordance with the specific prior art disclosures of such compounds. Examples of patent publications disclosing MMP inhibitors of formula (IA) are:

| U.S. Pat. No. 4599361 | (Searle) | WO 93/24475 | (Celltech) |
|---|---|---|---|
| EP-A-2321081 | (ICI) | EP-A-0574758 | (Roche) |
| EP-A-0236872 | (Roche) | EP-A-0575844 | (Roche) |
| EP-A-0274453 | (Bellon) | WO 94/02446 | (British Biotech) |
| WO 90/05716 | (British Biotech) | WO 94/02447 | (British Biotech) |
| WO 90/05719 | (British Biotech) | WO 94/21612 | (Otsuka) |
| WO 91/02716 | (British Biotech) | WO 94/21625 | (British Biotech) |
| WO 92/09563 | (Glycomed) | WO 94/24140 | (British Biotech) |
| U.S. Pat. No. 5183900 | (Glycomed) | WO 94/25434 | (Celltech) |
| U.S. Pat. No. 5270326 | (Glycomed) | WO 94/25435 | (Celltech) |
| WO 92/17460 | (SB) | WO 95/04033 | (Celltech) |
| EP-A-0489577 | (Celltech) | WO 95/04735 | (Syntex) |
| EP-A-0489579 | (Celltech) | WO 95/04715 | (Kanebo) |
| EP-A-0497192 | (Roche) | WO 95/06031 | (Immunex) |
| U.S. Pat. No. 5256657 | (Sterling) | WO 95/09841 | (British Biotech) |
| WO 92/13831 | (British Biotech) | WO 95/12603 | (Syntex) |
| WO 92/22523 | (Research Corp) | WO 95/19956 | (British Biotech) |
| WO 93/09090 | (Yamanouchi) | WO 95/19957 | (British Biotech) |

| WO 93/09097 | (Sankyo) | WO 95/19961 | (British Biotech) |
|---|---|---|---|
| WO 93/20047 | (British Biotech) | WO 95/19965 | (Glycomed) |
| WO 93/24449 | (Celltech) | WO 95/22966 | (Sanofi Winthrop) |
| WO 95/23790 | (SB) | | |

It is noteworthy that all of the compounds embraced by formula (1A) generally act extracellulary and are not shown to enter the target cells i.e., tumourgenic cells, in order to perform their respective functions.

International patent application No. PCT/GB97/02398 describes, inter alia, a method for inhibiting growth and proliferation of tumour cells in mammals. The method comprises administering to a mammal in need thereof an inhibiting amount of a compound of general formula (1) or a pharmaceutically acceptable salt hydrate or solvate thereof sufficient to inhibit proliferation the tumour cells:

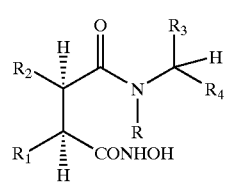

(1)

wherein
R is hydrogen or $(C_1-C_6)$alkyl;
$R_1$ is hydrogen;
$(C_2-C_6)$alkyl;
$(C_2-C_6)$alkenyl;
phenyl or substituted phenyl;
phenyl $(C_1-C_6)$alkyl or substituted phenyl$(C_1-C_6)$alkyl;
phenyl $(C_2-C_6)$alkenyl or substituted phenyl$(C_2-C_6)$alkenyl
heterocyclyl or substituted heterocyclyl;
heterocyclyl$(C_1-C_6)$alkyl or substituted heterocyclyl $(C_1-C_6)$alkyl;
a group $BSO_nA-$ wherein n is 0, 1 or 2 and B is hydrogen or a $(C_1-C_6)$alkyl, phenyl, substituted phenyl, heterocyclyl substituted heterocyclyl, $(C_1-C_6)$acyl, phenacyl or substituted phenacyl group, and A represents $(C_1-C_6)$alkylene;
hydroxy or $(C_1-C_6)$alkoxy;
amino, protected amino, acylamino, $(C_1-C_6)$alkylamino or di-$(C_1-C_6)$alkylamino; mercapto or $(C_1-C_6)$alkylthio;
amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, mercapto$(C_1-C_6)$alkyl or carboxy$(C_1-C_6)$alkyl wherein the amino-, hydroxy-, mercapto- or carboxyl-group are optionally protected or the carboxyl- group amidated;

lower alkyl substituted by carbamoyl, mono(lower alkyl) carbamoyl, di(lower alkyl)carbamoyl, di(lower alkyl) amino, or carboxy-lower alkanoylamino; or a cycloalkyl, cycloalkenyl or non-aromatic heterocyclic ring containing up to 3 heteroatoms, any of which may be (i) substituted by one or more substituents selected from $C_1$–$C_6$ alkyl, $C_2$–$C_6$ alkenyl, halo, cyano (—CN), —$CO_2H$, —$CO_2R_1$ $CONH_2$, —CONHR, —CON(R)$_2$, —OH, —OR, oxo—, —SH, —SR, —NHCOR, and —$NHCO_2R$ wherein R is $C_1$–$C_6$ alkyl or benzyl and/or (ii) fused to a cycloalkyl or heterocyclic ring;

$R_2$ is a $C_1$–$C_{12}$ alkyl,
$C_1$–$C_{12}$ alkenyl,
$C_1$–$C_{12}$ alkynyl,
phenyl($C_1$–$C_6$ alkyl)-,
heteroaryl($C_1$–$C_6$ alkyl)-,
phenyl($C_1$–$C_6$ alkenyl)-,
heteroaryl($C_2$–$C_6$ alkenyl)-,
phenyl($C_2$–$C_6$)alkynyl-,
heteroaryl($C_2$–$C_6$ alkynyl)-,
cycloalkyl($C_1$–$C_6$ alkyl)-,
cycloalkyl($C_2$–$C_6$ alkenyl)-,
cycloalkyl($C_2$–$C_6$ alkynyl)-,
cycloalkenyl($C_1$–$C_6$ alkyl)-,
cycloalkenyl($C_2$–$C_6$ alkenyl)-,
cycloalkenyl($C_2$–$C_6$ alkynyl)-,
phenyl($C_1$–$C_6$ alkyl)O($C_1$–$C_6$ alkyl)-, or
heteroaryl($C_1$–$C_6$ alkyl)O($C_1$–$C_6$ alkyl)- group,
any one of which may be optionally substituted by
$C_1$–$C_6$ alkyl,
$C_1$–$C_6$ alkoxy,
halo,
cyano (—CN),
phenyl, or
phenyl substituted by
$C_1$–$C_6$ alkyl,
$C_1$–$C_6$ alkoxy.
halo, or
cyano (—CN);

$R_3$ is the characterizing group of a natural or non-natural a amino acid in which any functional groups may be protected; and $R_4$ is an ester or thioester group, or a pharmaceutically acceptable salt, hydrate or solvate thereof.

Objects and Summary of the Invention

An object of the invention resides in providing anti-proliferative ester and thioester's which inhibit proliferation of rapidly dividing cells that generally attend proliferative cell growth disorders. Exemplary of such disorders are lymphoma, leukemia, myeloma, adenocarcinoma, carcinoma, mesothelioma, teratocarcinoma, choriocarcinoma, small cell carcinoma, large cell carcinoma, melanoma, retinoblastoma, fibrosarcoma, leiomyosarcoma or endothelioma cells.

The ester and thioester compounds in question have certain structural similarities to known MMP inhibitors of general formula (IA) above disclosed in the foregoing patent publications. However, instead of the amide group —$CONR_4R_5$, of formula (IA), they have an ester or thioester group. Despite the similarity of structure, it has been shown that compounds of the invention, which have little or no MMP inhibitory activity, are nonetheless potent inhibitors of such cell proliferation, implying a novel mechanism is at work. This anti-proliferation property suggests a utility for the compounds of the present invention in the treatment of cancers. That the compounds of the invention i.e., esters and thioesters maybe used to inhibit growth and proliferation of cells with hyper-proliferative cell growth is neither disclosed nor taught by the prior art.

Although the patent publications listed above predominantly disclose MMP inhibiting compounds of formula (IA), i.e., having an amide group —$CONR_4R_5$, a few (WO 92/09563, U.S. Pat. No. 5,183,900, U.S. Pat. No. 5,270,326, EP-A-0489577, EP-A-0489579, WO 93/09097, WO 93/24449, WO 94/25434, WO 94/25435, WO 95/04033, WO 95/19965, and WO 95/22966) include within their generic disclosure compounds having a carboxylate ester group in place of the amide group. The carboxylate ester compounds with which this invention is concerned thus represent a selection of a notional subclass from the compounds proposed in the art as MMP inhibitors, for a specific and previously unrecognized pharmaceutical utility.

WO 95/04033 discloses $N^4$-hydroxy-$N^1$-(1-(S)-methoxycarbonyl-2,2-dimethylpropyl)-2-(R)-(4-chlorophenylpropyl) succinamide as an intermediate for the preparation of the corresponding methylamide MMP inhibitor.

Likewise, *Int. J. Pept. Protein Res.* (1996), 48(2), 148–155 discloses the compound:

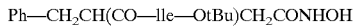

Ph—$CH_2CH(CO$—Ile—$OtBu)CH_2CONHOH$

The above compound is suggested as an intermediate in the preparation of compounds, which are inhibitors of neurotensin-degrading enzymes. However, those two appear to be the only specific known carboxylate ester compounds of the kind with which this invention is concerned. Neither of the above references specifically suggest the compounds of the present invention or their specific use for inhibiting proliferative cell growth disorders, which are normally attended by hyper-proliferative cell growth.

An alternative embodiment of the invention contemplates an in vivo method for inhibiting growth and proliferation of target cells characterized by hyper-proliferative cell growth. The method comprises administering to a subject in need thereof an inhibiting amount of at least one of the compounds of the invention or a pharmaceutically or veterinarily acceptable sale, hydrate or solvate thereof, in combination with a pharmaceutically or veterinarily acceptable carrier or diluent, sufficient to inhibit proliferation of the target cells.

A still further embodiment is directed to an in vitro method of inhibiting growth and proliferation of cells characterized by hyper-proliferative cell growth, comprising contacting the cells with a growth inhibiting amount of at least one compound of the invention or an acceptable salt, hydrate or solvate thereof.

Another embodiment provides a method for preventing or reducing the onset of a proliferative cell growth disorder in a subject, comprising administering to the subject a therapeutically effective amount of an least one compound of the invention or a pharmaceutically or veterinarily acceptable salt, hydrate or solvate thereof, in combination with a pharmaceutically or veterinarily acceptable carrier or diluent, sufficient to prevent or reduce onset of the disorder.

A still further embodiment of the invention is directed to a method of treating a subject suffering from a proliferative cell growth disorder characterized by hyper-proliferative cell growth. The method comprises administering to the subject a therapeutically effective amount of at least one compound of the invention or a pharmaceutically or veterinarily acceptable salt, hydrate or solvate thereof, in combination with a pharmaceutically or veterinarily acceptable carrier or diluent, sufficient to treat the subject.

A still further embodiment is directed to a pharmaceutical composition useful for treating a proliferative cell growth disorder, comprising a therapeutically effective amount of at least one of the compounds of the invention in combination with a pharmaceutically or a veterinarily acceptable carrier or diluent.

Another embodiment of the invention embraces an anti-proliferation composition comprising an effective amount of at least one of the compounds of the invention or a pharmaceutically or veterinarily acceptable salt, hydrate or solvate thereof, in combination with a pharmaceutically or veterinarily acceptable carrier or diluent.

A process for manufacturing the above compounds and various compositions embraced by the invention is also a subject of the invention.

A final embodiment of the invention provides for a method for the ex-vivo treatment of a proliferative cell growth disorder characterized by hyper-proliferative cell growth. The method provides for extracting a biological sample suspected of containing cells exhibiting hyper-proliferative cell growth from a subject suspected of suffering from a proliferative cell growth disorder, contacting ex-vivo the biological sample with an effective amount of at least one of the compounds of the present invention or a pharmaceutically or veterinarily acceptable salt, hydrate or solvate thereof, sufficient to inhibit cell proliferation of the cells in the biological sample, followed by introducing the treated sample into the subject.

The above and other objects, features and advantages of the present invention will become apparent from the description and examples that follow, it being recognized that the examples in no way limit the scope of the invention claimed.

DETAILED DESCRIPTION OF THE PREFERRED EMBODIMENTS

In its broadest aspect, the present invention provides a method for inhibiting proliferation of tumour cells in mammals, comprising administering to the mammal suffering such proliferation an amount of a compound of general formula (IB) or a pharmaceutically acceptable salt hydrate or solvate thereof sufficient to inhibit such proliferation:

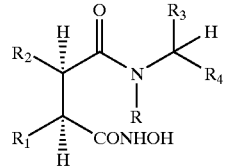

(I)

wherein
R is hydrogen or $(C_1-C_6)$alkyl;
$R_1$ is hydrogen;
$(C_1-C_6)$alkyl;
$(C_2-C_6)$alkenyl;
phenyl or substituted phenyl;
phenyl $(C_1-C_6)$alkyl or substituted phenyl$(C_1-C_6)$alkyl;
phenyl $(C_2-C_6)$alkenyl or substituted phenyl$(C_2-C_6)$alkenyl heterocyclyl or substituted heterocyclyl;
heterocyclyl$(C_1-C_6)$alkyl or substituted heterocyclyl $(C_1-C_6)$alkyl;

a group $BSO_nA-$ wherein n is 0, 1 or 2 and B is hydrogen or a $(C_1-C_6)$ alkyl, phenyl, substituted phenyl, heterocyclyl substituted heterocyclyl, $(C_1-C_6)$acyl, phenacyl or substituted phenacyl group, and A represents $(C_1-C_6)$alkylene;
hydroxy or$(C_1-C_6)$alkoxy;
amino, protected amino, acylamino, $(C_1-C_6)$alkylamino or di-$(C_1-C_6)$alkylamino;
mercapto or $(C_1-C_6)$alkylthio;
amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, mercapto$(C_1-C_6)$alkyl or carboxy$(C_1-C_6)$alkyl wherein the amino-, hydroxy-, mercapto- or carboxyl- group are optionally protected or the carboxyl- group amidated;
lower alkyl substituted by carbamoyl, mono(lower alkyl) carbamoyl, di(lower alkyl)carbamoyl, di(lower alkyl) amino, or carboxy-lower alkanoylamino; or a cycloalkyl, cycloalkenyl or non-aromatic heterocyclic ring containing up to 3 heteroatoms, any of which may be (i) substituted by one or more substituents selected from $C_1-C_6$ alkyl, $C_2-C_6$ alkenyl, halo, cyano (—CN), —$CO_2H$, —$CO_2R$, $CONH_2$, —CONHR, —CON$(R)_2$, —OH, —OR, oxo—, —SH, —SR, —NHCOR, and —$NHCO_2R$ wherein R is $C_1-C_6$ alkyl or benzyl and/or (ii) fused to a cycloalkyl or heterocyclic ring;
$R_2$ is a $C_1-C_{12}$alkyl,
$C_2-C_{12}$alkenyl,
$C_2-C_{12}$alkenyl,
phenyl$(C_1-C_6$alkyl)-,
heteroaryi$(C_1-C_6$alkyl)-,
phenyl$(C_2-C_6$alkenyl)-,
heteroaryl$(C_2-C_6$alkenyl)-,
phenyl$(C_2-C_6$alkynyl)-,
heteroaryl$(C_2-C_6$alkynyly,
cycloalkyl$(C_1-C_6$alkyl)-,
cycloalkyl$(C_2-C_6$alkenyl)-,
cycloalkyl$(C_2-C_6$alkynyl)-,
cycloalkenyl$(C_1-C_6$alkyl)-,
cycloalkenyl$(C_2-C_6$alkenyl)-,
cycloalkenyl$(C_2-C_6$alkynyly,
phenyl$(C_1-C_6$alkyl)O$(C_1-C_6$alkyl)-, or
heteroaryl$(C_1-C_6$ alkyl)O$(C_1-C_6$alkyl)- group,
any one of which may be optionally substituted by
$C_1-C_6$ alkyl,
$C_1-C_6$ alkoxy,
halo,
cyano (—CN),
phenyl, or
phenyl substituted by
$C_1-C_6$ alkyl,
$C_1-C_6$ alkoxy,
or cyano (—CN);
$R_3$ is the characterizing group of a natural or non-natural α amino acid in which any functional groups may be protected; and
$R_4$ is an ester or thioester group, or a pharmaceutically acceptable salt, hydrate or solvate thereof.

In another broad aspect of the invention, there is provided the use of a compound of formula (I) as defined in the immediately preceding paragraph, in the preparation of a pharmaceutical composition for inhibiting proliferation of tumour cells in mammals.

The present invention also provides novel compounds of general formula (I) above wherein R, $R_1$, $R_2$, $R_3$ and $R_4$ are as defined above with reference to formula (I), and pharmaceutically acceptable salts, hydrates or solvates thereof, PROVIDED THAT:

(i) when R and $R_1$, are hydrogen, $R_2$ is 4-chlorophenylpropyl, and $R_3$ is tert-butyl, then $R_4$ is not a methyl carboxylate ester group; and (ii) when R and $R_4$, are hydrogen, $R_2$ is phenylmethyl, and $R_3$ is 1-methylprop-1-yl, then R4 is not a tert-butyl carboxylate ester group.

One particular sub-group of the novel esters and thioesters of the invention consists of compounds of formula (I) above, wherein:

R, $R_1$, and $R_4$ are as defined above with reference to formula (1)

$R_2$ is $C_1-C_{12}$ alkyl, $C_2-C_{12}$alkenyl, $C_2-C_{12}$ alkynyl, biphenyl($C_1-C_6$alkyl)-, phenyl[heteroaryl($C_1-C_6$ alkyl)-, heteroarylphenyl ($C_1-C_6$ alkyl)-, biphenyl ($C_2-C_6$alkenyl)-, phenylheteroaryl ($C_2-C_6$alkenyl)-, heteroarylphenyl ($C_2-C_6$ alkenyl)-, phenyl($C_2-C_6$ alkynyl)-, heteroaryl($C_2-C_6$alkynyl)-, biphenyl($C_2-C_6$alkynyl)-, phenylheteroaryl ($C_2-C_6$alkynyl)-, heteroarylphenyl ($C_2-C_6$ alkynyl)-, phenyl($C_1-C_6$ alkyl)O($C_1-C_6$ alkyl)-, or heteroaryi ($C_1-C_6$ alkyl)O($C_1-C_6$ alkyl)-, any one of which may be optionally substituted on a ring carbon atom by $C_1-C_6$ alkyl, $C_1-C_6$ alkoxy, halo, or cyano (—CN); and $R_3$ is $C_1-C_6$alkyl, optionally substituted benzyl, optionally substituted phenyl, optionally substituted heteroaryl; or the characterizing group of a natural a amino acid, in which any functional group may be protected, any amino group may be acylated and any carboxyl group present may be amidated; or a heterocyclic ($C_1-C_6$)alkyl group, optionally substituted in the heterocyclic ring;

and pharmaceutically acceptable salts, hydrates or solvates thereof.

As used herein the term "($C_1-C_6$)alkyl" or "lower alkyl" means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

The term ($C_2-C_6$) "alkenyl" means a straight or branched chain alkenyl moiety having from 2 to 6 carbon atoms having at least one double bond of either E or Z stereochemistry where applicable. This term would include, for example, vinyl, allyl, 1- and 2-butenyl and 2-methyl-2-propenyl.

The term "$C_2-C_6$ alkynyl" refers to straight chain or branched chain hydrocarbon groups having from two to six carbon atoms and having in addition one triple bond. This term would include for example, ethynyl,- 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

The term "cycloalkyl" means a saturated alicyclic moiety having from 3–8 carbon atoms and includes, for example, cyclohexyl, cyclooctyl, cycloheptyl, cyclopentyl, cyclobutyl and cyclopropyl.

The term "cycloalkenyl" means an unsaturated alicyclic moiety having from 4–8 carbon atoms and includes, for example, cyclohexenyl, cyclooctenyll, cycloheptenyl, cyclopentenyl, and cyclobutenyl. In the case of cycloalkenyl rings of from 5–8 carbon atoms, the ring may contain more than one double bond.

The term "aryl" means an unsaturated aromatic carbocyclic group which is monocyclic (eg phenyl) or polycyclic (eg naphthyl).

The unqualified term "heterocyclyl" or "heterocyclic" means (i) a 5–7 membered heterocyclic ring containing one or more heteroatoms selected from S, N and O, and optionally fused to a benzene ring, including for example, pyrrolyl, furyl, thienyl, piperidinyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido, 1,2-dimethyl-3, 5-dioxo-1,2, 4-triazolidin-4-yl, 3,4, 4-trimethyl-2, 5-dioxo-1-imidazolidinyl, 2-methyl-3, 5-dioxo-1,2, 4-oxadiazol-4-yl, 3 methyl-2,4, 5-trioxo-1-imidazolidinyl,2, 5-dioxo-3-phenyl-1-imidazolidinyl, 2-oxo-1-pyrrolidinyl, 2, 5-dioxo-1-pyrrolidinyl or 2, 6-dioxopipeddinyl, or (ii) a napththalimido (i.e. 1, 3-dihydro-1, 3-dioxo-2H-benz[f] isoindol-2-yl), 1, 3-dihydro-1-oxo-2H-benz[f]isoindol-2-yl, 1, 3-dihydro-1, 3-dioxo-2H-pyrrolo[3, 4-b]quinolin-2-yl, or 2, 3-dihydro-1, 3-dioxo-1 H-benz[d,e]isoquinolin-2-yl group.

The term "heteroaryl" means a 5–7 membered substituted or unsubstituted aromatic heterocycle containing one or more heteroatoms. Illustrative of such rings are thienyl, furyl, pyrrolyl, imidazolyl, thiazolyl, pyrazolyl, isoxazolyl, isothiazolyl, thizolyl, thiadiazolyl, oxadiazolyl, pyridinyl, pyridazinyl, pyrimidinyl, pyrazinyl and triazinyl.

The term "ester" or "esterified carboxyl group" means a group $R_9O(C=O)$—in which $R_9$ is the group characterizing the ester, notionally derived from the alcohol $R_5$,OH.

The term "thioester" means a group $R_9S(C=O)$- or $R_9S(C=S)$- or $R_9(C=S)$-in which R is the group characterizing the thioester, notionally derived from the alcohol $R_9OH$ or the thioalcohol $R_9SH$.

Unless otherwise specified in the context in which it occurs, the term "substituted" as applied to any moiety herein means substituted with up to four substituents, each of which independently may be ($C_1-C_6$)alkyl, ($C_1-C_6$) alkoxy, hydroxy, mercapto, ($C_1-C_6$)alkylthio, amino, halo (including fluoro, chloro, bromo and iodo), nitro, trifluoromethyl, —COOH, —CONH$_2$, —CN, —COOR$^A$, —CONHR$^A$ or —CONHR$^A$R$^A$ wherein R$^A$ is a ($C_1-C_6$) alkyl group or the residue of a natural alpha-amino acid.

The term "side chain of a natural or non-natural alpha-amino acid" means the group $R^1$ in a natural or non-natural amino acid of formula $NH_2$—$CH(R^1)$—COOH.

Examples of side chains of natural alpha amino acids include those of alanine, arginine, asparagine, aspartic acid, cysteine, cystine, glutamic acid, histidine, 5 hydroxylysine, 4-hydroxyproline, isoleucine, leucine, lysine, methionine, phenylalanine, proline, serine, threonine, tryptophan, tyrosine, valine, a-aminoadipic acid, α-amino-n-butyric acid, 3,4-dihydroxyphenylalanine, homoserine, αmethylserine, ornithine, pipecolic acid, and thyroxine.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When $R_3$ in the compounds of the invention is one of those side chains, the functional substituents may optionally be protected.

The term "protected" when used in relation to a functional substituent in a side chain of a natural alpha-amino acid means a derivative of such a substituent, which is substantially non-functional. For example, carboxyl groups may be esterified (for example as a $C_1$–$C_6$ alkyl ester), amino groups may be converted to amides (for example as a $NHCOC_1$–$C_6$ alkyl amide) or carbamates (for example as an NHC(=O)O $C_1$–$C_6$ alkyl or $NHC(=O)OCH_2Ph$ carbamate), hydroxyl groups may be converted to ethers (for example an O $C_1$–$C_6$, alkyl or a $O(C_1$–$C_6$alkyl)phenyl ether) or esters (for example a OC(=O) $C_1$–$C_6$ alkyl ester) and thiol groups may be converted to thioethers (for example a tert-butyl or benzyl thioether) or thioesters (for example a SC(=O) $C_1$–$C_6$ alkyl thioester).

Examples of side chains of non-natural alpha amino acids include those referred to below in the discussion of suitable $R_3$ groups for use in compounds of the present invention.

The term "proliferative cell growth disorder" is a disorder that is characterized by hyper-proliferative cell growth in that such target cells exhibit a growth pattern that is hyper-proliferative (rapidly dividing cells).

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centers in the compounds according to the invention because of the presence of asymmetric carbon atoms. The presence of several asymmetric carbon atoms gives rise to a number of diastereomers with R or S sterochemistry at each chiral center. In the compounds of the invention, the C atom carrying the hydroxamic acid and R, groups is predominantly in the S configuration, the C atom carrying the $R_2$ group is predominantly in the R configuration, and the C atom carrying the $R_3$ and $R_4$ groups is in either the R or S configuration, with the predominantly S configuration presently preferred.

As previously stated, the compound with which the present invention is concerned are principally distinguished from the compounds disclosed in the prior patent publications listed above by the ester or thioester group $R_4$. Accordingly the groups R, $R_1$, $R_1$, $R_2$, and $R_3$, may include those which have been disclosed in the corresponding positions of compounds disclosed in any of those prior art patent publications listed above. Without limiting the generality of the foregoing, examples of substituents; R, $R_1$, $R_1$, $R_2$, and $R_3$ are given below:

The group $R_1$ $R_1$ may be, for example, hydrogen, methyl, ethyl, n-propyl, n-butyl, isobutyl, hydroxyl, methoxy, allyl, phenylpropyl, phenylprop-2-enyl, thienylsulphanylmethyl, thienylsulphinylmethyl, or thienylsulphonylmethyl; or $C_1$–$C_4$ alkyl, eg. methyl, ethyl n-propyl or n-butyl, substituted by a phthalimido, 1,2-dimethyl-3,5-dioxo-1,2,4-triazolidin-4-yl, 3-methyl-2,5-dioxo-1 imidazolidinyl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, 5,5-dimethyl-2,4-dioxo-3-oxazolidinyl, hexahydro-1,3 dioxopyrazolol[1,2,a][1,2,4]-triazol-2-yl, or a naphththalimido (ie. 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo 1H-benz[d,e]isoquinolin-2-yl group; or cyclohexyl, cyclooctyl, cycloheptyl, cyclopentyl, cyclobutyl, cyclopropyl, tetrahydro-pyra nyl or morpholinyl.

Presently preferred $R_1$ groups include n-propyl, allyl, methoxy and thienylsulfanylmethyl.

The group $R_2$ $R_2$ may for example be $C_1$–$C_6$alkyl, $C_3$–$C_6$ alkenyl or $C_3$–$C_6$ alkynyl; phenyl ($C_1$–$C_6$ alkyl)-, phenyl($C_3$–$C_6$ alkenyl)- or phenyl ($C_3$–$C_6$alkynyl)- optionally substituted in the phenyl ring;

heteroaryl($C_1$–$C_6$alkyl)-, heteroaryl($C_3$–$C_6$ alkenyl)- or heteroaryl($C_1$–$C_6$ alkynyl)- optionally substituted in the heteroaryl ring;

4-phenylphenyl($C_1$–$C_6$ alkyl)-, 4-phenylphenyl ($C_3$–$C_6$alkenyl)-, 4-phenylphenyl($C_3$–$C_6$alkynyl)-, 4-heteroarylphenyl($C_1$–$C_6$ alkyl)-, 4-heteroarylphenyl ($C_3$–$C_6$ alkenyl)-, 4-heteroarylphenyl($C_3$–$C_6$alkynyl)-, optionally substituted in the terminal phenyl or heteroaryl ring;

phenoxy ($C_1$–$C_6$ alkyl)- or heteroaryloxy($C_1$–$C_6$ alkyl)- optionally substituted in the phenyl or heteroaryl ring;

Specific examples of such groups include methyl, ethyl, n- and iso-propyl, n-, iso and tert-butyl, n-pentyl, n-hexyl, n-heptyl, n-nonyl, n-decyl, prop-2-yn-1-yl, 3-phenylprop-2-yn-1-yl, 3(2-chlorophenyl)prop-2-yn-1-yl, phenylpropyl, 4-chlorophenylpropyl, 4-methylphenylpropyl, 4-methoxyphenylpropyl, phenoxybutyl, 3-(4-pyridylphenyl)propyl-, 3-(4-(4-pyridyl)phenyl)prop-2-yn-1-yl, 3-(4-phenylphenyl)propyl-, 3-(4-phenyl)phenyl)prop-2-yn-1-yl and 3-[(4-chlorophenyl)phenyl]propyl-.

Presently preferred $R_2$ groups include isobutyl, n-hexyl, 3-(2-chlorophenyl)prop-2-yn-1-yl.

The group $R_3$ $R_3$ may for example be $C_1$–$C_6$ alkyl, phenyl, 2,- 3-, or 4-hydroxyphenyl, 2,- 3-, or 4-methoxyphenyl, 2,- 3-, or 4-pyridylmethyl, benzyl, 2,- 3-, or 4-hydroxy-benzyl, 2,- 3-, or 4-benzyloxybenzyl, 2,- 3-, or 4-$C_1$–$C_6$-alkoxybenzyl, or benzyloxy($C_1$–$C_6$ alkyl)-group; or the characterizing group of a natural amino acid, in which any functional group may be protected, any amino group may be acylated and any carboxyl group present may be amidated; or a group —[Alk]$_n$R$_6$ where Alk is a ($C_1$–$C_6$)alkyl or ($C_2$–$C_6$)alkenyl group optionally interrupted by one or more —O—, or —S— atoms or —N(R$_7$)— groups [where R$_7$ is a hydrogen atom or a ($C_1$–$C_6$)alkyl group], n is 0 or 1, and $R_6$ is an optionally substituted cycloalkyl or cycloalkenyl group; or a benzyl group substituted in the phenyl ring by a group of formula —OCH$_2$COR$_8$ where $R_8$ is hydroxyl, amino, ($C_1$–$C_6$)alkoxy, phenyl($C_1$–$C_6$)alkoxy, ($C_1$–$C_6$) alkylamino, di(($C_1$–$C_6$)alkyl)amino, phenyl($C_1$–$C_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histine, arginine, glutamic acid, and aspartic acid; or a heterocyclic($C_1$–$C_6$)alkyl group, either being substituted or mono- or di substituted in the heterocyclic ring with halo, nitro, carboxy, $(C_1-C_6)$alkoxy, cyano, $(C_1-C_6)$alkanoyl, trifluoromethyl$(C_1-C_6)$alkyl, hydroxy, formyl, amino, $(C_1-C_6)$alkylamino, di-$(C_1-C_6)$alkylamino, mercapto, $(C_1-C_6)$alkylthio, hydroxy$(C_1-C_6)$alkyl, mercapto$(C_1-C_6)$alkyl or $(C_1-C_6)$alkylphenylmethyl; or a group —$CR_aR_bR_c$, in which:

each of $R_a$, $R_b$ and $R_c$ is independently hydrogen, $(C_1-C_6)$ alkyl, $(C_2-C_6)$alkenyl, $(C_2-C_6)$alkynyl, phenyl$(C_1-C_6)$ alkyl, $(C_1-C_6)$cycloalkyl; or $R_c$ is hydrogen and $R_a$ and $R_b$ are independently phenyl or heteroaryl Such as pyridyl; or $R_c$ is hydrogen, $(C_1-C_6)$alkyl, $(C_2-C_6)$alkenyl, $(C_2-C_6)$ alkynyl, phenyl$(C_1-C_6)$alkyl, or $(C_3-C_8)$cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently $(C_1-C_6)$alkyl, $(C_2-C_6)$ alkenyl, $(C_2-C_6)$alkynyl, phenyl$(C_1-C_6)$alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —$CO_2H$, $(C_1-C_4)$perfluoroalkyl, —$CH_2OH$, —$CO_2$ $(C_1-C_6)$alkyl, —O$(C_1-C_6)$alkyl, —O$(C_2-C_6)$alkenyl, —S$(C_1-C_6)$alkyl, —SO$(C_1-C_6)$alkyl, —$SO_2(C_1-C_6)$ alkyl, —S$(C_2-C_6)$alkenyl, —SO$(C_2-C_6)$alkenyl, —$SO_2(C_2-C_6)$alkenyl or a group —Q—W wherein Q represents a bond or —O—, —S—, —SO— or —$SO_2$— and W represents a phenyl, phenylalkyl, $C_3-C_8$)cycloalkyl, $(C_3-C_8)$cycloalkylalkyl, $(C_4-C_8)$ cycloalkenyl, $(C_4-C_8)$cycloalkenylalkyl, heteroaryl or heteroarylalkyl group, which group W may optionally be substituted by one or more substituents independently selected from, hydroxyl, halogen, —CN, —$CO_2H$, —$CO_2(C_1-C_6)$alkyl, —$CONH_2$, —CONH $(C_1-C_6)$alkyl, —CONH$(C_1-C_6$alkyl$)_2$, —CHO, —$CH_2OH$, $(C_1-C_4)$perfluoroalkyl, —O$(C_1-C_6)$alkyl, —S$(C_1-C_6)$alkyl, —SO$(C_1-C_6)$alkyl, —$SO_2(C_1-C_6)$ alkyl, —$NO_2$, —$NH_2$, —NH$(C_1-C_6)$alkyl, —N$((C_1-C_6)$alkyl$)_2$, —NHCO$(C_1-C_6)$alkyl, $(C_1-C_6)$ alkyl, $(C_2-C_6)$alkenyl, $(C_2-C_6)$alkynyl, $(C_3-C_8)$ cycloalkyl, $(C_4-C_8)$cycloalkenyl, phenyl or benzyl.

Examples of particular $R_3$ groups include benzyl, phenyl, cyclohexylmethyl, pyridin-3-ylmethyl, tert-butoxymethyl, iso-butyl, sec-butyl, tert-butyl, 1-benzylthio-1-methylethyl, 1-methylthio-1-methylethyl, and 1-mercapto-1-methylethyl.

Presently preferred $R_3$ groups include phenyl, benzyl, tert-butoxymethyl and isobutyl.

The group $R_4$

Examples of particular ester and thioester groups $R_4$ groups include those of formula —(C═O)$OR_9$, —(C═O) $SR_9$, —(C═S)$SR_9$, and —(C═S)$R_9$ wherein $R_9$ is $(C_1-C_6)$ alkyl, $(C_2-C_6)$alkenyl, cycloalkyl, cycloalkyl$(C_1-C_6)$alkyl-, phenyl, heterocyclyl, phenyl$(C_1-C_6)$alkyl-, heterocyclyl $(C_1-C_6)$alkyl-, $(C_1-C_6)$alkoxy$(C_1-C_6)$alkyl-, $(C_1-C_6)$ alkoxy$(C_1-C_6$alkoxy$(C_1-C_6)$alkyl-, any of which may be substituted on a ring or non-ring carbon atom or on a ring heteroatom, if present. Examples of such $R_9$ groups include methyl, ethyl, n- and iso-propyl, n-, sec- and tert-butyl, 1-ethyl-prop-1-yl, 1-methyl-prop-1-yl, 1-methyl-but-1-yl, cyclopentyl, cyclohexyl, allyl, phenyl, benzyl, 2-, 3- and 4-pyridylmethyl, N-methylpiperidin-4-yl, 1-methyl-cyclopent-1 yl, adamantyl, tetrahydrofuran-3-yl and methoxyethyl.

Presently preferred are compounds of formula (1B) wherein $R_4$ is a carboxylate ester of formula-(C═O)$OR_9$, wherein $R_9$ is benzyl, cyclopentyl, isopropyl or tert-butyl.

The group R

Presently preferred R groups are hydrogen and methyl.

Specific examples of compounds of the invention include those prepared according to Examples 1–3 and 5–43 below, and salts, hydrates and solvates thereof.

Compounds presently preferred for their potencies as inhibitors of proliferation of various rapidly dividing tumor cells are:

2S-(3S-Hydroxycarbamoyl-2R-isobutyl-hex-5-enoylamino)-3-phenylpropionic acid cyclopentyl ester, 2S-(3S-Hydroxycarbamoyl-2R-isobutyl-hex-5-enoylamino)-3-phenylpropionic acid benzyl ester, 2S-{2R-[1S-Hydroxycarbamoyl-2-(thiophen-2-yl sulphanyl))-ethyl]-4-methyl-pentanoylamino}-3-phenyl-propionic acid isopropyl ester, 2S-(3S-Hydroxycarbamoyl-2R-isobutyl-hex-5-enoylamino)-4-methyl-pentanoic acid cyclopentyl ester, and p0 pharmaceutically acceptable salts, hydrates and esters thereof.

Compounds according to the present invention wherein $R_4$ is a carboxylate ester group may be prepared by a process comprising causing an acid of general formula (II)

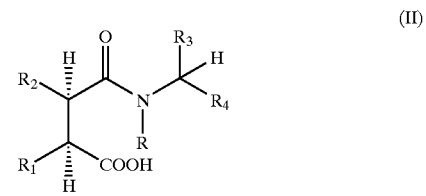

(II)

or an activated derivative thereof to react with hydroxylamine, O-protected hydroxylamine, or an N,O-diprotected hydroxylamine, or a salt thereof, R, $R_1$, $R_2$, $R_3$, and $R_4$ being as defined in general formula (I) except that any substituents in $R_1$, $R_2$, $R_3$, and $R_4$ which are potentially reactive with hydroxylamine, O-protected hydroxylamine, the N,O-diprotected hydroxylamine or their salts may themselves be protected from such reaction, then removing any protecting groups from the resultant hydroxamine acid moiety and from any protected substituents in $R_1$, $R_2$, $R_3$ and $R_4$.

Conversion of (II) to an activated derivative such as the pentafluorophenyl, hydroxycussinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in method (a) above include O-benzylhydroxylamine, O-4-methoxybenzylhydroxylamine, O-trimethylsilylhydroxylamine, and O-tert-butoxycarbonylhydroxylamine.

Examples of O,N-diprotected hydroxylamines for use in method (a) above include N,O-bis(benzyl)hydroxylamine, N,O-bis(4-methoxybenzyl)hydroxylamine, N-tertbutoxycarbonyl-O-tert-butyldimethylsilylhydroxylamine, N-tert-butoxycarbonyl-O-tetrahydropyranylhydroxylamine, and N,O-bis(tert-butoxycarbonyl)hydroxylamine.

Compounds of formula (II) may be prepared by a process comprising: coupling an acid of formula (III) or an activated derivative thereof with an amine of formula (IV)

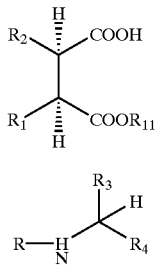

(III)

(IV)

wherein R, $R_1$, $R_2$, $R_3$, and $R_4$ are as defined in general formula (I) except that any substituents in $R_1$, $R_2$, $R_3$, and $R_4$ which are potentially reactive in the coupling reaction may themselves be protected from such reaction, and $R_{11}$ represents a hydroxy protecting group, and subsequently removing the protecting group $R_{11}$ and any protecting groups from $R_1$, $R_2$, $R_3$, and $R_4$.

Compounds of the invention wherein $R_4$ is a thioester may be prepared by coupling a compound of formula (IIIA) or an activated derivative thereof

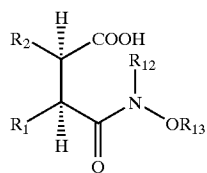

(IIIA)

wherein $R_1$ and $R_2$ are as defined in general formula (I) and $R_{12}$ and $R_{13}$ are respectively N- and O-protecting groups, with a compound of formula (IV) above wherein $R_4$ is a thioester group, and selectively removing the O- and N-protecting groups from the hydroxamic acid group.

Active derivatives of acids (III) and (IIIA) include activated esters such as the pentafluorophenyl ester, acid anhydrides and acid halides, chlorides. Suitable hydroxy protecting groups may be selected from those known in the art.

Amino acid esters and thioesters of formula (IV) are either known or are prepared by routine known synthetic methods.

As mentioned above, compounds of formula (I) above, and those of formula (I) excluded by the provisos in the definition of formula (I) above, are useful in human or veterinary medicine since they are active as inhibitors of the proliferation of cancer cells. The utility of the invention therefore lies in the treatment of cancers, such as those caused by over-proliferation of lymphoma, leukemia, myeloma, adenocarcinoma, carcinoma, mesothelioma, teratocarcinoma, choriocarcinoma, small cell carcinoma, large cell carcinoma, melanoma, retinoblastoma, fibrosarcoma, leiomyosarcoma, glioblastoma or endothelioma cells. It will be understood that different compounds (I) will have differing potencies as proliferation inhibitors depending on the type of cancer being treated.

The activity of any particular compound (I) in inhibiting proliferation of any particular cell type may be routinely determined by standard methods, for example analogous to those described in the Biological Example herein. From the fact that compounds (I) which are poorly active as inhibitors of MMPs are nonetheless active in inhibiting proliferation of cancer cells, it is inferred that their utility in treating cancers is different from or supplementary to the utility of effective MMP inhibitors in the treatment of cancers.

Another aspect of the invention provides a compound selected from the group consisting of:

2(R or S)-[2-R-(S-Hydroxy-hydroxycarbamoyl-methyl)-4-methyl-pentanoylamine]-2-phenyl-ethanoic acid cyclopentyl ester, 2(R or S)-(3S-Hydroxycarbamoyl-2R-isobutyl-hex-5-enoylamino)-2-phenylethanoic acid isopropyl ester, 2(R or S)-[2R-(S-Hydroxycarbamoyl-methoxy-methyl)-4-methyl-pentanoylamino]-3-phenylethanoic acid cyclopentyl ester, 2(R or S)-(3S-Hydroxycarbamoyl-2R-isobutyl-hex-5-enoylamino)-2-(4-methoxyphenyl)ethanoic acid cyclopentyl ester, 2(R or S)-(3S-Hydroxycarbamoyl-2R-isobutyl-hex-5-enoylamino)-2-(thien-2-yl)ethanoic acid cyclopentyl ester, 2(R or S)-(3S-Hydroxycarbamoyl-2R-isobutyl-hex-5-enoylamino)-2-(thien-3-yl)ethanoic acid cyclopentyl ester, and a pharmaceutically or veterinarily acceptable salts, hydrates or solvates thereof.

The 2-S diastereomers of the above compounds are especially preferred.

It is understood that different compounds of the invention will have differing potencies as proliferation inhibitors depending on the type of cancer being treated. The activity of any particular compound of the invention in inhibiting proliferation of any particular cell type may be routinely determined by standard methods, for example analogous to those described in the Biological Example herein.

In a further aspect of the invention there is provided a pharmaceutical or veterinary composition comprising a compound of the invention as defined by reference to formula (IB) above, together with a pharmaceutically or veterinarily acceptable excipient or carrier. One or more compounds of the invention may be present in the composition together with one or more excipient or carrier.

The compounds with which the invention is concerned may be prepared for administration by any route consistent with their pharmacokinetic properties.

Orally administratable compositions may be in the form of tablets, capsules, powders, granules, lozenges, and liquid or gel preparations, such as oral, topical, or sterile parenteral solutions or suspensions. Tablets an capsules for oral administration may be in unit dose presetnation form, and may contain conventional excipients such as binding agents, for example syrup, acacia, gelatin, sorbitol, tragacanth, or polyvinylpyrrolidone; fillers for example lactose, sugar, maizestarch, calcium phosphate, sorbitol or glycine; tabletting lubricant, for example magnesium stearate, talc, polyethylene glycol or silica; disintegrants for example potato starch, or acceptable wetting agents such as sodium laurylsulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations, which may be used for the drug, are conventional formulations well known in the art, for example as described in standard textbooks of pharmaceuticals such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Although the present invention and that of International Application PCT/GB97/02398 are not limited by any particular theory of mechanism of action, the anti-proliferative effect is presently believed to be due to the inherent ability of the compounds, which inhibit one or more enzymes residing within the proliferating cells. According to this theory of the mechanism of activity, it follows that the most active compounds are those which are inherently most capable of passing through the cell wall into the cell interior. Since the compounds are esters (or thioesters) it is believed that esterases within the cell wall hydrolyze the compounds to the corresponding acids, and that the anti-proliferative activity may ultimately be due to inhibition of one or more intracellular enzymes by the unhydrolyzed ester, by the corresponding acid, or by a combination of both. If this is correct, the later inherent property is the more likely, since it is known that the rate of enzymatic hydrolysis may be more or less rapid, depending on the particular ester and the esterases present in the microenvironment of the ester within the cell. Cell penetrating pro-drugs of the acids or cell penetrating formulations of the acids are therefore expected to have the anti-proliferative effects of the esters described herein and in PCT/GB97/02398. Thus, while known MMP inhibitors work from without the target cell, the esters and thioester compounds of the present invention work from within the target cell.

The following examples 1–3 and 5–43 illustrate various embodiments of the invention. Example 4 describes the preparation of a compound for comparison with those of the invention. The following abbreviations have been used in the examples DCF—Dichloromethane
DMF—N,N-Dimethylformamide
NMM—N-Methylmorpholine
TFA—Trifluoroacetic acid
HOBT—1-Hydroxybenzotriazole
MeOd—methanol-$d_4$ ($CD_3OD$)

Column chromatography was performed with flash grade silica gel. $^1$H-NMR and $^{13}$C-NMR were recorded on a Bruker AC 250E spectrometer at 250.1 and 62.9 MHz respectively. $CDCl_3$methanol-$d_4$ and dimethylsulphoxide-$d_6$. (DMSO-$d_6$) were used as solvents and internal reference and spectra are reported as δ ppm from TMS.

EXAMPLE 1

2S-(3S-Hydroxycarbamoyl-2R-isobutyl-hex-5-enoylamino)-3-phenylpropionic acid methyl ester

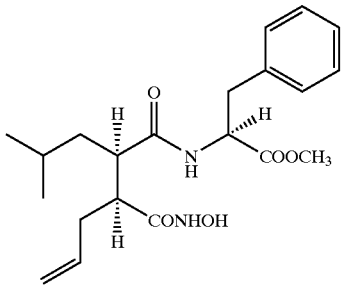

(a) 2S-(3S-tert-Butoxycarbonyl-2R-isobutyl-hex-5-enoylamino)-3-phenylpropionic acid methyl ester.

A solution of L-phenylalanine methyl ester hydrochloride (3.9 g, 17.9 mmol) and NMM (2.0 mL, 17.9 mmol) in DMF (15 mL) was cooled in an ice-water bath and treated with 3S-tert-butoxycarbonyl-2R-isobutyl-hex-5-enoic acid pentafluorophenyl ester (6.5 g, 14.9 mmol, WO 94/1625). The reaction was allowed to warm to room temperature and stirred overnight. The reaction mixture was concentrated under reduced pressure and the residue taken up in ethyl acetate and washed with 1M hydrochloric acid, 1M sodium carbonate and brine. The solution was dried over sodium sulphate, filtered and concentrated under reduced pressure to provide 2S-(3S-tert-butoxycarbonyl-2R-isobutyl-hex-5-enoylamino)-3-phenylpropionic acid methyl ester as a yellow solid (4.0 g, 52%). $^1$H-NMR; δ ($CDCl_3$), 7.28–7.07 (5H, m), 6.58 (1H, d), 5.75–4.94 (1H, m), 5.07–4.75 (3H, m), 3.53 (3H, s), 3.13 (1H, dd), 2.97 (1H, dd), 2.45–2.22 (3H, m), 1.96–1.01 (2H, m), 1.38 (9H, s), 0.98–0.72 (2H, m) and 0.78–0.72 (6 H, m).

(b) 2S-(3S-Hydroxycarbonyl-2R-isobutyl-hex-5-enoylamino)-3-phenylpropionic acid methyl ester.

A solution of 2S-(3S-tert-butoxycarbonyl-2R-isobutyl-hex-5-enoylamino)-3-phenylpropionic acid methyl ester (4.0 g, 9.3 mmol) in a mixture of TFA and DCM (1:1, 10 mL-) was allowed to stand at 5° C. overnight. The reaction mixture was concentrated under reduced pressure. Crystallization of the product from ethyl acetate/hexane gave 2S-(3-hydroxycarbonyl-2R-isobutyl-hex-5-enoylamino)-3-phenylpropionic acid methyl ester as a white solid (2.02 g, 58%). $^1$H-NMR; δ ($CDCl_3$), 7.28–7.08 (5H, m), 5.57–5.42 (1H, m), 4.85–4.74 (3H, m), 3.68 (3H, s), 3.25 (1H, dd), 2.88 (1H, dd), 2.55 (1H, m), 2.38–2.24 (1H, m), 1.90–1.75 (1H, m), 1.62–1.40 (3H, m), 1.08–0.92 (1H, m), 0.88 (3H, d) and 0.79 (3H, d).

(c) 2S-(3S-Hydroxycarbamoyl-2R-isobutyl-hex-5-enoylamino)-3-phenylpropionic acid methyl ester.

A solution of 2S-(3S-Hydroxycarbonyl-2R-isobutyl hex-5-enoylamino) 3-phenylpropionic acid methyl ester (2.02 g, 5.38 mmol) in DMF (15 mL) was cooled in an ice-water bath. N-(3-dimethylaminopropyl)-N'-ethylcarbodiimide hydrochloride (1.24 g, 5.38 mmol) and HOBT (873 mg, 6.46 mmol) were added with stirring. The reaction was allowed to warm to room temperature and after 2 hours a solution of hydroxylamine hydrochloride (561 mg, 8.07 mmol) and NMM (0.9 mL, 8.07 mmol) in DMF (5 mL) added. After stirring overnight the reaction mixture was concentrated under reduced pressure. The residue was treated with a 2:1 mixture of ether/water to precipitate a white solid. The product was recrystallized from methanol to yield 2S-(3S-hydroxycarbamoyl-2R-isobutyl-hex-5-enoylamino)-3-phenylpropionic acid methyl ester as a white solid (309 mg, 15%). $^1$H-NMR; δ (methanol-d$_4$), 8.67 (1H, d, J=7.7 Hz), 7.23–7.14 (5H, m), 5.45–5.32 (1H, m), 4.85–4.74 (3H, m), 3.68 (3H, s), 3.24–3.09 (1H, m), 2.91–2.66 (1H, m), 2.47–2.39 (1H, m), 2.01–1.76 (2H, m), 1.49–1.36 (3H1, m), 1.09–0.95 (1H, m), 0.85 (3H, d, J=6.4 Hz) and 0.80 (3H, d, J=6.4 Hz); $^{13}$C-NMR; δ (methanol-d$_4$), 176.5, 173.3, 172.4, 138.4, 136.1, 130.2, 129.5, 128.0, 117.3, 65.3, 55.1, 55.0, 52.7, 41.6, 38.1, 35.7, 26.7, 24.6 and 21.6.

EXAMPLE 2

2S-(3S-Hydroxycarbamoyl-2R-isobutyl-hex-5-enoylamino)-3-phenylpropionic acid ethyl ester

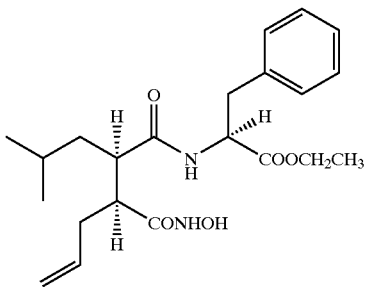

(a) 2S-(3S-tert-Butoxycarbonyl-2R-isobutyl-hex-5-enoylamino)-3-phenylpropionic acid ethyl ester.

A solution of 1-phenylalanine ethyl ester (4.3 g, 22.0 mmol) in DMF (20 mL) was cooled in an ice-water bath and treated with 3S-tert-butoxy-carbonyl-2R-isobutyl-hex-5-enoic acid pentafluorophenyl ester (10.7 g, 24.0 mmol). The reaction was stirred at 35° C. overnight. The reaction mixture was concentrated under reduced pressure and the residue taken up in ethyl acetate and washed with 1M hydrochloric acid, 1M sodium carbonate and brine. The solution was dried over sodium sulphate, filtered and concentrated under reduced pressure to provide 2S-(3S-tert-butoxycarbonyl-2R-isoobutyl-hex-5-enoylamino)-3-phenylpropionic acid ethyl ester as a yellow solid (13.7 g, used directly in (b)). $^1$H-NMR; δ (CDCl$_3$), 7.35–7.12 (5H, m), 6.25 (1H, d), 5.84–5.50 (1H, m), 5.18–5.02 (1H, m), 4.99–4.89 (2H, m), 4.15–4.08 (2H, m), 3.20 (1H, dd), 3.06 (1H, dd), 2.52–2.32 (1H, m), 1.95–1.82 (2H, m), 1.72–1.55 (2H, m), 1.42 (9H, s), 1.28–1.21 (3H, m), 0.98–0.93 (2H, m) and 0.88–0.80 (6H, m).

(b) 2S-(3S-Hydroxycarbonyl-2R-isobutyl-hex-5-enoylamino)-3-phenylpropionic acid ethyl ester.

A solution of 2S-(3S-tert-butoxycarbonyl-2R-isobutyl-hex-5-enoylamino)-3-phenylpropionic acid ethyl ester (13.7 g, 31.0 mmol) in a mixture of TFA and DCM (1:1, 10 mL) was allowed to stand at room temperature overnight. The reaction mixture was concentrated under reduced pressure. Crystallization of the product from ethyl acetate/hexane gave 2S-(3S-hydroxycarbonyl-2R-isobutyl-hex-5-enoylamino)-3-phenylpropionic acid ethyl ester as a white solid (1.5 g, 12%). $^1$H-NMR; δ0 (CDCl$_3$), 7.35–7.28 (3H-1, m), 7.18–7.10 (2H, m), 6.22 (1H, d), 5.77–5.60 (1H, m), 5.08–4.99 (3H-1, m), 4.22 (2H, q), 3.24 (1H, dd), 3.07 (1H, dd), 2.61–2.52 (1H, m), 2.45–2.28 (2H, m), 2.08–1.94 (1H, m), 1.75–1.64 (1H, m), 1.60–1.45 (1H, m), 1.28 (3H, t), 1.21–109 (1H, m) and 0.86 (6H, d).

(c) 2S-(3S-Hydroxycarbamoyl-2R-isobutyl-hex-5-enoylamino)-3-phenylpropionic acid ethyl ester.

A solution of 2S-(3S-hydroxycarbonyl-2R-isobutyl-hex-5-enoylamino)-3-phenylpropionic acid ethyl ester (2.2 g, 5.38 mmol) in DMF (20 mL) was cooled in an ice-water bath. N-(3-dimethylamino propyl)-N'-ethylcarbodiimide hydrochloride (1.3 g, 6.78 mmol) and HOBT (916 mg, 6.78 mmol) were added with stirring. The reaction was allowed to warm to room temperature and after 2 hours a solution of hydroxylamine hydrochloride (589 mg, 8.48 mmol) and NMM (0.9 mL, 8.48 mmol) in DMF (10 mL) added. After stirring overnight the reaction mixture was concentrated under reduced pressure. The residue was treated with a 2:1 mixture of ether/water to precipitate a white solid, which was collected by filtration and washed with hot ethyl acetate. Drying under vacuum provided 2S-(3S-hydroxycarbamoyl-2R-isobutyl-hex-5-enoylamino)-3-phenylpropionic acid ethyl ester as a white solid (1.8 g, 79%). $^1$H-NMR; δ (methanol-d$_4$), 8.65 (1H, d, J=8.4 Hz), 7.81–7.09 (5H, m), 5.45–5.32 (1H, m), 4.89–4.71 (3H, m), 4.13 (2H, q, J=7.1 Hz), 3.23–3.06 (2H, m), 2.48–2.38 (1H, m), 2.02–1.75 (3H, m), 1.51–130 (2H, m), 1.21 (3H, t, J=7.1 Hz), 1.01–0.90 (1H, m), 0.86 (3H, d, J=6.4 Hz) and 0.79 (3H, d, J=6.4 Hz); $^{13}$C-NMR; δ (methanol-d$_4$), 176.5, 172.9, 172.4, 138.4, 136.1, 130.3, 129.5, 128.0, 117.3, 65.1, 62.4, 56.5, 55.2, 55.1, 54.6, 43.4, 41.6, 38.2, 37.3, 35.7, 27.0, 26.6, 24.6, 21.7, 15.7 and 14.5.

EXAMPLE 3

2S-(3S-Hydroxycarbamoyl-2R-isobutyl-hex-5-enoylamino)-3-phenylpropionic acid isopropyl ester.

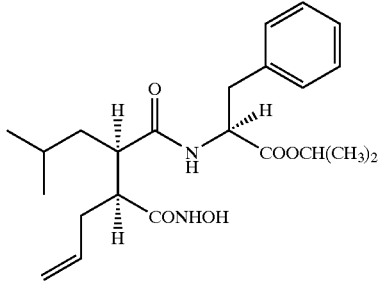

(a) 2S-(3S-tert-Butoxycarbonyl-2R-isobutyl-hex-5-enoylamino)-3-phenylpropionic acid isopropyl ester.

A solution of L-phenylalanine isopropyl ester (3.9 g, 18.8 mmol) in DMF (15 mL) was cooled in an ice-water bath and treated with 3S-tert-butoxycarbonyl-2R-isobutyl-hex-5-enoic acid pentafluorophenyl ester (9.03 g, 20.7 mmol). The reaction was allowed to warm to room temperature and stirred overnight. The reaction mixture was concentrated under reduced pressure. The residue was taken up in ethyl acetate and washed with 1M hydrochloric acid, 1M sodium carbonate and brine. The solution was dried over sodium sulfate, filtered and concentrated under reduced pressure. The product was purified by column chromatography using a gradient elution of 100% DCM to 10% methanol/DCM. Product containing fractions were combined and solvent removed to yield 2S-(3S-tert-butoxycarbonyl-2R-isobutyl-hex- 5-enoylamino)-3-phenylpropionic acid isopropyl ester as a yellow solid (3.5 g, 41%). $^1$H-NMR; δ (CDCl$_3$), 7.44–7.15 (5H, m), 6.46 (1H, d), 5.72–5.48 (1H, m), 5.15–4.88 (3H, m), 3.25 (1H, dd), 3.11 (1H, dd), 2.60–2.48 (2H, m), 2.00–1.78 (1H, m), 1.72–1.58 (1H, m), 1.45 (9H, s), 1.35–1.18 (9H, m), 0.98–0.91 (1H, m) and 0.88–0.80 (6H, m).

(b) 2S-(3S-Hydroxycarbonyl-2R-isobutyl-hex-5-enoylamino)-3-phenylpropionic acid isopropyl ester.

A solution of 2S-(3S-tert-butoxycarbonyl-2R-isobutyl-hex-5-enoylamino)-3-phenylpropionic acid isopropyl ester (3.5 g, 7.6 mmol) in a mixture of TFA and DCM (1:1, 10 mL) was allowed to stand at 5° C. overnight. The reaction mixture was concentrated under reduced pressure. Addition on ether to the residue gave 2S-(3S-hydroxycarbonyl-2R-isobutyl-hex-5-enoylamino)-3-phenylpropionic acid isopropyl ester as a white solid (261 mg, 8%). $^1$H-NMR; δ (CDCl$_3$), 7.38–7.25 (3H, m), 7.18–7.12 (2H, m), 6.49 (1H, d), 5.70–5.55 (1H, m), 5.13–4.89 (3H, m), 3.24 (1H, dd), 3.05 (1H, dd), 2.63–2.45 (2H, m), 2.28–2.15 (1H, m), 2.02–1.79 (1H, m), 1.70–1.61 (1H, m), 1.58–1.40 (1H, m), 1.32–1.18 (7H, m), 0.98–0.91 (1H, m), 0.85–0.82 (6H, m).

(c) 2S-(3S-=Hydroxycarbamoyl-2R-isobutyl-hex-5-enoylamino)-3-phenylpropionic acid isopropyl ester.

A solution of 2S-(3S-hydroxycarbonyl-2R-isobutyl-hex-5-enoylamino)-3-phenylpropionic acid isopropyl ester (260 mg, 0.64 mmol) in DMF (10 mL) was cooled in an ice-water bath. N-(3-dimethylaminopropyl)-N'-ethylcarbodiimide hydrochloride (148 mg, 0.77 mmol) and HOBT (104 mg, 0.77 mmol) were added with stirring. The reaction was allowed to warm to room temperature and after 2 hours a solution of hydroxylamine hydrochloride (67 mg, 0.96 mmol) and NMM (0.1 mL, 0.96 mmol) in DMF (5 mL) added. After stirring overnight the reaction mixture was concentrated under reduced pressure and the product was purified by chromatography on acid-washed silica using 5–10% methanol in DCM. Recrystallization from ethyl acetate/hexane provided 2S-(3S-hydroxycarbamoyl-2R-isobutyl-hex-5-enoylamino)-3-phenylpropionic acid isopropyl ester as a white solid (12 mg, 4%). $^1$H-NMR; δ (methanol-d$_4$), 8.64 (1H, d, J=8.2 Hz), 7.23–7.11 (5H, m), 5.41–5.34 (1H, m), 5.02–4.92 (1H, m), 4.85–4.69 (2H, m), 3.23–3.16 (1H, m), 2.89–2.80 (1H, m), 2.46–2.39 (1H, m), 2.01–179 (2H, m), 1.50–1.42 (2H, m), 1.23–1.56 (7H, m), 0.99–0.95 (1H, m), 0.86 (3H, d, J=6.3 Hz), and 0.80 (3H, d, J=6.4 Hz); $^{13}$C-NMR; δ(methanol-d$_4$), 176.4, 176.3, 138.4, 136.1, 130.3, 129.5, 123.0, 117.3, 70.2, 55.4, 41.6, 38.3, 35.7, 26.6, 24.5, 22.0, 21.9 and 21.7.

EXAMPLE 4

(For Comparison)

3S-(2-Phenyl-1R-methylcarboxy-ethylcarbamoyl)-2R, 5-dimethylhexanohydroxamic acid

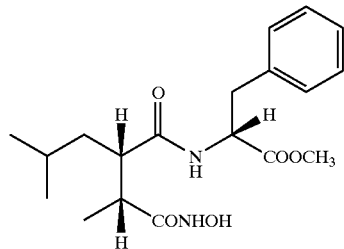

(a) 3S-(2-Phenyl-1R-methylcarboxy-ethylcarbamoyl)-2-benzyloxygarbonyl-5-methylhexanoic acid benzyl ester A solution of 3S-hydroxycarbonyl-2-benzyloxycarbonyl-5-methylhexanoic acid benzyl ester (10.0 g, 25 mmol, WO 90/05719) in DMF (100 ml) was treated with HOBT (5.1 g, 38 mmol), N-(3-dimethylaminopropyl)-N'-ethylcarbodiimide hydrochloride (5.9 g, 30 mmol), D-phenylalanine methyl ester (5.2 g, 29 mmol) and NMM (4.1 mL, 38 mmol). The yellow reaction mixture was stirred at room temperature overnight and concentrated under reduced pressure. The residue was taken up in ethyl acetate and washed with 1M hydrochloric acid (x2), saturated sodium bicarbonate (x2) and brine. The solution was dried over magnesium sulphate, filtered and concentrated to provide 3S-(2-phenyl-1R-methylcarboxy-ethylcarbamoyl)-2-benzyloxycarbonyl-5-methylhexanoic acid benzyl ester as colourless oil (12.2 g, 87%). $^1$NMR; δ (CDCl$_3$), 7.41–7.17 (15H, m), 6.25(1H,d, J=7.9 Hz), 5.22–5.04 (4H, m), 4.90–4.83 (1H, m), 3.86 (1H, d, J=10.1 Hz), 3.67 (3H, s), 3.11 (1H, dd, J=13.8, 5.6 Hz), 3.02–2.91 (2H, m), 1.69–1.54 (1H, m), 1.53–1.46 (1H, m), 1.05–0.96 (1H, m), 0.79 (3H, d, J=6.5 Hz) and 0.78 (3H, d, J=6.4 Hz).

(b) 3S-(2-Phenyl-1R-methylcarboxy-ethylcarbamoyl)-2-methylene-5-methylhexanoic acid.

A solution of 3S-(2-phenyl-1R-methylcarboxy-ethylcarbamoyl)-2-benzyloxycarbonyl-5-methylhexanoic acid benzyl ester (3.4 g, 6.1 mmol) in ethanol (30 mL), was treated under an inert atmosphere with palladium catalyst (100 mg, 10% on charcoal) and then stirred under an atmosphere of hydrogen gas for 1 hour. The catalyst was removed by filtration through a glass fibre pad. The filtrate was treated with piperidine (0.7 mL) and formaldehyde (3.2 mL of a 37% wt aqueous solution, 7.05 mmol) and allowed to stand at room temperature overnight. The reaction mixture was concentrated under reduced pressure and the residue partitioned between ethyl acetate and saturated sodium bicarbonate solution. The aqueous layer was separated, acidified with 1M hydrochloric acid to pH 1 and extracted with ethyl acetate. The organic extracts were dried over magnesium sulphate, filtered and concentrated under reduced pressure to yield 3S-(2-phenyl-1R-methylcarboxy-ethylcarbamoyl)-2-methylene-5-methylhexanoic acid as a white solid (1.05 g, 50%). $^1$NMR; δ (CDCl$_3$), 7.26–7.14 (3H, m), 7.06–7.02 (2H, m), 6.57 (1H, d, J=8.0), 6.44 (1H, s), 5.88 (1H, s), 4.93–4.81 (1H, m), 3.72 (3H, s), 3.54–3.48 (1H, m), 3.13 (1H, dd, J=13.9, 5.7 Hz), 3.02 (1H, dd, J=13.8, 6.4 Hz), 1.85–1.76 (1H, m), 1.58–1.41 (2H, m) and 0.90–0.85 (6H, m).

(c) 3S-(2-phenyl-1R-methylcarboxy-ethylcarbamoyl)-2R, 5-dimethylhexanoic acid

A solution of 3S-(2-phenyl-1R-methylcarboxy-ethylcarbamoyl)-2-methylene-5-methylhexanoic acid (960 mg, 2.77 mmol) in ethanol was treated under an inert atmosphere with palladium catalyst (50 mg, 10% on charcoal). The reaction mixture was stirred under an atmosphere of hydrogen gas for 90 minutes. The catalyst was removed by filtration through a glass fibre pad. The filtrate was concentrated under reduced pressure to yield 3S-(2-phenyl-1R-methylcarboxy-ethylcarbamoyl)-2R,5-dimethylhexanoic acid as a white solid (900 mg, 93%). $^1$NMR; δ (CDCl$_3$), 7.33–7.20 (3H, m), 7.15–7.11 (2H, m), 6.25 (1H, d, J=8.1 Hz), 4.99–4.90 (1H, m), 3.75 (3H, s), 3.19 (1H, dd, J=13.9, 5.5 Hz), 3.05 (1H, dd, J=14.0, 7.3 Hz), 2.63–2.54 (1H, m), 2.47–2.41 (1H, m), 1.73–1.61 (1H, m), 1.60–1.44 (1H, m), 1.20–1.10 (1H, m), 1.03 (3H, d, J=7.1 Hz), 0.86 (3H, d, J=6.5 Hz) and 0.85 (3H, d, J=6.5 Hz).

(d) 3S-(2-phenyl-1R-methylcarboxy-ethylcarbamoyl)-2R,5-dimethylhexanohydroxamic acid.

A solution of 3S-(2-phenyl-1R-methylcarboxy-ethylcarbamoyl)-2R, 5-dimethylhexanoic acid (850 mg, 2.44 mmol), HOBT (395 mg, 2.92 mmol), O-benzylhydroxylamine (360 mg, 2.92 mmol) and N-(3-dimethylaminopropyl)-N'-ethylcarbodiimide hydrochloride (560 mg, 2.92 mmol) was stirred at room temperature for 96 hours. The reaction mixture was concentrated under reduced pressure to a colourless oil. The residue was taken up in ethyl acetate and washed with 2M hydrochloric acid (x2), saturated sodium bicarbonate (x2) and brine. The solution was dried over magnesium sulphate, filtered and concentrated under reduced pressure to a white solid. The solid was taken up in a 10% mixture of cyclohexene and ethanol (40 mL), treated with palladium catalyst (50 mg, 10% on charcoal) and heated at 80 20 C. for 1 Hour. The catalyst was removed by filtation and the filtrate concentrated under reduced pressure. The product was taken up in methanol and ether added to provide 3S-(2-phenyl-1R-methylcarboxy-ethylcarbamoyl)-2R, 5-dimethylhexanohydroxamic acid as a white solid (340 mg, 38%). $^1$H-NMR; δ (methanol-$d_4$), 8.57 (1H, d, J=8.3 Hz), 7.23–7.04 (5H, m), 4.71–4.64 (1H, m), 3.60 (3H, s), 3.14 (1H, dd, J=14.0, 4.8 Hz), 2.81 (1H, dd, J=14.0, 10.7 Hz), 2.35 (1H, dt, J=10.9, 3.0 Hz), 2.01–191 (1H, m), 1.43–1.29 (2H, m), 0.92–0.82 (1H, m), 0.78 (3H, d, J=6.4 Hz), 0.72 (3H, d, J=6.5 Hz), and 0.49 (3H, d, J=6.8 Hz); $^{13}$C-NMR; δ (methanol-$d_4$), 178.0, 174.7, 161.0, 131.6, 129.1, 54.0, 50.0, 43.3, 43.0, 39.5, 26.1, 25.8, 23.0, 18.2 and 17.6.

EXAMPLE 5

3R-(2-Phenyl-1S-methylcarboxy-ethylcarbamoyl)-2S, 5-dimethylhexanohydroxamic acid.

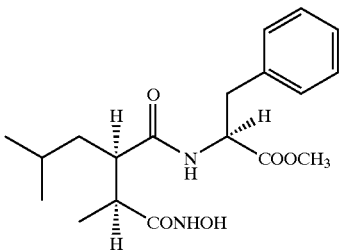

Using procedures similar to those described for example 4 and starting with 3R-hydroxycarbonyl-2-benzyloxycarbonyl-5-methylhexanoic acid benzyl ester (WO 90/05719) and L-phenylalanine methyl ester, 3R-(2-phenyl-1S-methylcarboxyethylcarbamoyl)-2S, 5-dimethylhexanohydroxamic acid was prepared as a white solid. $^1$H-NMR and $^{13}$C-NMR spectral data were directly analogous to those described for the enantiomer, example 4.

EXAMPLE 6

2S-(3S-Hydroxycarbamoyl-2R-isobutyl-hex-5-enoylamino)-3-phenyilpropionic acid tert-butyl ester.

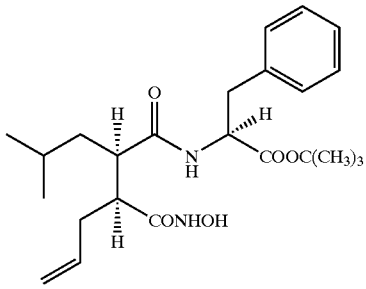

(a) 2S-[1R-(1S-tert-Butoxycarbonyl-2-phenyl-ethylcarbamoyl)-3-methyl-butyl]-pent-4-enoic acid allyl ester.

A solution of 2S-allyl-3R-isobutyl-succinic acid 1-allyl ester (830 mg, 3.3 mmol, WO97/18183), HOBT (504 mg, 3.7 mmol) and N-(3-dimethylaminopropyl)-N'-ethylcarbodiimide hydrochloride (714 mg, 3.7 mmol) in DMF (10 mL) was stirred for 10 minutes. A suspension of L-phenylalanine tert butyl ester hydrochloride (800 mg, 3.1 mmol) and NMM (376 μL, 3.4 mmol) in DMF (5 mL) was added dropwise to the reaction mixture. The reaction mixture was stirred for 18 hours at room temperature. The reaction mixture was concentrated under reduced pressure. The residue was taken up in ethyl acetate and washed with 1M hydrochloric acid, saturated sodium bicarbonate and brine. The organic solution was dried over magnesium sulphate, filtered and concentrated under reduced pressure. The product was purified by column chromatography on silica gel eluting with a gradient of 9:1 to 2:1 Hexane/ ethyl acetate. Product containing fractions were combined and solvent removed under reduced pressure to leave 2S[1R(1S-tert-butoxycarbonyl-2-phenyl-ethylcarbamoyl)-3-methyl-butyl]-pent-4-enoic acid allyl ester as a white solid (1.29 g, 91%). $^1$H-NMR; δ (CDCl$_3$), 7.32–7.16 (5H, m), 5.99 (1H, d, J=8.1 Hz), 5.89 (1H, ddt, J=17.2, 10.4, 5.8 Hz), 5.69–5.53 (1H, m), 5.32 (1H, dq, J=17.2, 1.5 Hz), 5.23 (1H, ddd, J=10.4, 1.3, 1.2 Hz), 4.96–4.77 (3H, m), 4.56 (2H, dd, J=5.8, 1.1 Hz), 3.15–2.96 (2H, m), 2.66 (1H, dt, J=9.7, 5.1 Hz), 2.38 (1H, dt, J=10.4, 3.3 Hz), 2.11–1.90 (2H, m), 1.71–159 (1H, m), 1.53–1.41 (1H, m), 1.40 (9H, s), 1.07–0.94 (1H, m), 0.85 (3H, d, J=6.5 Hz) and 0.83 (3H, d, J=6.5 Hz)

(b) 2S-[1R-(1S-tert-Butoxycarbonyl-2-phenyl-ethylcarbamoyl)-3-methyl-butyl]-pent-4-enoic acid.

A solution 2S-[1R-(1S-tert-butoxycarbonyl-2-phenyl-ethylcarbamoyl)-3-methyl-butyl]-pent-4-enoic acid allyl ester (1.29 g, 2.82 mmol) in THF (15 mL) was treated with morpholine (300 μL) and tetrakis (triphenylphosphine) palladium (0) (40 mg) the reaction was allowed to stir at room temperature overnight. The reaction mixture was partitioned between ethyl acetate and 1M hydrochloric acid. The organic layer was dried over magnesium sulphate, filtered and concentrated under reduced pressure. The crude product was purified by column chromatography on silica gel eluting with 5% methanol in DCM. Product containing fractions were combined and solvent removed under reduced pressure to yield 2S-[1R(1S-tert-butoxycarbonyl-2-phenyl-ethylcarbamoyl)-3-methyl-butyl]-pent-4-enoic acid as a white solid (423 mg, 34%). $^1$H-NMR; δ (CDCl$_3$), 7.34–7.20 (3H, m), 7.19–7.12 (2H, m), 6.20 (1H, d, J=9 Hz), 5.75–5.57 (1H, m), 4.79 (1HG, dd, J=14.3, 6.5 Hz), 3.18 (1H, dd, J=14.0, 6.1 Hz), 3.03 (1H, dd, J=14.0, 6.8 Hz), 2.57–2.33 (3H, m), 2.08–1.94 (1H, m), 1.72–1.37 (2H, m), 1.44 (9H, s), 1.16 (1H, ddd, J=13.8, 9.8, 3.5 Hz) and 0.87–0.84 (6H, m).

(c) 2S-(3S-Hydroxycarbamoyl-2R-isobutyl-hex-5-enoylamino)-3-phenyl-propionic acid tert-butyl ester.

A solution of 2S-[1R-(1S-tert-butoxycarbonyl-2-phenyl-ethylcarbamoyl)-3-methyl-butyl]-pent-4-enoic acid (400 mg, 1.0 mmol), N-(3-dimethylaminopropyl)-N'-ethylcarbodiimide hydrochloride (232 mg, 1.2 mmol) and HOBT (164 mg, 1.2 mmol) in DMF (10 mL) was stirred at 0° C. for 2 hours. Hydroxylamine hydrochloride (105 mg, 1.5 mmol) was taken up in DMF (2 mL) and NMM (166 μL, 1.5 mmol) added. After 10 minutes the hydroxylamine solution was added to the reaction mixture which was allowed to stir at room temperature for 18 hours. DMF was removed under reduced pressure and the residue partitioned between ethyl acetate and 1.0M hydrochloric acid. The organic layer was separated and washed with saturated sodium bicarbonate and brine before drying over magnesium sulfate. Filtration, evaporation and recrystallization from hot ethyl acetate yielded 2S-(3S-hydroxycarbamoyl- 2R-isobutyl-hex-5-enoylamino)-3-phenyl-propionic acid tert-butyl ester as a white solid (248 mg, 64%). $^1$H-NMR; δ (methanol-d$_4$), 8.52 (1H, d, J=8.4 Hz), 7.18–7.03 (5H, m), 5.34–5.28 (1H, m), 4.79–4.64 (2H, m), 4.62–4.55 (1H, m), 3.03 (1H, dd, J=13.9, 5.2 Hz), 2.77 (1H, dd, J=13.9, 10.5 Hz), 2.39–2.31 (1H, m), 1.96–1.85 (1H, m), 1.81–168 (1H, m), 1.44–1.22 (3H, m), 1.34 (9H, s), 0.94–0.89 (1H, m), 0.80 (3H, d, J=6.4 Hz) and 0.73 (3H, d, J=6.5 Hz). $^{13}$C-NMR; δ (methanol-d$_4$), 176.2, 172.4, 172.1, 138.4, 136.1, 130.3, 129.5, 127.9, 117.3. 82.8, 78.9, 55.8, 47.9, 41.6, 38.4, 35.7, 28.2, 26.6, 24.5 and 21.8.

EXAMPLE 7

2S-(2R-Hydroxycarbamoylmethyl-4-methyl-pentanoylamino)-3-phenyl-propionic acid isopropyl ester.

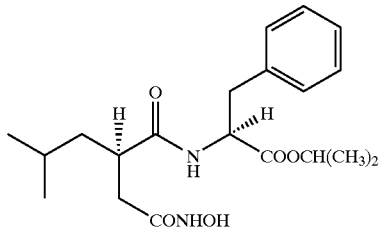

(a) 3R-(1S-Isopropoxycarbonyl-2-phenyl-ethylcarbamoyl)-5-methyl-hexanoic acid tert-butyl ester.

A solution of 3R-isobutyl-succinic acid 1-tert butyl ester (1.17 g, 5.1 mmol), L-phenylalanine isopropyl ester (1.17 g, 5.1 mmol), N-(3-dimethylaminopropyl)-N'-ethylcarbodiimide hydrochloride (972 mg, 5.1 mmol), and HOBT (685 mg, 5.1 mmol) in ethyl acetate (30 mL) was heated under reflux for 18 hours. The reaction mixture was diluted with ethyl acetate and washed with 1M hydrochloric acid, saturated sodium bicarbonate and brine before drying over magnesium sulphate, filtration and concentration under educed pressure to yield 3R-(1S-isopropoxycarbonyl-2-phenyl-ethylcarbamoyl)-5-methyl-hexanoic acid tert-butyl ester as a white solid (1.95 g, ~100%). $^1$H-NMR; δ (CDCl$_3$), 7.29–7.17 (5H, m), 6.23 (1H, d, J=7.8 Hz), 5.00–4.93 (1H, m), 4.80–4.78 (1H, m), 3.08–3.05 (2H, m), 2.60–2.49 (1H, m), 2.30–2.24 (1H, m).

A solution of 3R-(1S-isopropoxycarbonyl-2-phenyl-ethylcarbamoyl)-5-methyl-hexanoic acid tert-butyl ester (1.95 g, 4.9 mmol) in a 1:1 mixture of TFA:DCM (15 mL) was allowed to stand for 18 hours at room temperature. Solvent and excess TFA were removed under reduced pressure and the residue taken up in toluene and re-evaporated. 3R-(1 S-isopropoxycarbonyl-2-phenyl-ethyl carbamoyl)-5-methyl-hexanoic acid was produced as a colourless oil (1.9 g, contaminated with toluene). $^1$H-NMR; δ (CD1C$_3$) 7.32–7.14 (5H, m), 6.61 (1H, bs), 5.07–4.96 (1H, m), 4.91–4.83 (1H, m), 3.10 (2H, d, J=6.1 Hz), 2.74–2.66 (1H, m), 2.55–2.42 (1H, m), 1.68–1.49 (3H, m), 1.24–1.18 (6H, m) and 0.88 (6H, 2×d).

(C) 2S-(2R-Hydroxycarbamoylmethyl-4-methyl-pentanoylamino)-3-phenyl-propionic acid isopropyl ester.

A solution of 3R-(1S-Isopropoxycarbonyl-2-phenyl-ethylcarbamoyl)-5-methyl-hexanoic acid (1.9 g, 5.23 mmol) was dissolved in DMF (15 mL), cooled in an ice-water bath and treated with HOBT (848 mg, 6.3 mmol) and N-(3-dimethylaminopropyl)-N'-ethylcarbodiimide hydrochloride (1.2 g, 6.3 mmol). After 1 hour a mixture of hydroxylamine hydrochloride (546 mg, 7.9 mmol) and NMM (794 mg, 7.9 mmol) in DMF (10 mL) was added. The reaction was stirred at room temperature for 96 hours. DMF was removed under reduced pressure and the residue partitioned between ethyl acetate and 2M hydrochloric acid. The organic layer was washed with, distilled water, 5% aqueous sodium carbonate and water before drying over magnesium sulfate. The solution was filtered and concentrated under reduced pressure. Recrystallization from diethylether/hexane provided 2S-(2R-hydroxycarbamoylmethyl-4-methyl-pentanoylamino)-3-phenyl-propionic acid isopropyl ester as a white crystalline solid (270 mg, 14%). $^1$H-NMR; δ (methanol-d$_4$), 7.17–7.10 (5H, m), 4.90–4.79 (1H, m), 4.55–4.49 (1H, m), 3.18–2.97 (1H, dd), 2.92–2.85 (1H, dd), 2.78–2.62 (1H, m), 2.02–1.93 (2H, m), 1.48–1.36 (2H, m), 1.11 (3H, d, J=6.3 Hz), 1.02 (3H, d, J=6.3 Hz), 1.00 (1H, m), 0.80 (3H, d, J=6.4 Hz) and 0.76 (3H, d, J=6.4 Hz). $^{13}$C-NMR; δ(methanol-d$_4$) 178.4, 173.8, 171.0, 139.6, 131.7, 130.8, 129.1, 71.4, 56.6, 43.3, 43.2, 41.2, 39.6, 38.3, 33.5, 28.2, 25.1, 23.6, 23.3 and 23.2.

EXAMPLE 8

2S-[2R-(S-Hydroxy-hydroxycarbamoyl-methyl)-4-methyl-pentanoylamine]-3-phenyl-propionic acid isopropyl ester.

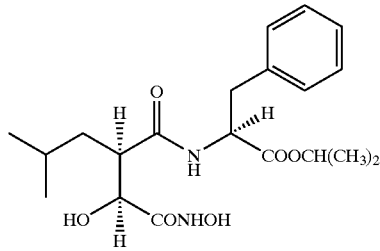

(a) 2S-[2R-(2,2-Dimethyl-5-oso-[1,3]-dioxolan-4S-yl)-4-methyl-pentanoylamino]-3-phenylpropionic acid isopropyl ester.

A solution of 2R-(2,2-dimethyl-5-oxo-[1,3-dioxolan-4S-yl)-4-methyl-pentanoic acid pentafluorophenyll ester (WO 95/19956) (2.87 g, 7.3 mmol) and L-phenylalanine isopropyl ester (1.5 g, 7.3 mmol) in DCM was allowed to stand at room temperature for 96 hours. The reaction mixture was diluted with DCM and washed with 1M aqueous sodium carbonate, 1M hydrochloric acid and brine before drying over magnesium sulphate, filtration and concentration under reduced pressure. The product was recrystallized from ethyl acetate/hexane to yield 2S-[2R-(2,2-dimethyl-5-oxo-[1,3]-dioxolan-4S-yl)-4-methyl-pentanoylamino]-3-phenylpropionic acid isopropyl ester as fine white needles (810 mg, 29%). $^1$H-NMR; δ (CDCl$_3$), 7.35–7.17 (5H, m), 6.38 (1H, d, J=7.5 Hz), 5.06–4.99 (1H, m), 4.88–4.81 (1H, m), 4.50 (1H, d, J=5.9 Hz), 3.13–3.10 (2H, m), 2.73–2.65 (1H, m), 1.71–145 (3H, m), 1.57 (3H, s), 1.54 (3H, s), 1.22 (3H, d, J=6.2 Hz), 1.20 (3H, d, J=6.3 Hz), 0.90 (3H, d, J=6.1 Hz) and 0.88 (3H, d, J=6.2 Hz).

(b) 2S-[2R-(S-Hydroxy-hydroxycarbamoyl-methyl)-4-methyl-pentanoylamine]-3-phenyl-propionic acid isopropyl ester.

A solution of sodium methoxide (325 mg, 6.1 mmol) and hydroxylamine hydrochloride (396 mg, 6.1 mmol) in methanol (15 mL) was stirred at room temperature for 2 hours. The solution was then filtered into a solution of 2S-[2R-(2,2-dimethyl-5-oxo-[1,3]-dioxolan-4S-yl)-4-methyl-pentanoylamino]-3-phenylpropionic acid isopropyl ester (800 mg, 2.1 mmol) in methanol (10 mL). The reaction was allowed to stand at room temperature for 18 hours. The reaction mixture was concentrated under reduced pressure and the residue partitioned between ethyl acetate and water. The organic layer was washed with water, dried over magnesium sulphate, filtered and concentrated under reduced pressure. Recystallization from ethyl acetate gave 2S-[2R-(S-hydroxyhydroxycarbamoyl-methyl)-4-methyl-pentanoylamine]-3-phenyl-propionic acid isopropyl ester as white crystalline material, which was dried, under vacuum (465 mg, 58%). $^1$H-NMR; δ(methanol-d$_4$), 7.17–7.12 (5H, m), 4.83–4.76 (1H, m), 4.53 (1H, t, J=7.2 Hz), 3.88 (1H, d, J=7.1 Hz), 2.95 (2H, d, J=7.1 Hz), 2.78–2.64 (1H, m), 1.55–1.29 (2H, m), 1.09 (3H, d, J=6.3 Hz), 1.08 (1H, m), 0.94 (3H, d, J=6.2 Hz), 0.81 (3H, d, J=6.5 Hz) and 0.76 (3H, d, J=6.5 Hz). $^{13}$C-NMR; δ (methanol-d$_4$), 175.7, 172.5, 171.5, 156.8, 138.0, 130.4, 129.4, 127.8, 73.2, 70.2, 55.4, 49.3, 39.2, 38.6, 26.6, 23.9, 22.1, 21.9 and 21.6.

EXAMPLE 9

2S-[2R-(1S-Hydroxycarbamoyl-ethyl)-4-methyl-pentanoylamino]-3-phenyl-propionic acid isopropyl ester.

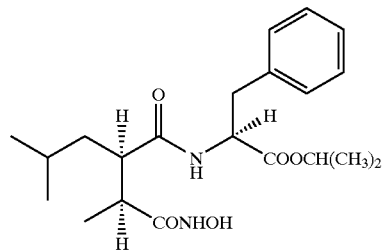

The title compound was prepared using procedures analogous to those described for example 4, starting with 2-benzyloxycarbonyl-3R-isobutyl-succinic acid 1-benzyl ester and L-phenylalanine isopropyl ester. $^1$H-NMR; δ (methanol-d$_4$), 7.18–7.05 (5H, m), 4.94–4.84 (1H, m), 4.65 (1H, dd, J=10.41, 5.0H4, 3.11 (1H, dd, J=14.0, 5.2 Hz), 2.79 (1H, dd, J=13.9, 10.5 Hz), 2.35 (1H, dt, J=11.0, 3.1 Hz), 1.98–1.91 (1H, m), 1.45–1.35 (2H, m), 1.14 (3H, d, J=6.3 Hz), 1.08 (3H, d, J=6.2 Hz), 0.92–0.81 (1H, m), 0.79 (3H, d, J=6.4 Hz), 0.72 (3H, d, J=6.5 Hz) and 0.47 (3H, d, J=6.8 Hz). $^{13}$C-NMR; δ (methanol-d$_4$), 176.5, 160.8, 159.2, 138.4, 130.3, 129.5, 127.8, 70.2, 55.3, 53.5, 49.3, 41.9, 41.7, 36.3, 26.7, 24.5, 22.0, 21.7, 21.7 and 16.5.

EXAMPLE 10

2S-(2R-Hydroxycarbamoylmethyl-octanoylamino)-3-phenyl-propionic acid isopropyl ester.

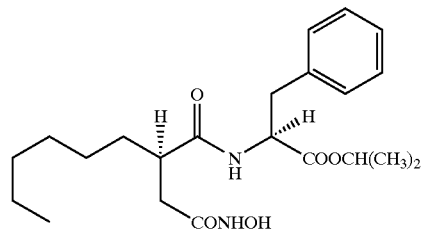

The title compound was prepared using procedures analogous to those described for example 7, starting with 2R-n-hexyl Succinic acid 4-tert-butyl ester and L-phenylalanine isopropyl ester hydrochloride. $^1$H-NMR δ (methanol-d$_4$), 7.19–7.09 (5H, m), 4.85–4.75 (1H, m), 4.50 (1H, dd, J=8.2, 6.9 Hz), 2.99 (1H, dd, J=13.7, 6.7 Hz), 2.86 (1H, dd, J=13.7, 8.3 Hz), 2.68–2.52 (1H, m), 2.03–1.92 (2H, m), 1.48–1.25 (1H, m), 1.16–1.11 (9H, m), 1.10 (3H, d, J=6.3 Hz), 1.01 (3H, d, J=6.3 Hz) and 0.78 (3H, t, J=6.2 Hz). $^{13}$C-NMR; δ (methanol-d$_4$), 177.1, 172.5, 170.4, 138.2, 130.4, 129.5, 127.8, 70.1, 55.4, 43.7, 38.5, 36.4, 33.1, 32.8, 30.4, 28.1, 23.6, 22.0, 21.9 and 14.4.

EXAMPLE 11

2S-[2R-(S-Hydroxy-hydroxycarbamoyl-methyl)-4-methyl-pentanoylamino]-3-phenyl-propionic acid cyclopentyl ester.

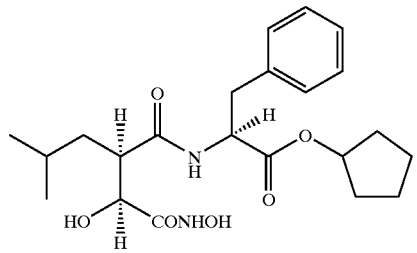

(a) 2S-[2R-(2,2-Dimethyl-5-oxo-[1,3]dioxolan-4S-yl)-4-methyl-pentanoylamino]-3-phenylpropionic acid cyclopentyl ester.

A solution of 2R-(2,2-dimethyl-5-oxo-[1,3-dioxolan-4S-yl)-4-methyl-pentanoic acid pentafluorophenyl ester (WO95/19956) (1.93 g, 4.9 mmol) and L-phenylalanine cyclopentyl ester (1.1 6 g, 5.0 mmol) in ethyl acetate (50 mL) was heated under reflux for 2 hours. The reaction mixture was diluted with ethyl acetate and washed with 1M aqueous sodium carbonate, 1M hydrochloric acid and brine before drying over magnesium sulphate, filtration and concentration under reduced pressure. The product was purified by column chromatography on silica gel eluting with 5% methanol/DCM. Product containing fractions were combined and concentrated under reduced pressure to leave 2S-[2R-(2,2-dimethyl-5-oxo-[1,3]-dioxolan-4S-yl)-4-methyl- pentanoylamino]-3-phenylpropionic acid cyclopentyl ester as a white solid (305 mg, 28%). $^1$H-NMR; δ(CDCl$_3$), 7.32–7.15 (5H, m), 6.42 (1H, d, J=7.5 Hz), 5.21–5.15 (1H, m), 4.87–4.80 (1H, m), 4.50 (1H, d, J=5.9 Hz), 3.11–3.08 (2H, m), 2.73–2.65 (1H, m), 1.83–1.55 (1H, m), 1.58 (3H, s), 1.53 (3H, s), 0.89 (3H, d, J=6.0 Hz) and 0.88 (3H, d, J=6.1 Hz).

(b) 2S-[2R-(S-Hydroxy-hydroxycarbamoyl-methyl)-4-methyl-pentanoylamino]-3-phenyl-propionic acid cyclopentyl ester.

A solution of sodium methoxide (100 mg, 1.9 mmol) in methanol (3 mL) was treated with hydroxylamine hydrochloride (122 mg, 1.9 mmol) and allowed to stir at room temperature for 2 hours. The solution of methanolic hydroxylamine was then filtered into a solution of 2S-[2R-(2,2-dimethyl-5-oxo-[1,3]-dioxolan-4S-yl-4-methyl-pentanoylamino]-3-phenyl-propionic acid cyclopentyl ester in methanol (10 mL). The reaction was allowed to stir at room temperature for 18 hours. The reaction mixture was concentrated under reduced pressure and the residue re-dissolved in ethyl acetate. The solution was washed with 1M hydrochloric acid and brine, dried over magnesium sulfate, filtered and concentrated under reduced pressure. Recrystallization from ethyl acetate/hexane provided 2S-[2R-(S-hydroxy-hydroxycarbamoyl-methyl)-4-methyl-pentanoylamino]-3-phenyl-propionic acid cyclopentyl ester as a white solid (55 mg, 18%). $^1$H-NMR; δ (methanol-d$_4$), 8.23 (1H, d, J=7.3 Hz), 7.20–7.09 (5H, m), 5.99–5.95 (1H, m), 4.53 (1H, dd, J=14.6, 7.3 Hz), 3.88 (1H, d, J=7.0 Hz), 2.94 (2H, d, J=7.4 Hz), 2.73–2.64 (1H, m), 1.80–1.30 (1 0H, m), 1.09–1.01 (1H, m), 0.81 (3H, d, J=6.5 Hz) and 0.76 (3H, d, J=6.4 Hz). $^{13}$C-NMR; δ (methanol-d4), 175.8, 172.8, 171.6, 138.0, 130.4, 129.5, 127.9, 79.6, 73.2, 55.4, 49.2, 39.1, 38.7, 33.5, 26.7, 24.6, 24.0 and 22.1.

EXAMPLE 12

2S-(3S-Hydroxycarbamoyl-2R-isobutyl-hex-5-enoylamino)-3S-methyl-pentanoic acid cyclopentyl ester.

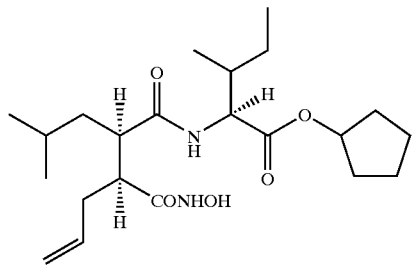

(a) N-Benzyloxycarbonyl-L-isoleucine cyclopentyl ester.

A solution of N-benzyloxycarbonyl-L-isoleucine (10.0 g, 37.7 mmol) in DCM (150 mL) was treated with N-(3-dimethylaminopropyl)-N'-ethylcarbodiimide hydrochloride (7.94 g, 41.5 mmol), cyclopentanol (3.90 g, 45.2 mmol) and N,N-dimethylaminopyridine (20 mg). The reaction was allowed to stand at room temperature for 18 hours. The reaction mixture was washed with 1M hydrochloric acid, saturated sodium bicarbonate, and brine before drying over magnesium sulphate, filtration and removal of solvent under reduced pressure to leave N-benzyloxycarbonyl-L-isoleucine cyclopentyl ester as a colorless oil (10.99 g, 87%). $^1$H-NMR; δ (CDCl$_3$) 7.44–7.30 (5H, m), 5.37–5.34 (1H, m), 5.22–5.18 (1H, m), 5.11 (2H, s), 4.33–4.27 (1H, m), 1.90–1.55 (10H, m), 1.51–135 (1H, m), 1.28–1.20 (2H, m), 0.93 (3H, d, J 6.9 Hz) and 0.91 (3H, d, J=7.0 Hz).

(b) 2S-(3S-Hydroxycarbamoyl-2R-isobutyl-hex-5-enoylamino)-3S-methyl-pentanoic acid cyclopentyl ester.

N-Benzyloxycarbonyl-L-isoleucine cyclopentyl ester was converted to the title compound using chemistry analogous to that described for example 6. $^1$H-NMR; 67 (methanol-d$_4$), 8.40 (1H, d, J=7.9 Hz), 5.64–5.47 (1H, m), 5.09–5.04 (1H, m), 4.93–4.85 (2H, m), 4.25–4.19 (1H, m), 2.56–2.49 (1H, m), 2.24–2.04 (2H, m), 1.98–1.88 (1H, m), 1.79–1.18 (12H, m), 1.22–1.10 (1H, m), 1.00–0.96 (1H, m) and 0.95–0.73 (12H, m). $^{13}$—C NMR; δ (methanol-d$_4$), 176.6, 172.6, 172.4, 165.9, 142.3, 136.0, 117.5, 79.3, 58.5, 47.7, 41.7, 37.9, 33.5, 26.8, 26.5, 24.6, 24.5, 21.8, 16.0 and 11.4.

EXAMPLE 13

2S-(3S-Hydroxycarbamoyl-2R-isobutyl-hex-5-enoylamino)-3-phenylpropionic acid 2-methoxy-ethyl ester.

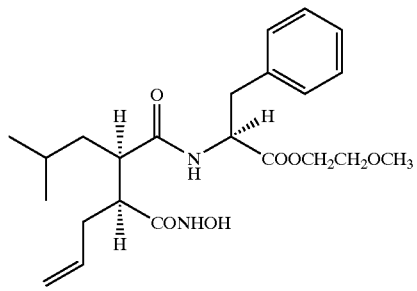

(a) N-(carbobenzyloxy)-L-phenylalanine 2-methoxy-ethyl ester.

A solution of N-(carbobenzyloxy)-L-phenylalanine (10.0 g, 33.4 mmol) in DMF (75 mL) was treated with HOBT (6.8 g, 50.1 mmol), N-(3-dimethylaminopropyl)-N'-ethylcarbodiimide hydrochloride (7.7 g, 40.1 mmol), 2-methoxyethanol (2.8 g, 36.8 mmol) and a catalytic amount of 4-N,N-dimethylaminopyridine. The reaction was stirred overnight at room temperature. The reaction mixture was concentrated under reduced pressure and the residue taken up in ethyl acetate and washed with 1M hydrochloric acid, saturated sodium hydrogen carbonate and brine. The solution was dried over sodium sulphate, filtered and concentrated under reduced pressure to provide N-(carbobenzyloxy)-L-phenylalanine 2-methoxy-ethyl ester as a yellow foam (8.8 g, 74%). $^1$H-NMR; δ (CDCl$_3$), 7.44–7.12 (10H, m), 5.27 (1H, d), 5.11 (2H, s), 4.72 (1H, dd), 4.26 (2H, m), 3.57 (2H, t), 3.38 (3H, s) and 3.15 (2H, m).

(b) L-Phenylalanine 2-methoxy-ethyl ester.

A solution of N-(carbobenzyloxy)-L-phenylalanine 2-methoxy-ethyl ester (4.4 g, 12.3 mmol) in ethanol (75 mL) was treated with palladium on charcoal catalyst (440 mg, 10% Pd on charcoal) as a slurry in ethyl acetate (10 mL). Hydrogen gas was passed through the suspension for 3 hours. The reaction mixture was filtered and concentrated under reduced pressure to provide L-phenylalanine 2-methoxy-ethyl ester as a colorless oil (2.5 g, 92%). $^1$H-NMR; d (methanol-d$_4$), 7.35–7.20 (5H, m), 4.27 (2H, m), 3.79 (1H, m), 3.57 (2H, m), 3.38 (3H, s), 3.10 (1H, dd), 2.90 (1H, dd) and 1.64 (2H, s).

(c) 2S-{1R-[1S-(2-Methoxy-ethoxycarbonyl)-2-phenyl-ethylcarbamoyl]-3-methyl-butyl}-pent-4-enoic acid tert-butyl ester.

A solution of L-phenylalanine 2-methoxy-ethyl ester (910 mg, 4.1 mmol) in DMF (15 mL) was treated with 3S-tert-butoxycarbonyl-2R-isobutyl-hex-5-enoic acid (1.0 g, 3.7 mmol), HOBT (750 mg, 5.6 mmol), N-(3-dimethylaminopropyl)-N'-ethylcarbodiimide hydrochloride (850 mg, 4.4 mmol) and NMM (560 mg, 5.6 mmol). The reaction was stirred overnight at room temperature. The reaction mixture was concentrated under reduced pressure and the residue taken up in ethyl acetate. The solution was washed with 1M hydrochloric acid, saturated sodium hydrogen carbonate and brine. The solution was dried over sodium sulfate, filtered and concentrated under reduced pressure. The product was purified by column chromatography, eluting with 1–2% methanol/DCM. Product-containing fractions were combined and concentrated under reduced pressure to provide 2S-{1R-[1S-(2-methoxy-ethoxycarbonyl)-2-phenyl-ethylcarbamoyl]-3-methyl-butyl}-pent-4-enoic acid tert-butyl ester as an off-white gum (1.0 g, 58%). $^1$H-NMR; δ (CDCl$_3$), 7.32–7.17 (5H, m), 6.00 (1H, d), 5.65 (1H, m), 4.98 (3H, m), 4.28 (2H, m), 3.56 (2H, m), 3.38 (3H, s), 3.20 (1H, dd), 3.07 (1H, dd), 2.45 (1H, m), 2.35 (1H, m), 1.97 (1H, m), 1.65 (1H, m), 1.49 (1H, m), 1.42 (9H, s), 1.06 (1H, m) and 0.85 (6H, 2xd).

(d) 2S-(3S-Hydroxycarbonyl-2R-isobutyl-hex-5-enoylamino)-3-phenylpropionic acid 2-methoxy-ethyl ester.

A solution of 2S-{1R-[1S-(2-methoxy-ethoxycarbonyl)-2-phenyl-ethylcarbamoyl]-3-methyl-butyl}-pent-4-enoic acid tert-butyl ester (1.0 g, 2.1 mmol) in a mixture of TFA and DCM (1:1, 6 mL) was allowed to stand at 5° C. overnight. The reaction mixture was concentrated under reduced pressure and azeotroped with toluene. Crystallization of the product from ethyl acetate/hexane gave 2S-(3S-hydroxycarbonyl-2R-isobutyl-hex-5-enoylamino)-3- phenylpropionic acid 2-methoxy-ethyl ester as a white solid (387 mg, 44%). ¹H-NMR; δ (CDCl₃), 7.33–7.13 (5H, m), 6.22 (1H, d), 5.65 (1H, m), 5.08–4.94 (3H, m), 4.38–4.24 (2H, m), 3.61 (2H, m), 3.40 (3H, s), 3.26 (1H, dd), 3.09 (1H, dd), 2.55 (1H, m), 2.41 (2H, m), 2.03 (1H, m), 1.66 (1H, dt), 1.49 (1H, m), 1.16 (1H, m) and 0.86 (6H, 2xd).

(e) 2S-(3S-Hydroxycarbamoyl-2R-isobutyl-hex-5-enoylamino)-3-phenylpropionic acid 2-methoxy-ethyl ester.

A solution of 2S-(3S-hydroxycarbonyl-2R-isobutyl-hex-5-enoylamino)-3-phenylpropionic acid 2-methoxy-ethyl ester (375 mg, 0.9 mmol) in DMF (5 mL) was cooled in an ice/water bath. N-(3-Dimethylaminopropyl)-N'-ethylcarbodiimide hydrochloride (205 mg, 117 mmol) and HOBT (145 mg, 1.1 mmol) were added with stirring. After 2 hours at this temperature, a solution of hydroxylamine hydrochloride (93 mg, 1.3 mmol) and NMM (136 mg, 1.3 mmol) in DMF (5 mL) was added. The reaction was allowed to warm to room temperature and stirred overnight. The reaction mixture was concentrated under reduced pressure and the residue partitioned between ethyl acetate and water. The organic phase was washed with 5% aqueous sodium carbonate and water, dried over sodium sulphate, filtered and concentrated under reduced pressure. The product was recrystallized from ethyl acetate/hexane to yield 2S-(3S-hydroxycarbamoyl-2R-isobutyl-hex-5-enoylamino)-3-phenylpropionic acid 2-methoxy-ethyl ester as a white solid (185 mg, 48%). ¹H-NMR; δ (methanol-d₄), 7.20–7.05 (5H, m), 5.33 (1H, m), 4.79–4.67 (4H, m), 4.15 (2H, m), 3.48 (2H, m), 3.25 (3H, s), 3.15 (1H, m), 2.80 (1H, dd, J=10.9, 13.9 Hz), 2.37 (1H, dt, J=11.1, 3.2 Hz), 1.90 (1H, dt, J=11.4, 3.4 Hz), 1.77 (1H, m), 1.44–1.18 (3H, bm), 0.91 (1H, m), 0.79 (3H, d, J=6.4 Hz) and 0.72 (3H, d, J=6.5 Hz). ¹³C-NMR; δ (methanol-d₄) 176.4, 172.8, 172.4, 138.3, 136.1, 130.3, 129.5, 128.0, 117.3, 71.3, 65.2, 59.1, 55.0, 47.9, 41.6, 38.2, 35.7, 26.6, 24.6 and 21.6.

EXAMPLE 14

2S-[2R-(1S-Hydroxycarbamoyl-ethyl)-4-methyl-pentanoylamino]-3-phenyl-propionic acid 2-methoxy-ethyl ester.

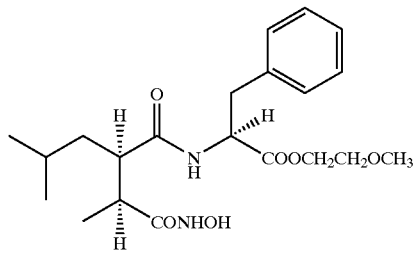

(a) 2-{1R-[1S-(2-Methoxy-ethoxycarbonyl)-2-phenyl-ethylcarbamoyl] 3-methyl-butyl}-malonic acid dibenzyl ester.

A solution of 2-benzyloxycarbonyl-3R-isobutyl succinic acid 1-benzyl ester (4.06 g, 10.2 mmol), L-phenylalanine 2-methoxy-ethyl ester (see Example 13, 2.50 g, 11.2 mmol), HOBT (2.06 g, 15.3 mmol), N-methylmorpholine (1.54 g, 15.3 mmol) and N-(3-dimethylaminopropyl)-N'-ethylcarbodiimide hydrochloride (2.34 g, 12.2 mmol) in DMF (25 mL) was stirred at room temperature for 18 hours. The reaction mixture was concentrated under reduced pressure, the residue taken up in ethyl acetate and washed with 1M citric acid, saturated sodium hydrogen carbonate and brine. The solution was dried with sodium sulphate, filtered and concentrated under reduced pressure. The product was purified by column chromatography, eluting with 2–3% methanol/DCM. Product-containing fractions were combined and concentrated under reduced pressure to provide 2-{1R-[1S-(2-methoxy-ethoxycarbonyl)-2-phenyl-ethylcarbamoyl]-3-methyl-butyl}-malonic acid dibenzyl ester (4.89 g, 80%). ¹H NMR; δ (CDCl₃), 7.39–7.13 (15H, bm), 6.30 (1H, d), 5.13 (3H, m), 4.90 (1H, m), 4.23 (2H, m), 3.86 (1H, d), 3.48 (3H, m), 3.35 (3H, s), 3.14 (1H, dd), 2.96 (2H, m), 1.68–1.45 (2H, m), 1.00 (1H, m), 0.78 (3H, d) and 0.77 (3H, d).

(b) 2-{1R-[1S-(2-Methoxy-ethoxycarbonyl)-2-phenyl-ethylcarbamoyl]-3-methyl-butyl}-acrylic acid.

A solution of 2-{1R-[1S-(2-methoxy-ethoxycarbonyl)-2-phenyl-ethylcarbamoyl]-3-methyl-butyl}-malonic acid dibenzyl ester (4.88 g, 8.1 mmol) in ethanol (25 mL) was treated with palladium catalyst (490 mg, 10%Pd/charcoal) as a slurry in ethyl acetate (5 mL). Hydrogen gas was passed through the suspension for 2 hours. The reaction mixture was filtered and treated with piperidine (830 mg, 9.7 mmol) and formaldehyde (as a 37 weight percent solution in water, 0.79 mL, 9.7 mmol). The solution was allowed to stand at room temperature for 18 hours. The reaction mixture was concentrated under reduced pressure and the residue resuspended in ethyl acetate. The solution was washed with saturated sodium hydrogen carbonate. The aqueous phase was acidified to pH 1 with 1M hydrochloric acid and extracted with ethyl acetate. The organic phase was dried over sodium sulphate, filtered and concentrated under reduced pressure to provide 2-{1R-[1S-(2-methoxy-ethoxycarbonyl)-2-phenyl-ethylcarbamoyl]-3-methyl-butyl}-acrylic acid as a waxy white solid (2.21 g, 70%). ¹HNMR; δ (CDCl₃), 7.27–7.06 (5H, bm), 6.50 (1H, d), 6.43 (1H, s), 5.85 (1H, s), 4.92 (1H, m), 4.29 (2H, m), 3.59 (2H, t), 3.48 (1H, m), 3.39 (3H, s), 3.12 (2H, m), 1.79 (1H, m), 1.51 (2H, m), 0.90 (3H, d) and 0.87 (3H, d).

(c) 3R-[1S-(2-Methoxy-ethoxycarbonyl)-2-phenyl-ethylcarbamoyl]-2S,5-dimethyl-hexanoic acid.

A solution of 2-{1R-[1S-(2-methoxy-ethoxycarbonyl)-2-phenyl-ethylcarbamoyl]-3-methyl-butyl-acrylic acid (2.21 g, 5.65 mmol) in ethanol (40 mL) was treated with palladium catalyst (220 mg, 10%Pd/charcoal) as a slurry in ethyl acetate (5 mL). Hydrogen gas was passed through the suspension for 4 hours. The reaction mixture was filtered and concentrated under reduced pressure to provide 3R-[1S-(2-methoxy-ethoxycarbonyl)-2-phenyl-ethylcarbamoyl}-2S,5-dimethyl-hexanoic acid (1.96 g, 88%). ¹H NMR; δ (CDCl₃), 7.31–7.14 (5H, m), 6.49 (1H, d), 5.55 (1H, bs), 4.98 (1H, m), 4.27 (2H, m), 3.57 (2H, m), 3.37 (3H, s), 3.19 (1H, dd), 3.07 (1H, m), 2.57 (1H, t), 2.44 (1H, m), 1.71–142 (2H, m), 1.11 (1H, m), 1.00 (2H, d), 0.85 (3H, d) and 0.84 (3H, d).

(d) 2S-[2R-(1S-Benzyloxycarbamoyl-ethyl)-4-methyl-pentanoylamino]-3-phenyl-propionic acid 2-methoxy-ethyl ester.

A solution of 3R-[1S-(2-methoxy-ethoxycarbonyl)-2-phenyl-ethylcarbamoyl}-2S,5-dimethyl-hexanoic acid (1.96 g, 5.0 mmol) in DMF (30 mL) was treated with HOBT (810 mg, ~6.0 mmol), O-benzylhydroxylamine-(740 mg, ~6.0 mmol) and N-(3-dimethylaminopropyl)-N'-ethylcarbodiimide hydrochloride (1.15 g, 6.0 mmol) and stirred at ambient temperature for 48 hours. The reaction mixture was concentrated under reduced pressure and the residue dissolved in ethyl acetate. The solution was washed with 1M hydrochloric acid, saturated sodium hydrogen carbonate and brine. The solution was dried with sodium sulphate, filtered and concentrated under reduced pressure. The product was recrystallized from ethyl acetate/hexane to provide 2S-[2R-(1S-benzyloxycarbamoyl-ethyl)-4-methyl-pentanoylamino]-3-phenyl-propionic acid 2-methoxy-ethyl ester as a white solid (1.63 g, 66%). $^1$H NMR; δ (CDCl$_3$), 9.21 (1H, s), 7.41–7.14 (10H, m), 6.37 (1H, d), 4.91 (3H, s), 4.27 (2H, m), 3.56 (2H, t), 3.36 (3H, s), 3.18 (1H, dd), 3.05 (1H, dd), 2.44 (1H, m), 2.18 (1H, m), 1.78 (1H, s), 1.47 (2H, m), 1.04 (1H, m), 0.85 (3H, d and 0.81 (3H, d).

(e) 2S-[2R-(1S-Hydroxycarbamoyl-ethyl)-4-methyl-pentanoylamino]-3-phenyl-propionic acid 2-methoxy-ethyl ester.

A solution of 2S-[2R-(1S-benzyloxycarbamoyl-ethyl)-4-methyl-pentanoylamino]-3-phenyl-propionic acid 2-methoxy-ethyl ester (1.62 g, 3.3 mmol) in ethanol (30 mL) was treated with palladium catalyst (160 mg, 1 0%Pd/charcoal as a slurry in ethyl acetate (5 mL). Hydrogen gas was passed through the suspension for 2 hours. The reaction mixture was filtered and concentrated under reduced pressure. The product was recrystallized from ethyl acetate/hexane to provide 2S-[2R-(1S-hydroxycarbamoyl-ethyl)-4-methyl-pentanoylamino]-3-phenyl-propionic acid 2-methoxy-ethyl ester as a white solid (942 mg, 71%). $^1$H-NMR; δ (methanol-d$_4$), 7.16–7.06 (5H, m), 4.70 (1H, m), 4.14 (2H, t, J=4.7 Hz), 3.47 (2H, m), 3.25 (3H, s), 3.18 (1H, m), 2.82 (1H, dd, J=10.5, 13.9 Hz), 2.34 (1H, m), 1.94 (1H, m), 1.40 (2H, m), 0.89 (1H, m), 0.89 (1H, m), 0.78 (3H, d, J=6.4 Hz), 0.72 (3H, d, J=6.4 Hz) and 0.48 (3H, d, J=6.8 Hz). $^{13}$C-NMR; δ (methanol-d$_4$), 176.6, 174.4, 172.8, 138.4, 130.3, 129.5, 127.8, 78.8, 71.3, 65.2, 59.1, 55.1, 48.6, 42.0, 41.7, 36.3, 26.8, 24.6, 21.7 and 16.5.

EXAMPLE 15

2S-(3S-Hydroxycarbamoyl-2R-isobutyl-hexanoylamino)-3,3-dimethyl-butyric acid 2-methoxy-ethyl ester.

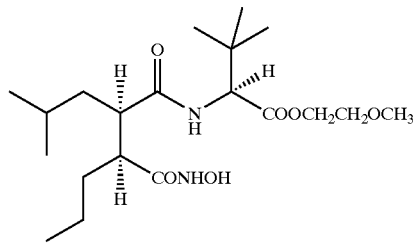

(a) 2S-{1R-[1S-(2-Methoxy-ethoxycarbonyl)-2,2-dimethyl-propylcarbamoyl]-3-methyl-butyl}-pent-4-enoic acid tert-butyl ester.

L-tert-Leucine 2-methoxy-ethyl ester (840 mg, 4.4 mmol), which had been prepared in a similar way to L-phenylalanine 2-methoxy-ethyl ester (example 13) was dissolved in DMF (15 mL). This solution was treated with 3S-tert-butoxycarbonyl-2R-isobutyl-hex-5-enoic acid (1.09 g, 4.0 mmol), HOBT (820 mg, 6.1 mmol), NMM (610 mg, 6.1 mmol) and N-(3-dimethylaminopropyl)-N'-ethylcarbodiimide hydrochloride (930 mg, 4.9 mmol) and stirred at ambient temperature for 18 hours. The reaction mixture was concentrated under reduced pressure and the residue taken up in ethyl acetate. The solution was washed with 1M hydrochloric acid, saturated sodium hydrogen carbonate and brine. The organic phase was dried with sodium sulphate, filtered and concentrated under reduced pressure. The product was purified by column chromatography, eluting with 1% methanol/DCM. Product-containing fractions were combined and concentrated under reduced pressure to provide 2S-{1R-[1S-(2-methoxy-ethoxycarbonyl)-2,2-dimethyl-propylcarbamoyl]-3-methyl-butyl}-pent-4-enoic acid tert-butyl ester as an off-white solid (1.02 g, 57%). $^1$H NMR; δ(CDCl$_3$), 6.14 (1H, d), 5.73 (1H, m), 5.04 (2H, m), 4.48 (1H, d), 4.28 (2H, m), 3.59 (2H, t), 3.36 (3H, s), 2.49 (3H, m), 2.26 (2H, m), 1.68 (1H, m), 1.47 (9H, m), 1.12 (2H, m), 1.09 (9H, s) 0.90 (3H, d) and 0.86 (3H, d).

(b) 2S-{1R-[1S-(2-Methoxy-ethoxycarbonyl)-2,2-dimethyl-propylcarbamoyl]-3-methyl-butyl}-pent-4-enoic acid.

A solution of 2S-{1R-[1S-(2-methoxy-ethoxycarbonyl)-2,2-dimethyl-propyl-carbamoyl]-3-methyl-butyl}-pent-4-enoic acid tert-butyl ester (1.00 g, 2.3 mmol) in a mixture of TFA and DCM (1:1, 6 mL) was allowed to stand at 5° C. overnight. The reaction mixture was concentrated under reduced pressure and azeotroped with ethyl acetate and toluene to leave 2S-{1R-[1S-(2-methoxy-ethoxycarbonyl)-2,2-dimethyl-propylcarbamoyl]-3-methyl-butyl-pent-4-enoic acid as a yellow gum (870 mg, quantitative). $^1$H-NMR; δ (methanol-d$_4$), 8.21 (1H, d), 5.64 (1H, m), 4.92 (3H, m), 4.26 (1H, d), 4.14 (2H, m), 3.49 (2H, m), 3.24 (3H, s), 2.67 (1H, m), 2.44 (1H, m), 2.16 (3H, m), 1.60–1.32 (3H, m), 1.02 (1H, m), 0.91 (9H, m) and 0.77 (6H, m).

(c) 2S-(3S-Benzyloxycarbamoyl-2R-isobutyl-hex-5-enoylamino)-3,3-dimethyl-butyric acid 2-methoxy-ethyl ester.

A solution of 2S-{1R-[1S-(2-methoxy-ethoxycarbonyl)-2,2-dimethyl-propyl-carbamoyl]-3-methyl-butyl}-pent-4-enoic acid (463 mg, 1.2 mmol) in DMF (5 mL) was treated with HOBT (195 mg, 1.4 mmol), N-(3-dimethylaminopropyl)-N'-ethylcarbodiimide hydrochloride (276 mg, 1.4 mmol) and O-benzylhydroxylamine (177 mg, 1.4 mmol). The reaction was stirred at ambient temperature for 18 hours. The reaction mixture was concentrated under reduced pressure and taken up in ethyl acetate. The solution was washed with 1M hydrochloric acid, saturated sodium hydrogen carbonate and brine. The organic phase was dried with sodium sulphate, filtered and concentrated under reduced pressure. The product was recrystallized from ethyl acetate/hexane to provide 2S-(3S-benzyloxycarbamoyl-2R-isobutyl-hex-5-enoylamino)-3,3-dimethyl-butyric acid 2-methoxy-ethyl ester as a white solid (106 mg, 18%). $^1$H NM R; δ (CDCl$_3$), 9.03 (1H, s), 7.42–7.34 (5H, m), 6.26 (1H, d), 5.65 (1H, m), 4.97 (4H, m), 4.42 (1H, d), 4.28 (2H, m), 3.58 (2H, t), 3.35 (3H, s), 2.57–2.26 (4H, m), 1.47 (2H, m), 1.11 (1H, m), 1.00 (9H, m), 0.89 (3H, d) and 0.83 (3H, d).

(d) 2S-(3S-Hydroxycarbamoyl-2R-isobutyl-hexanoylamino)-3,3-dimethyl-butyric acid 2-methoxy-ethyl ester.

A solution of 2S-(3S-benzyloxycarbamoyl-2R-isobutyl-hex-5-enoylamino)-3,3-dimethyl-butyric acid 2-methoxy-ethyl ester (95 mg, 0.2 mmol) in ethanol (20 mL) was treated with palladium catalyst (10 mg, 10%Pd/charcoal) as a slurry in ethyl acetate (3 mL). Hydrogen gas was passed through the suspension for 4 hours. The reaction mixture was filtered and concentrated under reduced pressure. The product was purified by preparative HPLC using a C18 silica column, eluting with 70% methanol/30% water (Containing 0.1% TFA). Product-containing fractions were combined and concentrated under reduced pressure. The product was dissolved in DCM and washed with saturated sodium hydrogen carbonate. The organic solution was dried with sodium sulphate, filtered and concentrated under reduced pressure to provide 2S-(3S-hydroxycarbamoyl-2R-isobutyl-hexanoylamino)-3,3-dimethyl-butyric-acid 2-methoxy-ethyl ester as a white solid (40 mg, 52%). $^1$H-NMR; δ (methanol-d$_4$), 8.28 (1H, d, J=8.7 Hz), 4.27 (1H, d, J=8.8 Hz), 4.14 (2H, m), 3.49 (2H, t, J=4.7 Hz), 3.24 (3H, s), 2.57 (1H, dt, J=10.9, 3.1 Hz), 2.07 (1H, m), 1.50–0.99 (7H, bm), 0.95 (9H, s) and 0.91–0.72 (9H, m). $^{13}$C-NMR; δ (methanol-d$_4$), 177.0, 173.2, 172.2, 71.4, 64.6, 62.6, 62.5, 58.9, 47.9, 47.8, 41.8, 34.9, 34.3, 27.3, 26.8, 24.5, 21.8, 21.5 and 14.3.

EXAMPLE 16

2S-[2R-(S-Hydroxycarbamoyl-methoxy-methyl)-4-methyl-pentanoylamino]-3-phenyl-propionic acid isopropyl ester.

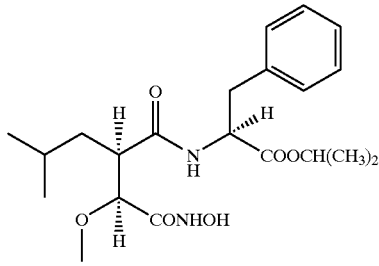

(a) 2R-(S-Benzyloxycarbamoyl-methoxy-methyl)-4-methyl-pentanoic acid.

A solution of 3R-isobutyl-4S-methoxy-dihydrofuran-2,5-dione (WO 97/02239) (609 mg, 3.27 mmol), and O-benzylhydroxylamine (403 mg, 3.27 mmol) in ethyl acetate (5 mL) was stirred at room temperature for 1 hour. The reaction mixture was concentrated under reduced pressure to provide 2R-(S-benzyloxycarbamoyl-methoxy-methyl)-4-methyl-pentanoic acid as a white foam (1.01 g, 100%). $^1$H NMR; δ (CDCl$_3$), 7.43–7.36 (5H, m), 5.00–4.89 (2H, m), 3.90 (1H, d, J=6.0 Hz), 3.34 (3H, s), 2.91–2.84 (1H, m), 1.74–1.65 (2H, m), 1.35–1.24 (1H, m), 0.94–0.89 (6H, 2xd).

(b) 2S-[2R-(S-Benzyloxycarbamoyl-methoxy-methyl)-4-methyl-pentanoylamino]-3-phenyl-propionic acid isopropyl ester.

A solution of 2R-(S-benzyloxycarbamoyl-methoxy-methyl)-4-methyl-pentanoic acid (1.01 g, 3.3 mmol) in tetrahydrofuran (15 mL) at 0° C. was treated with L-phenylalanine isopropyl ester (81 0 mg, 3.9 mmol) and N-(3-dimethylaminopropyl)-N'-ethylcarbodiimide hydrochloride (750 mg, 3.9 mmol). The reaction mixture was allowed to warm to ambient temperature and stirred for 18 hours. The solution was concentrated under reduced pressure and the residue taken up in DCM. This solution was washed with 1M hydrochloric acid, saturated sodium hydrogen carbonate and brine. The organic phase was dried with sodium sulphate, filtered and concentrated under reduced pressure. The product was purified by column chromatography, eluting with 2% methanol/DCM. Product-containing fractions were combined and concentrated under reduced pressure to provide 2S-[2R-(S-benzyloxycarbamoyl-methoxy-methyl)-4-methyl-pentanoylamino]-3-phenyl-propionic acid isopropyl ester as a white solid (1.39 g, 85%). $^1$H NMR; δ (methanol-d$_4$), 7.35–7.08 (1OH, m), 4.83 (1H, m), 4.79 (2H, s), 4.58 (1H, m), 3.32 (1H, d), 3.00 (1H, m), 2.94 (3H, s), 2.86 (1H, m), 2.59 (1H, m), 1.36 (2H, m), 1.14 (1H, m), 1.07 (6H, dd), 0.77 (3H, d) and 0.72 (3H, d).

(c) 2S-[2R-(S-Hydroxycarbamoyl-methoxy-methyl)-4-methyl-pentanoylamino]-3-phenyl-propionic acid isopropyl ester.

A solution of 2S-[2R-(S-benzyloxycarbamoyl-methoxy-methyl)-4-methylpentanoylamino]-3-phenyl-propionic acid isopropyl ester (1.37 g, 2.8 mmol) in ethanol (30 mL) was treated with palladium catalyst (274 mg, 10%Pd/charcoal) as a slurry in ethyl acetate (5 mL). Hydrogen gas was passed through the suspension for 2 hours. The reaction mixture was filtered and concentrated under reduced pressure. The product was recrystallized from ethyl acetate/hexane to provide 2S-[2R-(S-hydroxycarbamoyl-methoxy-methyl)-4-methyl-pentanoylamino]-3-phenyl-propionic acid isopropyl-ester as a white solid (778 mg, 70%). $^1$H-NMR; δ (methanol-d$_4$), 7.12 (5H, m), 4.85 (1H, m), 4.59 (1H, dd, J=8.2, 6.2 Hz), 3.39 (1H, d, J=9.7 Hz), 3.02 (3H, s), 2.92 (2H, m), 2.63 (1H, dt, J=11.1, 3.4 Hz), 1.44 (2H, m), 1.11 (3H, d, J=6.2 Hz), 1.03 (3H, d, J=6.3 Hz), 0.87 (1H, m), 0.80 (3H, d, J=6.4 Hz) and 0.75 (3H, d, J=6.4 Hz), $^{13}$C-NMR; δ (methanol-d$_4$), 175.3, 172.4, 169.4, 138.2, 130.3, 129.4, 127.7, 82.8, 70.1, 58.0, 55.4, 48.7, 38.4, 26.5, 24.3, 22.0, 21.9 and 21.8.

EXAMPLE 17

2S-{2R-[1S-Hydroxycarbamoyl-2-(thiophen-2-ylsulphanyl)-ethyl]-4-methyl-pentanoylamino}-3-phenyl-propionic acid isopropyl ester.

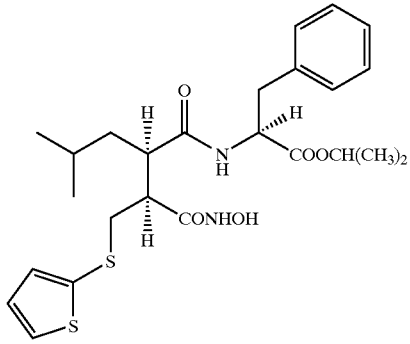

(a) 3R-(1S-I-sopropoxycarbonyl-2-phenyl-ethylcarbamoyl)-5-methyl-2S-(thiophen-2-ylsulphanylmethyl)-hexanoic acid.

A solution of 2-[1R-(1S-isopropoxycarbonyl-2-phenyl-ethylcarbamoyl)-3-methyl-butyl]-acrylic acid (intermediate in example 5) (1.67 g, 4.5 mmol) in propan-2-ol(5 mL) was treated with 2-mercaptothiophene (1.03 g, 8.9 mmol). The reaction mixture was heated at 60° C. in the dark for 72 hours. The solution was concentrated under reduced pressure. The product was purified by column chromatography, eluting with 1% methanol/DCM. Product-containing fractions were combined and concentrated under reduced pressure to provide 3R-(1S-isopropoxycarbonyl-2-phenyl-ethylcarbamoyl)-5-methyl-2S-(thiophen-2-ylsulphanyl-methyl)-hexanoic acid as an off-white foam (1.08 g, 49%). $^1$H NMR; δ (CDCl$_3$), 7.36–7.27 (4H, m), 7.18 (2H, m), 7.05 (1H, m), 7.00 (1H, m), 6.35 (1H, d), 5.07 (1H, m), 4.85 (1H, m), 3.23 (2H, m), 3.08 (1H, dd), 2.79–2.59 (3H, m), 1.59 (2H, m), 1.25 (6H, t), 1.17 (1H, m) and 0.86 (6H, 2xd).

(b) 2S-{2R-[1S-Hydroxycarbamoyl-2-(thiophen-2-ylsulphanyl)-ethyl]-4-methyl-pentanoylamino}-3-phenyl-propionic acid isopropyl ester.

A solution of 3R-(1S-isopropoxycarbonyl-2-phenyl-ethylcarbamoyl)-5-methyl-2S-(thiophen-2-ylsulphanylmethyl)-hexanoic acid (1.06 g, 2.2 mmol) in DMF (6 mL) was treated with HOBT (350 mg, 2.6 mmol) and N-(3-dimethylaminopropyl)-N'-ethylcarbodiimide hydrochloride (497 mg, 2.6 mmol). The solution was stirred in an ice/water bath for 2 hours and then treated with a pre-mixed solution of hydroxylamine hydrochloride (225 mg, 3.2 mmol) and NMM (328 mg, 3.2 mmol) in DMF (5 mL). The reaction mixture was stirred at ambient temperature for 96 hours. The solution was concentrated under reduced pressure and the residue taken up in ethyl acetate and partitioned with water. The organic phase was washed with 0.5M sodium carbonate and water, dried with sodium sulphate, filtered and concentrated under reduced pressure. The product was recrystallized from ethyl acetate/hexane to provide 2S-{2R-[1S-hydroxy-carbamoyl-2-(thiophen-2-ylsulphanyl)-ethyl]-4-methyl-pentanoyl-amino}-3-phenyl-propionic acid isopropyl ester as a white solid (707 mg, 65%). $^1$H-NMR; δ (methanol-$d_4$), 7.29 (1H, dd, J=1.5, 5.0 Hz), 7.13 (5H, m), 6.89–6.83 (2H, m), 4.88 (1H, m), 4.61 (1H, dd, J=4.6, 11.0 Hz), 3.12 (1H, dd, J=4.6, 13.9 Hz), 2.74 (1H, dd, J=11.1, 13.9 Hz), 2.33 (2H, m), 2.13 (1H, m), 1.90 (1H, dd, J=3.3, 13.2 Hz), 1.42–1.33 (2H, m), 1.14 (3H, d, J=6.3 Hz), 1.10 (3H, d, J=6.2 Hz), 0.90 (1H, m), 0.78 (3H, d, J=6.4 Hz) and 0.72 (3H, d, J=6.5 Hz). $^{13}$C-NMR; δ (methanol-d4), 175.4, 172.3, 171.0, 138.2, 134.3, 130.1, 129.6, 128.5, 128.2, 70.3, 55.2, 47.9, 47.8, 41.6, 39.0, 38.2, 26.4, 24.4, 21.9 and 21.6.

EXAMPLE 18

2S-[2R-(1S-Hydroxycarbamoyl-ethyl)-4-methyl-pentanoylamino]-3,3-dimethyl-butyric acid 2-methoxy-ethyl ester.

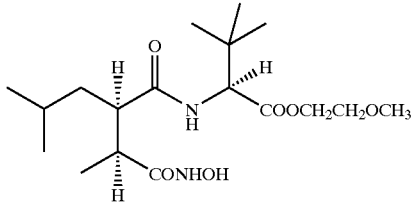

The title compound was prepared using an analogous route to that described for example 14 replacing L-phenylalanine with L-tert-leucine. $^1$H-NMR; δ (methanol-$d_4$), 4.26 (1H, s), 4.14 (2H, m), 3.50 (2H, m), 3.24 (3H, s), 2.60 (1H, dt, J=1 0.8, 3.2 Hz), 2.15 (1H, m), 1.49–1.19 (3H, m), 0.98 (3H, s), 0.95 (9H, s), 0.81 (3H, d, J=6.4 Hz) and 0.73 (3H, dd, J=6.5 Hz). $^{13}$C-NMR; δ (methanol-$d_4$), 176.9, 174.4, 172.2, 71.4, 64.6, 62.5, 58.9, 48.4, 42.1, 42.0, 34.8, 27.3, 26.9, 24.5, 21.8 and 17.0.

EXAMPLE 19

2S-(3S-Hydroxycarbamoyl-2R-isobutyl-hex-5-enoylamino)-3,3-dimethyl-butyric acid 2-methoxy-ethyl ester.

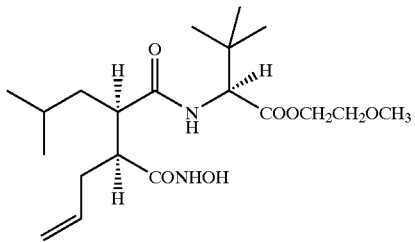

The title compound was prepared using an analogous route to that described for example 13 replacing L-phenylalanine with L-tert-leucine. $^1$H-NMR; δ (methanol-$d_4$), 8.28 (1H, d, J=8.6 Hz), 5.54 (1H, m), 4.88 (2H, m), 4.26 (1H, m), 4.14 (2H, m), 4.07 (2H, m), 3.24 (3H, s), 2.62 (1H, m), 2.17–1.95 (3H, bm), 1.44–1.18 (3H, bm), 1.00 (1H, m), 0.95 (9H, s), 0.81 (3H, d, J=6.4 Hz) and 0.73 (3H, d, J=6.5 Hz). $^{13}$C-NMR; δ (methanol-$d_4$), 176.8, 172.4, 172.1, 136.0, 117.5, 71.3, 64.6, 62.7, 62.6, 58.9, 48.3, 47.6, 41.8, 36.3, 35.1, 34.8, 30.7, 27.3, 26.8, 24.5 and 21.8.

EXAMPLE 20

2S-(3S-Hydroxycarbamoyl-2R-isobutyl-hex-5-enoylamino)-3-phenylpropionic acid cyclopentyl ester.

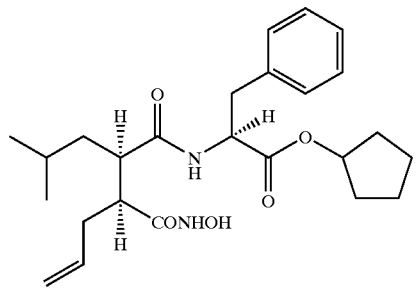

The title compound was prepared using an analogous route to that described for example 3 replacing L-phenylalanine isopropylester with L-phenylalanine cyclopentyl-ester. $^1$H-NMR; δ (methanol-$d_4$), 7.18–7.02 (5H, m), 5.32 (1H, m), 5.06 (1H, m), 4.79–4.63 (3H, m), 3.10 (1H, dd, J=14.0, 5.1 Hz), 2.78 (1H, dd, J=13.9, 10.6 Hz), 2.36 (1H, dt, J=11.1, 3.0 Hz), 1.90 (1H, dt, J=11.6, 3.4 Hz), 1.80–1.16 (13H, bm), 0.89 (1H, m), 0.79 (3H, d, J=6.4 Hz) and 0.73 (3H, d, J=6.5 Hz). $^{13}$C-NMR; δ (methanol-$d_4$), 176.3, 172.7, 172.4, 138.3, 136.1, 130.2, 129.5, 128.0, 117.3, 79.6, 55.2, 47.9, 47.8, 41.6, 38.3, 35.7, 33.5, 26.6, 24.7, 24.5 and 21.7.

EXAMPLE 21

2S-(3S-Hydroxycarbamoyl-2R-isobutyl-hexanoylamino)-3-phenylpropionic acid isopropyl ester.

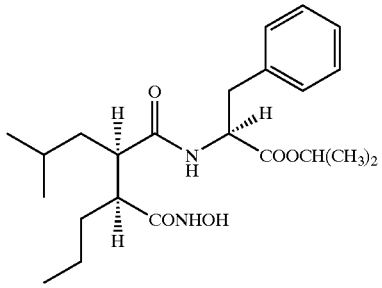

The title compound was prepared by an analogous route to that described for example 15. $^1$H-NMR; δ (methanol-$d_4$), 7.18–7.06 (5H, m), 4.90 (1H, sept, J=6.3 Hz), 4.64 (1H, dd, J=4.8, 10.7 Hz), 3.10 (1H, dd, J=4.8, 14.0 Hz), 2.79 (1H, dd, J=1 0.6, 14.0 Hz), 2.35 (1H, dt, J=3.3, 11.2 Hz), 1.89 (1H, dt, J=3.3, 11.0 Hz), 1.39 (2H, m), 1.15 (3H, d, J=6.3 Hz), 1.09 (3H, d, J=6.3 Hz), 1.06–0.83 (4H, m), 0.80 (3H, d, J=6.5 Hz), 0.73 (3H, d, J=6.6 Hz), 0.58 (3H, t, J=7.2 Hz) and 0.50 (1H, m). $^{13}$C-NMR; δ (methanol-$d_4$), 176.6, 173.2, 172.5, 138.5, 130.2, 129.5, 127.9, 70.2, 55.3, 48.1, 47.4, 41.7, 38.3, 33.2, 26.5, 24.6, 22.0, 21.9, 21.7, 21.2 and 14.0.

EXAMPLE 22

2S-(3S-Hydroxycarbamoyl-2R-isobutyl-hex-5-enoylamino)-3,3-dimethyl-butyric acid isopropyl ester.

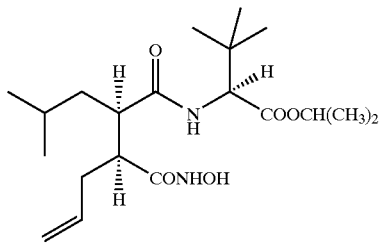

The title compound was prepared using an analogous route to that described for example 3 replacing L-phenylalanine with L-tert-leucine. $^1$H-NMR; δ (methanol-d$_4$), 5.56 (1H, m), 4.89 (3H, m), 4.20 (1H, m), 2.60 (1H, m), 2.21–1.93 (3H, bm), 1.50–1.24 (2H, m), 1.15 (6H, d, J=6.3 Hz), 1.00 (1H, m), 0.94 (9H, s), 0.82 (3H, d, J=6.5 Hz) and 0.73 (3H, d, J=6.5 Hz). $^{13}$C-NMR; δ (methanol-d$_4$), 176.7, 172.4, 171.7, 136.0, 117.5, 69.9, 62.7, 48.1, 47.6, 41.8, 36.3, 34.7, 27.3, 26.8, 24.5, 22.0 and 21.9.

EXAMPLE 23

2R-(3S-Hydroxycarbamoyl-2R-isobutyl-hex-5-enoylamino)-3-phenylpropionic acid isopropyl ester

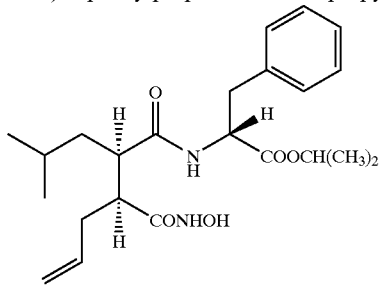

The title compound was prepared using an analogous route to that described for example 3 replacing L-phenylalanine isopropylester with, D-phenylalanine isopropylester. $^1$H-NMR; δ (methanol-d$_4$), 7.11 (5H, m), 5.52 (1H, m), 4.89 (3H, m), 4.66 (1H, dd, J=11.0, 4.6 Hz), 3.15 (1H, dd, J=14.1, 4.6 Hz), 2.75 (1H, dd, J=14.1, 11.1 Hz), 2.34 (1H, m), 2.16 (2H, m), 2.08 (1H, m), 1.27 (1H, m), 1.15 (3H, d, J=14.0, 6.3 Hz), 1.10 (3H, d, J=6.3 Hz), 0.69 (2H, m) and 0.52 (6H, d, J=5.0 Hz). $^{13}$C-NMR; δ (methanol-d$_4$), 176.6, 172.5, 172.4, 138.4, 136.3, 130.1, 129.5, 127.8, 117.4, 70.3, 55.2, 48.4, 47.8, 41.0, 38.2, 36.1, 26.3, 24.4, 22.0 and 21.6.

EXAMPLE 24

2S-[2R-(S-Hydroxycarbamoyl-methoxy-methyl)-4-methyl-pentanoylamino]-3,3-dimethyl-butyric acid isopropyl ester

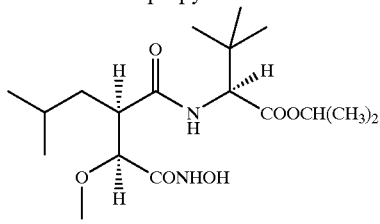

The title compound was prepared using an analogous route to that described for example 16 replacing L-phenylalanine with L-tert-leucine. $^1$H-NMR; δ (methanol-d$_4$), 4.92 (1H, m), 4.25 (1H, m), 3.42 (1H, d, J=9.8 Hz), 3.13 (3H, s), 2.77 (1H, m), 1.50–1.24 (2H, m), 1.15 (6H, d, J=6.3 Hz), 0.92 (9H, s), 0.87 (1H, m), 0.81 (3H, d, J=6.5 Hz) and 0.76 (3H, d, J=6.6 Hz). $^{13}$C-NMR; δ (methanol-d$_4$), 175.3, 171.7, 169.5, 82.9, 69.8, 62.3, 62.2, 58.0, 48.7, 38.3, 35.3, 27.1, 26.9, 24.2, 22.0 and 21.9.

EXAMPLE 25

2S-{(3S-Hydroxycarbamoyl-2R-isobutyl-hex-5-enoyl)-methyl-amino)-3-phenylpropionic acid isopropyl ester

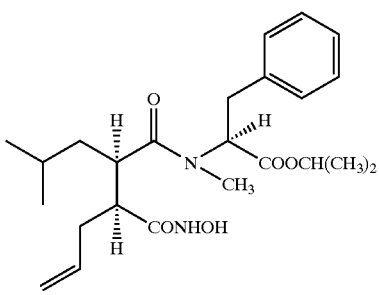

The title compound was prepared using an analogous route to that described for example 3 using N-methyl-L-phenylalanine isopropyl ester in place of L-phenylalanine isopropyl ester. $^1$H-NMR; δ (methanol-d$_4$), 7.18–7.00 (5H, m), 5.45 (1H, dd, J=11.8, 4.7 Hz), 5.34–5.17 (1H, m), 5.01–5.91 (1H, m), 4.85–4.66 (2H, m), 3.30 (1H, dd, J=14.6, 4.6 Hz), 3.02–2.84 (4H, m+s), 1.96–1.86 (1H, m), 1.68–1.50 (1H, m), 1.49–1.34 (2H, m), 1.16 (3H, d, J=6.2 Hz), 1.15 (3H, d, J=6.3 Hz), 1.01–1.10 (2H, m), 0.76 (3H, d, J=6.4, 6.5 Hz), 0.74 (3H, d, J=6.5 Hz). $^{13}$C-NMR; δ (methanol-d$_4$), 177.6, 172.4, 171.2, 128.2, 136.1, 130.1, 129.5, 128.1, 117.4, 70.4, 60.0, 42.8, 42.3, 35.3, 34.8, 33.8, 26.4, 24.5, 22.5, 22.0.

EXAMPLE 26

2S-(3S-Hydroxycarbamoyl-2R-isobutyl-hex-5-enoylamino)-3-phenylpropionic acid benzyl ester

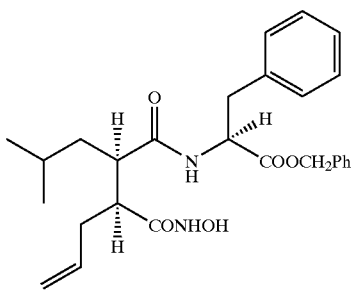

The title compound was prepared using an analogous route to that described for example 3 using L-phenylalanine benzyl ester in place of L-phenylalanine isopropyl ester. $^1$H-NMR; δ (methanol-d$_4$), 7.39–7.19 (1 0H, m), 5.44 (1H, m), 5.20 (2H, s), 4.89 (3H, m), 3.28 (1H, m), 2.95 (1H, dd, J=13.8, 10.8 Hz), 2.48 (1H, m), 2.03 (1H, dt, J=11.3, 3.2 Hz), 1.88 (1H, m), 1.45 (3H, m) 0.98 (1H, m), 0.81 (3H, d, J=6.4 Hz), 0.76 (3H, d, J=6.5 Hz). $^{13}$C-NMR; δ (methanol-d$_4$), 176.4, 172.7, 172.4, 138.3, 136.1, 129.6, 128.0, 117.3, 68.1, 55.2, 47.9, 41.6, 38.4, 35.7, 26.6, 24.5 and 21.6.

EXAMPLE 27

2S-(3S-Hydroxycarbamoyl-2R-isobutyl-hex-5-enoylamino)-4-methyl-pentanoic acid cyclopentyl ester

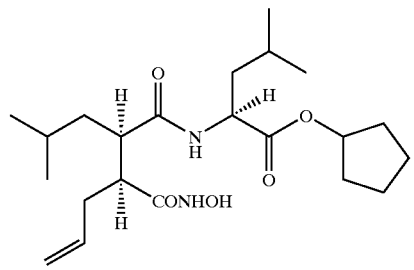

The title compound was prepared using an analogous route to that described for example 3 using L-leucine cyclopentyl ester in place of L-phenylalanine isopropyl ester. $^1$H-NMR; δ (DMSO-d$_6$), 10.52 (1H, d, J=1.5 Hz), 8.82 (1H, d, J=5.1 Hz), 8.42 (1H, d, J=7.4 Hz), 5.67–5.51 (1H, m), 5.08–5.01 (1H, m), 4.96–4.87 (2H, m), 4.28–4.19 (1H, m), 2.57–2.45 (1H, m), 2.27–2.04 (2H, m), 1.98–1.35 (14H, m) and 0.96–0.75 (13H, m). $^{13}$C-NMR; δ (DMSO-d$_6$), 174.3, 172.9, 170.0, 136.6, 117.1, 77.7, 51.2, 46.6, 40.2, 35.7, 32.9, 32.8, 25.8, 25.2, 25.1, 24.2, 23.8, 22.2 and 21.7.

EXAMPLE 28

3-Cyclohexyl-2S-(3S-hydroxycarbamoyl-2R-isobutyl-hex-5-enoylamino)-propionic acid cyclopentyl ester

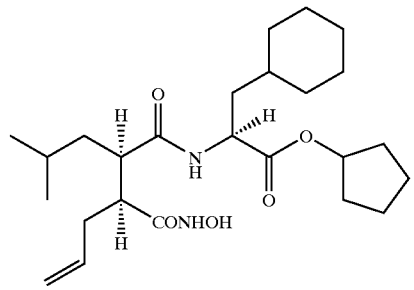

The title compound was prepared using an analogous route to that described for example 3 using L-cyclohexylalanine cyclopentyl ester in place of L-phenylalanine isopropyl ester. $^1$H-NMR; δ (DMSO-d$_6$), 10.50 (1H, d, J=1.4 Hz), 8.79 (1H, d, J=1.6 Hz), 8.39 (1H, d, J=7.7 Hz), 5.71–5.54 (1H, m), 5.11–5.03 (1H, m), 4.99–4.89 (2H, m), 4.37–4.26 (1H, m), 2.61–2.49 (1H, m), 2.30–2.08 (2H, m), 2.02–0.74 (25H, m), 0.87 (3H, d, J=6.4 Hz) and 0.81 (3H, d, J=6.4 Hz). $^{13}$C-NMR; δ (DMSO-d$_6$), 173.5, 172.3, 169.3, 135.9, 116.3, 77.0, 49.5, 46.0, 45.9, 40.3, 37.9, 35.0, 33.6, 33.2, 32.1, 31.2, 26.2, 26.1, 25.8, 25.2, 24.4, 23.5 and 21.5.

EXAMPLE 29

2S-(3S-Hydroxycarbamoyl-2R-isobutyl-hex-5-enoylamino)-3-phenylpropionic acid 1-methyl-piperidin-4-yl ester

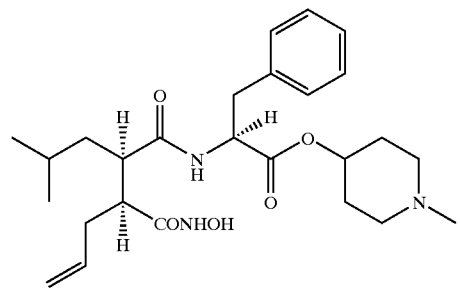

EXAMPLE 30

2S-(3S-Hydroxycarbamoyl-2R-isobutyl-hex-5-enoylamino)-3-phenylpropionic acid 1-ethyl-propyl ester

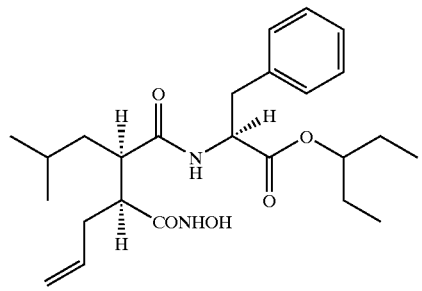

The title compound was prepared using an analogous route to that described for example 3 using L-phenylalanine 1-ethyl-propyl ester in place of L-phenylalanine isopropyl ester. $^1$H-NMR; δ (methanol-d$_4$), 8.65 (1H, d, J=8.5 Hz), 7.31–7.11 (5H, m), 5.50–5.33 (1H, m), 4.88–4.74 (4H, m), 3.27 (1H, dd, J=9.7, 4.6 Hz), 2.88 (1H, dd, J=13.9, 11.0 Hz), 2.46 (1H, dt, J=11.1, 3.1 Hz), 1.99 (1H, dt, J=11.4, 3.4 Hz), 1.89–1.76 (1H, m), 1.70–1.49 (6H, m), 1.33–1.24 (1H, m), 1.07–0.94 (1H, m) and 0.94–0.60 (12H, m). $^{13}$C-NMR; δ (methanol-d$_4$), 175.3, 172.0, 171.4, 137.4, 135.1, 129.2, 128.5, 127.0, 116.2, 78.5, 54.3, 46.9, 40.6, 37.5, 34.7, 26.7, 26.7, 25.6, 23.5 and 20.7.

EXAMPLE 31

2S-(3S-Hydroxycarbamoyl-2R-isobutyl-hex-5-enoylamino)-3-phenylpropionic acid 1S-methyl-butyl ester

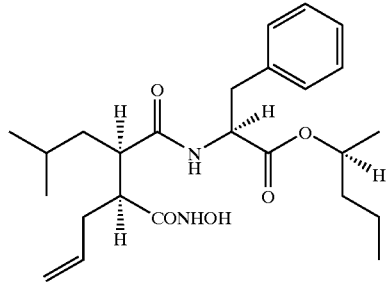

The title compound was prepared using an analogous route to that described for example 3 using L-phenylalanine 1S-methyl-butyl ester in place of L-phenylalanine isopropyl ester. $^1$H-NMR; δ (methanol-$d_4$), 8.64 (1H, d, J=8.4 Hz), 7.29–7.12 (5H, m), 5.27 (1H, m), 4.89 (4H, m), 3.24 (1H, dd, J=1 3.9, 4.9 Hz), 2.88 (1H, dd, J=13.9, 10.8 Hz), 2.46 (1H, dt, J=1 13, 3.2 Hz), 1.99 (1H, dd, J=1 13, 3.4 Hz), 1.83 (1H, m), 1.64–1.41 (4H bm), 1.33 (3H, m), 1.23 (3H, d, J=6.3 Hz), 1.09 (1H, m), 0.90 (6H, m) and 0.83 (3H, d, J=6.5 Hz). $^{13}$C-NMR; δ (methanol-$d_4$), 176.3, 172.6, 172.4, 138.4, 136.1, 130.3, 129.5, 128.0, 117.3, 73.3, 55.2, 47.9, 41.6, 39.1, 38.4, 35.7, 26.6, 24.6, 21.7, 20.3, 19.7 and 14.2.

EXAMPLE 32

2S-(3S-Hydroxycarbamoyl-2R-isobutyl-hex-5-enoylamino)-3-phenylpropionic acid cyclohexyl ester

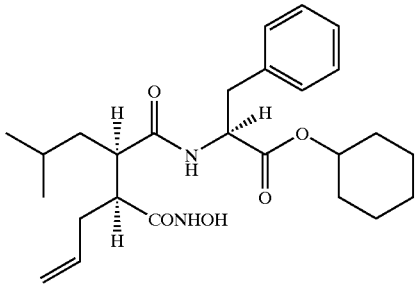

The title compound was prepared using an analogous route to that described for example 3 using L-phenylalanine cyclohexyl ester in place of L-phenylalanine ispropyl ester. $^1$H-NMR; δ (DMSO-$d_6$), 10.39 (1H, s), 8.71 (1H, s), 8.42 (1H, d, J=8.0 Hz), 7.29–7.11 (5H, m), 5.39 (1H, ddt, J=17.0, 10.3, 6.6 Hz), 4.81 (1H, dd, J=10.3, 2.0 Hz), 4.73 (1H, dd, J=17.2, 2.0 Hz), 4.69–4.53 (2H, m), 3.09 (1H, dd, J=13.8, 4.8 Hz), 2.85 (1H, dd, J=13.8, 10.6 Hz), 2.47–2.34 (1H, m), 2.00–1.16 (15H, m), 0.93–0.78 (1H, m), 0.82 (3H, d, J=64 Hz) and 0.76 (3H, d, J=6.4 Hz). $^{13}$C-NMR; δ (DMSO-$d_6$), 173.7, 171.2, 169.6, 137.7, 136.2, 129.4, 128.4, 126.8, 116.2, 73.0, 53.7, 46.2, 45.9, 40.5, 36.9, 34.7, 31.3, 31.2, 25.3, 25.2, 24.6, 23.5 and 21.8.

EXAMPLE 33

2S-{2R-[1S-Hydroxycarbamoyl-2-(thiophen-2-ylsulphanyl)-ethyl]-4-methyl-pentanoylamino}-3,3-dimethyl-butyric acid isopropyl ester

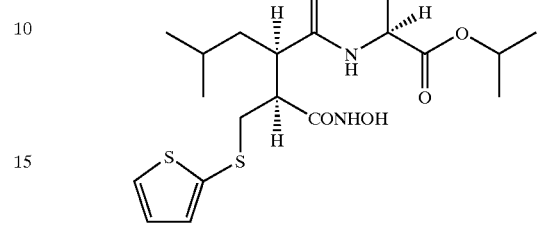

The title compound was prepared using an analogous route to that described for example 17.2-[1R-(1S-Isopropoxycarbonyl-2,2-dimethyl-propylcarbamoyl)3-methyl-butyl]-acrylic acid was prepared from 3R-hydroxycarbonyl-2-benzyloxy-carbonyl-5-methyihexanoic acid benzyl ester and L-tert-butyl glycine isopropyl ester using methods similar to those described in example 4. $^1$H-NMR; δ (methanol-$d_4$), 7.44 (1H, m), 7.11 (1H, m), 6.96 (1H, m), 4.98 (1H, m), 4.23 (1H, s), 3.00 (1H, m), 2.79 (2H, m), 2.42 (1H, m), 1.53 (1H, m), 1,37 (1H, m), 1.24 (3H, s), 1.11 (3H, s), 1.11 (1H, m), 1.00 (9H, s), 0.88 (3H, d, J=6.4 Hz) and 0.81 (3H, d, J=6.6 Hz). $^{13}$C-NMR; δ (methanol-$d_4$), 176.3, 172.0, 171.5, 135.3, 131.2, 129.1, 70.3, 63.0, 48.4, 48.1, 42.0, 40.8, 35.2, 27.8, 27.2, 24.8, 22.5 and 22.2.

EXAMPLE 34

2S-(3S-Hydroxycarbamoyl-2R-isobutyl-hex-5-enoylamino)-3-phenylpropionic acid 1R-methyl-butyl ester

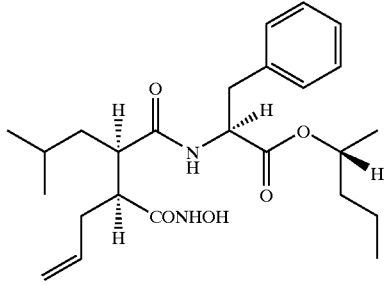

The title compound was prepared using an analogous route to that described for example 3 using L-phenylalanine 1R-methyl-butyl ester in place of L-phenylalanine isopropyl ester. $^1$H-NMR; δ (methanol-$d_4$), 7.30–7.12 (5H, m), 5.57–5.34 (1H, m), 5.01–4.93 (1H, m), 4.84–4.70 (3H, m), 3.22 (1H, dd, J=13.9, 4.9 Hz), 2.88 (1H, dd, J=13.9, 10.9 Hz), 2.46 (1H, dt, J=11.1, MHz), 1.99 (1H, dt, J=11.4, 3.3 Hz), 1.90–1.77 (1H, m), 1.68–1.21 (7H, m), 1.16 (3H, d, J=6.3 Hz), 1.12–0.89 (7H, m) and 0.83 (3H, d, J=6.5 Hz). $^{13}$C-NMR; δ (methanol-$d_4$), 176.3, 172.6, 172.4, 138.3, 137.9, 136.1, 130.3, 129.5, 128.0, 117.3, 73.2, 55.4, 47.9, 41.6, 39.2, 38.4, 35.7, 26.6, 24.6, 21.7, 20.2, 19.7 and 14.2.

EXAMPLE 35

2S-(3S-Hydroxycarbamoyl-2R-isobutyl-hex-5-enoylamino)-3-phenylpropionic acid tetrahydro-furan-3(R, S)-yl ester

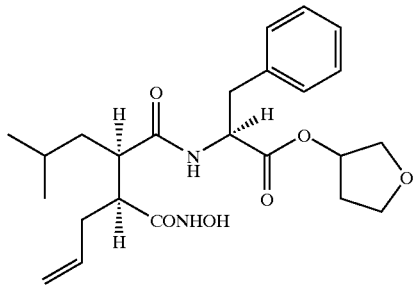

The title compound was prepared using an analogous route to that described for example 3 using L-phenylalanine tetrahydrofuran-3(R, S)-yl ester in place of L-phenylalanine isopropyl ester. $^1$H-NMR; δ (methanol-$d_4$), 7.29–7.13 (5H, m), 5.51–5.29 (2H, m), 4.85–4.75 (3H, m), 3.91–3.66 (4H, m), 3.23 (1H, dd, J=14.0, 5.0 Hz), 2.96–2.86 (1H, m), 2.47 (1H, dt, J=11.0, 3.0 Hz), 2.28–2.10 (1H, m), 2.05–1.78 (3H, m), 1.55–1.44 (2H, m), 1.37–1.30 (1H, m), 1.03–0.92 (1H, m), 0.89 (3H, d, J=6.4 Hz) and 0.83 (3H, d, J=6.5 Hz). $^{13}$C-NMR; δ (methanol-$d_4$), 176.5, 172.7, 172.4, 138.2, 136.1, 130.3, 129.6, 128.1, 117.3, 77.3, 73.8, 67.9, 55.2, 47.9, 41.6, 38.2, 33.2, 26.7, 24.5 and 21.7.

EXAMPLE 36

2S-(3S-Hydroxycarbamoyl-2R-isobutyl-hex-5-enoylamino)-3,3-dimethyl-butyric acid cyclopentyl ester

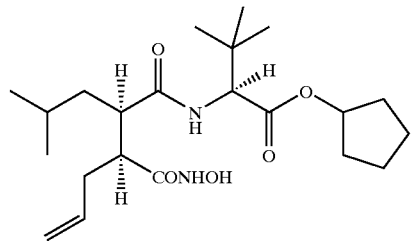

The title compound was prepared using an analogous route to that described for example 3 using L-tert-butyl glycine cyclopentyl ester in place of L-phenylalanine isopropyl ester. $^1$H-NMR; δ (methanol-$d_4$), 5.71–5.57 (1H, m), 5.18–5.13 (1H, m), 5.03–4.95 (2H, m), 4.29 (1H, s), 2.76–2.66 (1H, m), 2.31–2.03 (3H, m), 1.90–1.38 (10H, m), 1.14–0.99 (2H, m), 1.06 (9H, s), 0.92 (3H, d, J=6.5 Hz) and 0.87 (3H, d, J=6.5 Hz). $^{13}$C-NMR; δ (methanol-$d_4$), 177.2, 172.8, 172.5, 136.4, 117.9, 79.7, 63.1, 42.2, 36.8, 35.2, 34.0, 33.8, 27.7, 25.1, 25.0, 24.9 and 22.3.

EXAMPLE 37

2S-[2R-(1S-Cyclopentyl-hydroxycarbamoyl-methyl)-4-methyl-pentanoylamino]-3-phenyl-propionic acid cyclopentyl ester

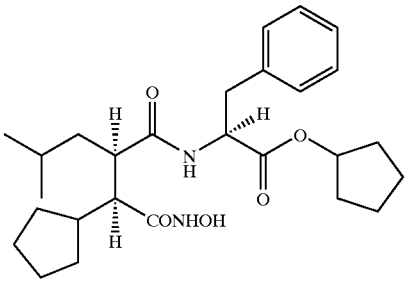

The title compound was prepared using chemistry analogous to that described in WO 97/19053 involving an initial coupling between 2S-cyclopentyl-3R-isobutyl-succinic acid 1-benzyl ester and L-phenylalanine cyclopentyl ester. $^1$H-NMR; δ (methanol-$d_4$), 8.51 (1H, d, J=8.1 Hz), 7.31–7.16 (5H m), 5.13–5.04 (1H, m), 4.73–4.62 (3H m), 3.01 (1H, dd, J=13.9, 6.4 Hz), 2.92 (1H, dd, J=13.9, 8.8 Hz), 2.78 (1H, dd, J=10.7, 3.8 Hz), 2.24–2.02 (3H m), 1.90–1.21 (20H, m), 1.12-0-96 (1H, m) and 0.93–0.81 (1H, m). $^{13}$C-NMR; δ (methanol-$d_4$), 176.5, 173.2, 172.9, 144.0, 138.5, 130.6, 129.9, 128.4, 113.8, 79.8, 55.6, 51.5, 42.6, 41.3, 39.2, 33.9, 33.8, 32.3, 30.2, 26.5, 26.1, 25.0, 22.8 and 22.1.

EXAMPLE 38

2S-[2R-(1S-Hydroxy-hydroxycarbamoyl-methyl)-pent-4-ynoylamino]-3-phenylpropionic acid cyclopentyl ester

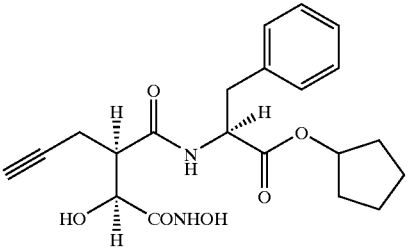

(a) 2S-Hydroxy-3R-prop-2-ynyl-succinic acid diisopropyl ester

A solution of S-malic acid diisopropyl ester (5.5 g, 25.2 mmol) in dry THF (20 ml) was added to a solution of freshly prepared lithium disopropylamide [from N,N-diisopropylamine (6.9 mL, 52.0 mmol) and 2.5 M n-butyllithium (21 mL, 52.5 mmol)] in dry THF (50 mL), whilst maintaining the temperature at −5° C. The reaction mixture was stirred at −5° C. for 75 minutes then cooled to −70° C. A solution of propargyl bromide (80% solution in toluene, 3.1 mL, 27.7 mmol) was added slowly, whilst maintaining the temperature at −70° C. The cooling bath was removed and the solution was stirred overnight before quenching with saturated aqueous ammonium chloride (50 mL). The aqueous lyaer was separated and extracted with ethyl acetate. The organic layers were combined and washed with 1M hydrochloric acid and brine and dried over anhydrous magnesium sulphate. The solution was filtered and concentrated in vacuo to give a brown oil which was purified by column chromatography (silica gel, 25% ethyl acetate in hexane) to provide the title compound as an orange oil (1.4 g, 22%; 9:1 mixture of diastereomers by NMR). $^1$H-NMR; δ (CDCl$_3$, major diastereoisomer), 5.12 (1H, m), 5.04 (1H, m), 4.45 (1H, dd, J=5.8, 2.6 Hz), 3.17 (1H, d, J=5.8 Hz), 3.08 (1H, m), 2.67 (1H, m), 2.05 (1H, t, J=2.9 Hz), 1.29 (6H, d, J=6.1 Hz) and 1.19 (6H, d, J=6.2 Hz).

(b) 2S-Hydroxy-3R-prop-2-ynyl-succinic acid

A solution of 2S-hydroxy-3R-prop-2-ynyl-succinic acid diisopropyl ester (2.47 g, 9.5 mmol) in 1M sodium hydroxide (32 mL, 3 mmol) was heated at reflux for 1 hour then cooled to room temperature. The solution was acidified to pH 2 with 1M hydrochloric acid and extracted with ethyl acetate. The combined organics were dried over magnesium sulphate, filtered and concentrated in vacuo to provide the title compound as a brown oil (0.94 g, 64%). $^1$H-NMR; δ (methanol-d$_4$), 4.37 (1H, d, J=3.4 Hz), 3.01 (1H, m), 2.51 (2H, m), 2.21 (1H, t, J=2.5 Hz).

(c) 2R-(2,2-Dimethyl-5-oxo-[1,3]dioxolan-4S-yl)-pent-4-ynoic acid

2S-Hydroxy-3R-prop-2-ynyl-succinic acid (0.94 g, 6.18 mmol) was dissolved in ethyl acetate (5 mL). Dimethoxypropane (10 mL) and p-toluenesulfonic acid (10 mg) were added and the solution heated at reflux for 2.5 hours. Solvents were removed in vacuo to provide the title compound as a dark brown gum (1.0 g, 84%). $^1$H-NMR; δ (CDCl$_3$), 4.80 (1H, d, J=2.4 Hz), 3.22 (1H, mL), 2.86 (1H, ddd, J=17.2, 5.4, 2.6 Hz), 2.61 (1H, ddd, J=13.0, 10.3, 2.6 Hz), 2.10 (1H, t, J 2.8 Hz), 1.58 (3H s) and 1.57 (3H s).

(d) 2S-[2R-(1S-Hydroxycarbamoyl-methyl)-pent-4-ynoylamino]-3-phenylpropionic acid cyclopentyl ester.

The title compound was prepared using an analogous route to that described in example 8. 2R-(2,2-Dimethyl-5-oxo-[1,3]dioxolan-4S-yl)-pent-4-ynoic acid pentafluorophenyl ester was prepared by treatment of 2R-(2,2-dimethyl-5-oxo-[1,3]dioxolan-4S-yl)-pent-4-ynoic acid with pentafluorophenol and N-(3-dimethylaminopropyl)-N'-ethylcarbodiimide hydrochloride in DCM. $^1$H-NMR; δ (methanol-d$_4$), 7.31–7.18 (5H m), 5.09–5.05 (1H, m), 4.64–4.58 (1H, m), 4.27 (1H, d, J=5.4 Hz), 3.06–2.,92 (3H, m), 2.48 (2H dd, J=7.6, 2.6 Hz), 2.32 (1H, t, J=2.6 Hz) and 1.84–1.47 (8H, bm). $^{13}$C-NMR; δ (methanol-d$_4$), 173.8, 172.6, 171.2, 137.8, 130.4, 129.5, 127.9, 79.7, 71.9, 55.4, 49.2, 38.8, 33.4, 33.3, 24.5 and 19.3.

EXAMPLE 39

2S-(3S-Hydroxycarbamoyl-2R-isobutyl-hex-5-enoylamino)-3-pyridin-3-yl-propionic acid cyclopentyl ester

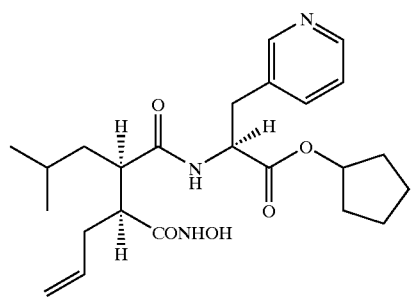

The title compound was prepared using an analogous route to that described for example 3 using L-3-pyridylalanine cyclopentyl ester in place of L-phenylalanine isopropyl ester. $^1$H-NMR; δ (DMSO-d$_6$), 10.42 (1H, bs), 8.67 (1H, bs), 8.51–8.33 (3H m), 7.74 (1H, d, J=7.9 Hz), 7.28 (1H, dd, J=7.7, 4.8 Hz), 5.37 (1H, ddt, J=17.0, 10.2, 6.7 Hz), 5.09–5.02 (1H, m), 4.82 (1H, dd, J=10.2 MHz), 4.73 (1H, dd, J=17.2, 2.0 Hz), 4.68–4.56 (1H, m), 3.12 (1H, dd, J=14.1, 4.8 Hz), 2.86 (1H, dd, J=1 4.0, 11.0 Hz), 2.41–2.30 (1H, m), 1.96–1.08 (13H, m), 0.92–0.74 (1H, m), 0.80 (3H d, J=6.4 Hz) and 0.76 (3H, d, J=6.5 Hz). $^{13}$C-NMR; δ (methanol-d$_4$), 173.7, 171.3, 169.5, 150.5, 147.9, 137.2, 133.4, 123.6, 116.4, 77.6, 53.0, 46.2, 45.9, 33.9, 32.4, 32.3, 25.3, 24.6, 23.7 and 21.7.

EXAMPLE 40

3-tert-Butoxy-2S-(3S-hydroxcarbamoyl-2R-isobutyl-hex-5-enoylamino)-propionic acid cyclopentyl ester

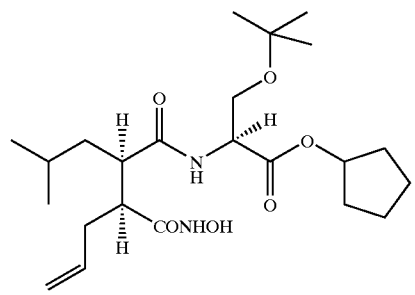

The title compound was prepared using an analogous route to that described for example 3 using L-tert-butoxyserine cyclopentyl ester in place of L-phenylalanine isopropyl ester. $^1$H-NMR; δ (CDCl$_3$), 6.66 (1H, d, J=8.1 Hz), 5.73–5.63 (1H, m), 5.275.22 (1H, m), 5.10–4.99 (2H m), 4.72–4.67 (1H, m), 3.80 (1H, dd, J=8.8, 3.0 Hz), 3.57 (1H, dd, J=8.8, 3.0 Hz), 2.65–2.57 (1H, m), 2.53–2.34 (2H, m), 2.22–2.17 (1H, m), 1.88–1.56 (1H, m), 1.19 (9H s), 0.91 (3H d, J=6.5 Hz) and 0.87 (3H d, J=6.5 Hz). 46.2, 39.7, 34.7, 32.6, 32.4, 27.2, 25.8, 23.8, 23.7, 23.6 and 21.3.

EXAMPLE 41

2S-(3S-Hydroxycarbamoyl-2R-isobutyl-hex-5-enoylamino)-2-phenylethanoic acid cylcopentyl ester

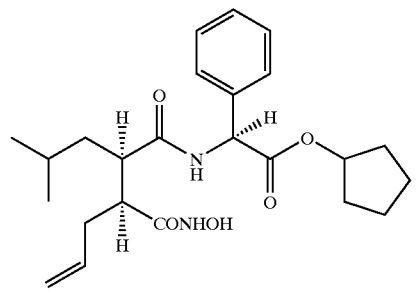

The title compound was prepared using an analogous route to that described for example 3 using L-phenylglycine cyclopentyl ester in place of L-phenylalanine isopropyl ester. $^1$H-NMR; δ (methanol-d$_4$), 7.41–7.32 (5H, m), 5.70–5.49 (1H, m), 5.42 (1H, s), 5.21–5.15 (1H, m), 4.92–4.85 (2H m), 2.69–2.61 (1H, m), 2.20–2.13 (2H, m), 1.95–1.51 (11H, m), 1.18–1.00 (1H, m), 0.95 (3H d, J=6.5 Hz). $^{13}$C-NMR; δ (methanol-d$_4$), 176.3, 172.3, 171.5, 137.5, 135.9, 129.8, 129.0, 117.4, 79.8, 58.7, 58.6, 48.3, 47.3, 41.5, 36.0, 33.3, 26.7, 24.4 and 21.7.

EXAMPLE 42

2S-[5-(2-Chlorophenyl)-2R-(1S-hydroxy-hydroxycarbamoyl-methyl)-pent-4-ynoylamino]-3-phenylpropionic acid cyclopentyl ester

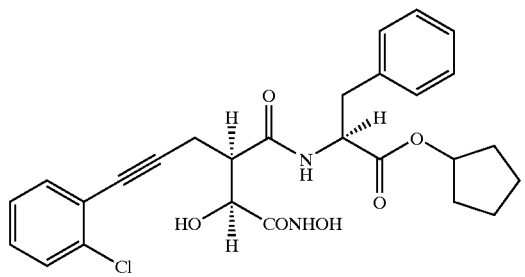

(a) 5-(2-Chlorophenyl)-2R-(2,2-dimethyl)-5-oxo-[1,3]-dioxolan-4S-yl)-pent-4-ynoic acid 2R-(2,2-Dimethyl-5-oxo-[1,3]dioxolan-4S-yl)-pent-4-ynoic acid (example 38, 3 g, 15.6 mmol) and 1-chloro-2-iodobenzene (1.59 mL, 13.0 mmol) were dissolved in a mixture of diisopropylamine (5.2 mL) and DCM (20 mL) in a 35 mL pressure tube. Dichlorobis(triphenylphosphine) palladium(II) (379 mg, 4.6 mol %) and copper (I) iodide (89 mg, 4.0 mol %) were added and the tube heated at room temperature for 4 hours. The reaction mixture was partitioned between DCM and IM hydrochloric acid. The product was extracted with saturated aqueous sodium hydrogen carbonate. The basic extracts were combined, acidified to pH2 with 1M hydrochloric acid then extracted with dichloromethane. Combined organics were dried (magnesium sulphate), filtered and solvents removed in vacuo to provide the title compound as an orange solid (3.2 g, 81%). $^{1}$H-NMR; δ (CDCl$_{3}$), 7.46–7.37 (2H, m), 7.28–7.17 (2H m), 5.00 (1H, d, J=2.8 Hz), 3.39–3.32 (1H, m), 3.16 (1H, dd, J=17.3, 5.2 Hz), 2.92 (1H, dd, J=17.8, 10.7 Hz), 1.60 (3H s) and 1.58 (3H s).

(b) 2S-[5-(2-Chlorophenyl)-2R-(1S-hydroxy-hydroxcarbamoyl-methyl)-pent-4-ynoylamino]-3-phenylpropionic acid cyclopentyl ester.

The title compound was prepared using an analogous route to that described for example 8 using 5-(2-chlorophenyl)-2R-(2,2-dimethyl)-5-oxo-[1,3]-dioxolan-4S-yl)-pent-4-ynoic acid pentafluorophenyl ester in place of 2R-(2,2-dimethyl-5-oxo-[1,3-dioxolan-4S-yl)-4-methyl-pentanoic acid pentafluorophenyl ester. The pentafluorophenyl ester was prepared by treatment of 5-(2-chlorophenyl)-2R-(2,2dimethyl)-5-oxo-[1,3]-dioxolan-4S-yl)-pent-4-ynoic acid with pentafluorophenol and N-(3-dimethylaminopropyl)-N-ethylcarbodiimide hydrochloride in DCM. $^{1}$H-NMR; δ (methanol-d$_{4}$), 8.30 (1H, d, J=6.8 Hz), 7.48–7.23 (9H, bm), 5.00 (1H, m), 4.67–4.65 (1H, m), 4.35 (1H, d, J=4.6 Hz), 3.10–2.97 (3H m), 2.78 (2H d, J=7.1 Hz) and 1.691.50 (8H bm). $^{13}$C-NMR; δ (methanol-d$_{4}$), 173.8, 172.5, 171.3, 137.8, 136.8, 134.7, 130.5, 130.3, 130.2, 129.5, 127.9, 127.7, 92.9, 80.3, 79.6, 72.2, 55.5, 39.0, 33.5, 33.3, 24.6, 24.5 and 20.2.

EXAMPLE 43

2S-(3S-Hydroxycarbamoyl-2R-isobutyl-6-phenyl-hex-5-enoylamino)-3-phenyl-propionic acid cyclopentyl ester.

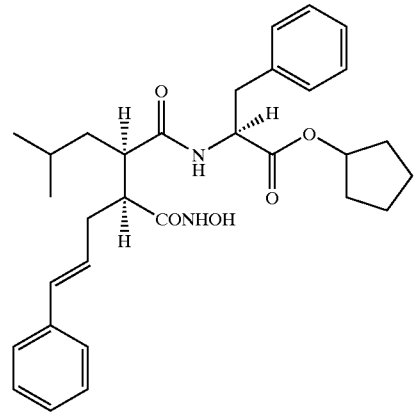

(a) 2S-[1R-(1S-Cyclopentyloxycarbonyl-2-phenyl-ethylcarbamoyl)-3-methyl-butyl]-5-phenyl-pent-4-enoic acid.

A solution of 2S-[1R-(1S-cyclopentyloxycarbonyl-2-phenyl-ethylcarbamoyl)-3-methyl-butyl]-pent-4-enoic acid. (previously prepared for example 20) (400 mg, 0.93 mmol), palladium acetate (10.5 mg, 0.05 mmol), tri-ortho-tolyl phosphine (28 mg, 0.1 mmol), iodobenzene (208 μL, 1.86 mmol) and triethylamine (250 μL, 1.86 mmol)) in acetonitrile was heated at 75° C. for 1 hour. The cooled reaction mixture was partitioned between ethyl acetate and 1.0 M hydrochloric acid. The organic layer was washed with water and brine, dried over anhydrous magnesium sulphate, filtered and evaporated. Purification by chromatography on silica gel gave the product as a white powder (99 mg, 0.2 mmol, 21%). $^{1}$H-NMR; δ (CDCl$_{3}$), 7.36–7.18 (8H m), 7.13–7.07 (2H m), 6.37 (1H, d, J=15.7 Hz), 6.17 (1H, d, J=8.1 Hz), 6.08–5.96 (1H, m), 5.23–5.17 (1H, m), 4.91–4.80 (1H, m), 3.18 (1H, dd, J=14.0, 5.9 Hz), 3.01 (1H, dd, J=14.0, 7.0 Hz), 2.63–2.50 (2H m), 2.45–2.37 (1H, m), 2.23–2.07 (1H, m), 1.92–1.44 (1 OH, m), 1.27–1.24 (1H, m), 0.86 (3H, d, J=6.5 Hz), 0.85 (3H, d, J=6.4 Hz).

(b) 2S-(3S-Hydroxycarbamoyl-2R-isobutyl-6-phenyl-hex-5-enoylamino)-3-phenyl-propionic acid cyclopentyl ester.

The title compound was prepared from 2S-[1R-(1S-cyclopentyloxycarbonyl-2-phenyl-ethylcarbamoyl)-3-methyl-butyl]-5-phenyl-pent-4-enoic acid using chemistry previously described eg example 3c. $^{1}$H-NMR; δ (methanol-d$_{4}$), 8.63–8.49 (1H, m), 7.24–6.96 (10H, m), 6.17–6.02 (1H, m), 5.90–5.69 (1h, m), 5.13–5.04 (1H, m), 4.754.68 (1H, m), 3.13 (1H, dd, J=1 3.9, 5.4 Hz), 2.81 (1H, dd, J=13.9, 10.5 Hz), 2.53–2.29 (2H, m), 2.01–1.34 (12H, m), 1.02–0.90 (1H, m), 0.83 (3H, d, J=6.4 Hz), 0.75 (3H, d, J=6.6 Hz).

The following compounds of the invention (Examples 44–49) were prepared using procedures similar to those described in Examples 8, 16, 3, and 41 respectively. Products obtained as mixtures of diastereoisomers were separated by reverse phase HPLC.

EXAMPLE 44

2-[2R-(S-Hydroxy-hydroxycarbamoyl-methyl-pentanoylamine]-2-phenyl-ethanoic acid cyclopentyl ester

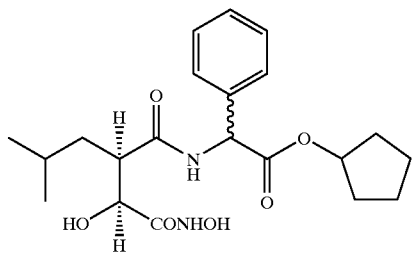

The above compound was prepared using procedures similar to those described in example 8 using phenylglycine cyclopentyl ester.

Diastereoisomer A $^1$H-NMR; δ (MeOD), 7.4–7.29 (5H, m), 5.43 (1H, s), 5.2–5.14 (1H, m), 4.02 (1H, d, J=6.9 Hz), 2.94–2.85 (1H, m), 1.91–1.34 (10H, bm), 1.25–1.14 (1H, m) and 0.86 (6H, dd, J=6.5, 11 5 Hz).

$^{13}$C-NMR; δ (MeOD), 175.6, 171.8, 171.4, 137.8, 129.8, 129.4, 128.6, 80.0, 73.2, 58.5, 49.2, 39.1, 33.3, 33.3, 26.8, 24.5, 24.4, 23.7 and 22.1.

Diastereoisomer B

1H-NMR; δ (MeOD), 7.33–7.19 (5H, m), 5.3 (1H, s), 5.11–5.06 (1H, m), 3.81 (1H, d, J=7.3 Hz), 2.83–2.74 (lH, m), 1.83–1.45 (10H, bm), 1.12–1.03 (lH, m) and 0.88–0.81 (6H, dd, J=6.4, 12.3 Hz). 13C-NMR; δ (MeOD), 175.8, 171.8, 171.5, 137.3, 129.8, 129.5, 128.8, 79.9, 73.3, 58.7, 48.9, 39.2, 33.3, 33.3, 26.7, 24.5, 24.5, 24.0 and 22.2.

EXAMPLE 45

2-(3S-Hydroxycarbamoyl-2R-isobutyl-hex-5-enoylamino)-2-phenylethanoic acid isopropyl ester.

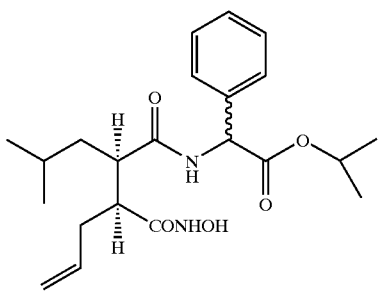

The above compound was prepared using methods similar to those described in example 41, using phenylglycine isopropyl ester.

Diastereoisomer A $^1$H-NMR; δ (MeOD), 7.34–7.24 (5H, m), 5.59–5.42 (1H, m), 5.36 (1H, s), 5.02–4.77 (3H, m), 2.63–2.53 (1H, m), 2.17–2.02 (2H, m), 1.89–1.78 (1H, m), 163–1.45 (2H, m), 1.18 (3H, d, J=6.3 Hz), 1.05 (3H, d, J=6.2 Hz), 1.00–0.93 (1H, m), 0.88 (3H, d, J=6.5 Hz) and 0.81 (3H, d, J=6.5 Hz). $^{13}$C-NMR; δ (MeOD), 176.2, 172.4, 171.3, 137.6, 136.0, 129.9, 129.6. 129.0. 117.4, 70.5, 58.7, 47.4, 41.5, 36.0, 26.7, 24.5, 21.9, 21.7 and 21.7.

Diastereoisomer B $^1$H-NMR; δ (MeOD), 7.4–7.34 (5H, m), 5.77–5.61 (1H, m), 5.42 (1H, s), 5.1–4.98 (3H, m), 2.7–2.6 (1H, m), 2.44–2.17 (3H, m), 1.6H.5 (1H, m), 1.42–1.29 (1H, m), 1.25 (3H, d, J=6.3 Hz), 1.13 (3H, d, J=6.2 Hz), 1.09–1.00 (1H, m) and 0.81 (6H, d, J=6.4 Hz). $^{13}$C-NMR; δ (MeOD), 176.4, 172.5, 171.5, 137.2, 136.4, 129.9, 129.6, 129.0, 117.5, 70.5, 58.8, 48.4, 47.4, 41.3, 36.0, 27.1, 24.3, 21.9, 21.8 and 21.6.

EXAMPLE 46

2-[2R-(S-Hydroxycarbamoyl-methoxy-methyl)-4-methyl-pentanoylamino]-3-phenylethanoic acid cyclopentyl ester

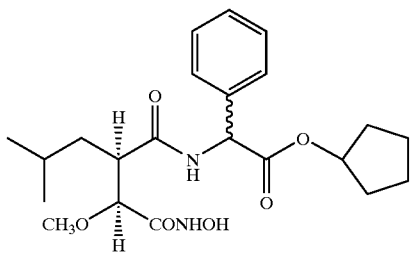

The above compound was prepared using methods similar to those described in example 16, using phenylglycine cyclopentyl ester.

Diastereoisomer A $^1$H-NMR; δ (MeOD), 8.83 (1H, d, J=6.6 Hz), 7.48–7.29 (5H, m), 5.44–5.42 (1H, m), 5.20–5.16 (1H, m), 3.53 (1H, d, J=9.7 Hz), 3.17 (3H, s), 2.89–2.79 (1H, m), 1.90–1.54 (1 OH, bm), 1.06–0.99 (1H, m), 0.95 (3H, d, J=6.5 Hz) and 0.90 (3H, d, J=6.4 Hz). 13 C-NMR; δ (MeOD), 175.3, 171.6, 169.4, 137.5, 129.7, 129.4, 128.7, 83.1, 79.9, 58.7, 58.1, 48.5, 38.4, 33.4, 33.3, 26.7, 24.5, 24.3 and 21.8.

Diastereoisomer B $^1$H-NMR; δ (MeOD), 7.39–7.30 (5H, m), 5.45 (1H, s), 5.21–5.15 (1H, m), 3.59 (1H, d, J=9.4 Hz), 3.29 (3H, s), 2.89–2.79 (1H, m), 1.93–1.49 (9H, bm), 1.42–1.21 (1H, m), 1.01 (1H, ddd, J=3.7, 9.9, 13.3 Hz), 0.83 (3H, d, J=6.5 Hz) and 0.79 (3H, d, J=6.6 Hz). $^{13}$C-NMR; δ (MeOD), 175.1, 171.5, 169.5, 137.9, 129.7, 129.4, 128.7, 83.0, 79.8, 58.5, 58.3, 48.6, 38.5, 33.3, 27.8, 24.5, 24.4, 24.1 and 21.7.

EXAMPLE 47

2-(3S-Hydroxycarbamoyl-2R-isobutyl-hex-5-enoylamino)-2-(4-methoxyphenyl)ethanoic acid cyclo-pentyl ester

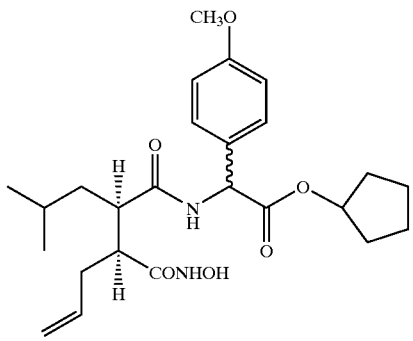

The above compound was prepared using methods similar to those described in example 41, using 4-methoxyphenylglycine cyclopentyl ester.

Diastereoisomer A

¹H-NMR; δ (MeOD), 8.94 (1H, d, J=6.4 Hz), 7.32 (2H, d, J=8.7 Hz), 6.93 (2H, d, J=8.7 Hz), 5.67–5.50 (1H, m), 5.36–5.33 (1H, m), 5.20–5.14 (1H, m), 4.93–4.87 (2H, m), 3.79 (3H, s), 2.68–2.59 (1H, m), 2.24–2.09 (2H, m), 1.97–1.55 (1H, bm), 1.11–1.00 (1H, m), 0.95 (3H, d, J=6.5 Hz) and 0.88 (3H, d, J=6.5 Hz). ¹³C-NMR; δ (MeOD), 176.2, 172.4, 171.9, 161.4, 136.0, 130.2, 129.4, 117.4, 115.2, 79.7, 58.2, 55.8, 48.3, 47.3, 41.5, 36.0, 33.4, 33.3, 26.7, 24.6, 24.5 and 21.7.

Diastereoisomer B

¹H-NMR; δ (MeOD), 8.96 (1H, d, J=6.7 Hz), 7.29 (2H, d, J=8.7 Hz), 6.93 (2H, d, J=8.7 Hz), 5.77–5.61 (1H, m), 5.32 (1H, s), 5.20–5.15 (1H, m), 5.09–4.97 (2H, m), 3.80 (3H, s), 2.64 (1H, dt, J=3.3, 11.4, 13.5 Hz), 2.43–2.16 (3H, m), 1.9H.49 (9H, bm), 1.42–1.29 (1H, m), 1.05 (1H, ddd, J=3.3, 10.1, 13.2 Hz) and 0.81 (6H, d, J=6.5 Hz). ₋₁₃C-NMR; δ (MeOD), 176.3, 172.5, 172.0, 161.4, 136.4, 130.2, 129.0, 117.5, 115.2, 79.8, 58.2, 55.8, 48.4, 47.4, 41.3, 36.1, 33.4, 27.1, 24.5, 24.3 and 21.6.

EXAMPLE 48

2-(3S-Hydroxycarbamoyl-2R-isobutyl-hex-5-enoylamino)-2-(thien-2-yl)ethanoic acid cyclopentyl ester.

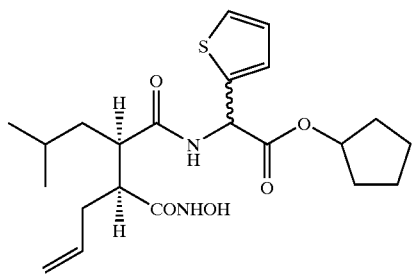

The above compound was prepared using methods similar to those described in example 41, using thien-2-ylglycine cyclopentyl ester.

Diastereoisomer A

¹H-NMR; δ (MeOD), 7.41 (1H, dd, J=5.1, 1.2 Hz), 7.12 (1H, d, J=3.5 Hz), 7.01 (1H, dd, J=5.1, 3.5 Hz), 5.72 (1H, s), 5.69–5.52 (1H, m), 5.26–5.18 (1H, m), 5.00–4.89 (2H, m), 2.70–2.59 (1H, m), 2.28–2.13 (2H, m) 2.09–1.50 (1H, m), 1.05 (1H, ddd, J=13.8, 11.0, 2.9 Hz), 0.93 (3H, d, J=6.4 Hz) and 0.87 (3H, d, J=6.5 Hz). ¹³C-NMR; δ (MeOD), 176.5, 172.7, 171.1, 139.5, 136.4, 128.4, 128.3, 127.7, 117.9, 80.7, 54.1, 48.7, 47.7, 41.9, 36.5, 33.8, 33.7, 27.2, 25.1, 25.0, 24.9, and 22.1.

Diastereoisomer B

¹H-NMR; δ (MeOD), 7.42 (1H, dd, J=5.0, 0.7 Hz), 7.10 (1H, d, J=3.6 Hz), 7.01 (1H, dd, J=5.0, 3.6 Hz), 5.79–5.59 (2H, m), 5.28–5.19 (1H, m), 5.10–4.94 (2H, m), 2.71–2.59 (1H, m), 2.36–2.16 (3H, m), 1.97–1.34 (1 OH, m), 1.13–1.00 (1H, m), 0.86 (3H, d, J=6.2 Hz) and 0.84 (3H, d, J=6.3 Hz). ¹³C-NMR; δ (MeOD), 176.7, 172.8, 171.2, 139.3, 136.7, 128.3, 128.2, 127.6, 117.9, 80.7, 54.2, 48.8, 47.8, 41.7, 36.4, 33.8, 27.5, 25.1, 25.0, 24.8 and 22-1.

EXAMPLE 49

2-(3S-Hydroxycarbamoyl-2R-isobutyl-hex-5-enoylamino)-2-(thien-3-yl)ethanoic acid cyclopentyl ester.

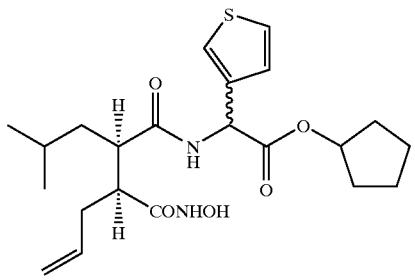

The above compound was prepared using methods similar to those described in example 41, using thien-3-ylglycine cyclopentyl ester.

Diastereoisomer A

¹H-NMR; δ (MeOD), 7.48–7.42 (2H, m), 7.13 (1H, dd, J=4.2, 2.0 Hz), 5.69–5.52 (2H, m), 5.21–5.16 (1H, m), 4.98–4.90 (2H, m), 2.71–2.59 (1H, m), 2.28–2.11 (2H, m), 2.00–1.50 (1H, m), 1.12–0.98 (1H, m), 0.94 (3H, d, J=6.4 Hz) and 0.88 (3H, d, J=6.5 Hz). ¹³C-NMR; δ (MeOD), 176.6, 172.8, 171.8, 137.8, 136.4, 128.3, 128.0, 125.2, 117.9, 80.3, 54.6, 41.9, 36.5, 33.8, 33.8, 27.1, 25.0, 24.9 and 22.1.

Diastereoisomer B

¹H-NMR; δ (MeOD), 7.45 (1H, dd, J=4.9, MHz), 7.43–7.40 (1H, m), 7.12 (1H, dd, J=5.0, 1.3 Hz), 5.68 (1H, ddt, J=17.0, 10.1, 6.8 Hz), 5.53 (1H, s), 5.23–5.17 (1H, 5.10–4.96 (2H, m), 2.70–2.60 (1H, m), 2.41–2.16 (3H, m), 1.94–1.49 (9H, m), 1.44–1.29 (1H, m), 1.05 (1H, ddd, J=12.9, 10.3, 3.3 Hz), 0.84 (3H, d, J=6.5 Hz) and 0.83 (3H, d, J=6.5 Hz).

BIOLOGICAL EXAMPLE

The compounds of examples 1–5 were tested in the following cell proliferation assay, to determine their respective capacities to inhibit proliferation of the cell types in question.

Two human cell lines namely a histiocytic lymphoma (U937) and a melanoma (RPMI-7951) were seeded into 30 mm² tissue culture wells, in the appropriate culture medium supplemented with 10% fetal calf serum at a density of 250 cells/mm². Six hours later the test compounds were added in the same culture medium to the cells to give a final concentration of 6 μM. Control wells contained cells supplemented with the same culture medium containing the equivalent amount of drug vehicle, which in this case was DMSO at a final concentration of 0.08%. After 72 hours in culture the cells were pulsed for 3 hours with [methyl-³[H] Thymidine] (2 μCi/ml) and then harvested onto filter mats and DNA associated radioactivity counted. Results are expressed as percentage of control ³[H] Thymidine incorporation (n=6±1 stdv). The results obtained are set out in the following Table 1.

| Activities | | |
|---|---|---|
| Example | U937 | RPMI |
| 1 | 7 | 40 |
| 2 | 7 | 37 |
| 3 | 2.5 | 27 |
| 4 | 93 | Not tested |
| 5 | 19 | 82 |

Further examples were tested in the U937 assay described above at 6 μM and the results, expressed as percentage of control $^3$[H] Thymidine incorporation (n=6±1 stdv), are set out in the following Table 2.

| Example | U937 |
|---|---|
| 6 | 18 |
| 7 | 0 |
| 8 | 1 |
| 9 | 8 |
| 10 | 1 |
| 11 | 0 |
| 12 | 10 |
| 13 | 4 |
| 14 | 33 |
| 15 | 19 |
| 16 | 2 |
| 17 | 0 |
| 18 | 54 |
| 19 | Not tested |
| 20 | 0 |
| 21 | 1 |
| 22 | 51 |
| 23 | 36 |
| 24 | 50 |
| 25 | 34 |
| 26 | 0 |
| 27 | 0 |
| 28 | 0 |
| 29 | 49 |
| 30 | 6 |
| 31 | 7 |
| 32 | 0 |
| 33 | Not tested |
| 34 | 3 |
| 35 | 14 |
| 36 | 51 |
| 37 | 0 |
| 38 | 37 |
| 39 | 26 |
| 40 | 0 |
| 41 | 0 |
| 42 | 0 |
| 43 | Not tested |

For comparison, the activity in the above U937 assay of the known cytotoxic agent 5-fluorouracil (5-FU) at 6 μM was found to be 50% of that observed with the vehicle alone.

The compounds of examples 44–49 was tested in the following cell proliferation assay, to determine their ability to inhibit proliferation of the cell type in question.

A human cell line, namely a histiocytic lymphoma (U937), was seeded into 30MM$^2$ tissue culture wells, in the appropriate culture medium supplemented with 10% fetal calf serum at a density of 250 cellS/MM$^2$. Six hours later the test compounds were added in the same culture medium to the cells to give a final concentration of 6 μM. Control wells contained cells supplemented with the same culture medium containing the equivalent amount of drug vehicle, which in this case was DMSO at a final concentration of 0.08%. After 72 hours in culture the cells were pulsed for 3 hours with [methyl-$^3$[H] Thymidine] (2 μCi/ml) and then harvested onto filter mats and DNA associated radioactivity counted. Results were expressed as percentage of control $^3$[H] Thymidine incorporation (n=6±1 stdv). Inhibition of proliferation was observed with all test compounds.

Having described preferred embodiments of the invention, it is to be understood that the invention is not limited to those precise embodiments, and that various changes and modifications may be effected therein by one skilled in the art without departing from the scope or spirit of the invention defined in the appended claims.

What is claimed is:

1. A compound selected from the group consisting of:

2(R or S)-[2R-(S-Hydroxy-hydroxycarbamoyl-methyl)-4-methyl-pentanoylamino]-2-phenyl-ethanoic acid cyclopentyl ester, 2(R or S)-(3S-Hydroxycarbamoyl-2R-isobutyl-hex-5-enoylamino)-2-phenylethanoic acid isopropyl ester, 2(R or S)-[2R-(S-Hydroxycarbamoyl-methoxy-methyl)-4-methyl-pentanoylamino]-2-phenylethanoic acid cyclopentyl ester, 2(R or S)-(3S-Hydroxycarbamoyl-2R-isobutyl-hex-5-enoylamino)-2-(4-methoxyphenyl)ethanoic acid cyclopentyl ester, 2(R or S)-(3S-Hydroxycarbamoyl-2R-isobutyl-hex-5-enoylamino)-2-(thien-2-yl)ethanoic acid cyclopentyl ester, 2(R or S)-(3S-Hydroxycarbamoyl-2R-isobutyl-hex-5-enoylamino)-2-(thien-3-yl)ethanoic acid cyclopentyl ester, and pharmaceutically or veterinarily acceptable salts thereof.

2. The compound of claim 1, wherein said compound is 2(R or S)-[2R-(S-Hydroxy-hydroxycarbamoyl-methyl)-4-methyl-pentanoylamino]-2-phenyl-ethanoic acid cyclopentyl ester.

3. The compound of claim 2, wherein the compound is 2(S)-[2R-(S-Hydroxy-hydroxycarbamoyl-methyl)-4-methyl-pentanoylamino]-2-phenyl-ethanoic acid cyclopentyl ester.

4. A method of treating a subject suffering from a proliferative cell growth disorder characterized by hyper-proliferative cell growth comprising administering to the subject a composition comprising a pharmaceutically or veterinarily acceptable carrier in combination with the compound of claim 3 or a pharmaceutically acceptable salt, hydrate or solvate thereof for a time and under conditions effective to inhibit growth and proliferation of said cells.

5. A pharmaceutical or veterinary composition useful for treating a cell-proliferative growth disorder characterized by hyper-proliferative cell growth, comprising a compound of claim 3 in combination with a pharmaceutically or veterinarily acceptable carrier or diluent.

6. The compound of claim 2, wherein said compound is a diastereoisomer of 2-[2R-(S-hydroxy-hydroxycarbamoyl-methyl)-4-methyl-pentanoylamino]-2-phenyl-ethanoic acid cyclopentyl ester, which is characterized by nuclear magnetic resonance spectral data as set forth below:

$^1$H-NMR: δ (CD$_3$OD), 7.29–7.4 (5H, m), 5.43 (1H, s), 5.14–5.2 (1H, m), 4.02 (1H, d, J=6.9 Hz), 2.85–2.94 (1H, m), 1.34–1.91 (10H, bm), 1.14–1.25 (1H, m) and 0.86 (6H, dd, J=6.5, 11.5 Hz);

$^{13}$C-NMR: δ (CD$_3$OD), 22.1, 23.7, 24.4, 24.5, 26.8, 33.3, 33.3 39.1, 49.2, 58.5, 73.2, 80.0, 128.6, 129.4, 129.8, 137.8, 171.4, 171.8, 175.6;

or a pharmaceutically acceptable salt, hydrate or solvate thereof.

7. A pharmaceutical or veterinary composition useful for treating a proliferative cell growth disorder characterized by hyper-proliferative cell growth, comprising the compound of claim 6 in combination with a pharmaceutically or veterinarily acceptable carrier or diluent.

8. An anti-proliferative composition comprising a compound of claim 6 or a pharmaceutically or veterinarily acceptable salt thereof in combination with a pharmaceutically or veterinarily acceptable carrier or diluent.

9. A method of treating a subject suffering from a hyper-proliferative cell growth disorder comprising administering to the subject a composition comprising a compound of claim 6 or a pharmaceutically acceptable salt, hydrate or solvate thereof in combination with a pharmaceutically or veterinarily acceptable carrier or diluent for a time and under conditions effective to inhibit growth and proliferation of said cells.

10. The compound of claim 1, wherein said compound is 2(R or S)-[2R-(S-hydroxycarbamol-methoxy-methyl)-4-methyl-pentanoylamino]-2-phenylethanoic acid cyclopentyl ester.

11. The compound of claim 10, wherein the compound is 2(S)-[2R-(S-Hydroxycarbamoyl-methoxy-methyl)-4-methyl-pentanoylamino]-2-phenylethanoic acid cyclopentyl ester.

12. A pharmaceutical or veterinary composition useful for treating a cell-proliferative growth disorder characterized by hyper-proliferative cell growth, comprising a compound of claim 11 in combination with a pharmaceutically or veterinarily acceptable carrier or diluent.

13. A method of treating a subject suffering from a proliferative cell growth disorder characterized by hyper-proliferative cell growth comprising administering to the subject a composition comprising a pharmaceutically or veterinarily acceptable carrier in combination with of the compound of claim 11 or a pharmaceutically acceptable salt, hydrate or solvate thereof for a time and under conditions effective to inhibit growth and proliferation of said cells.

14. The compound of claim 1, wherein said compound is 2(R or S)-(3S-Hydroxycarbamoyl-2R-isobutyl-hex-5-enoylamino)-2-phenylethanoic acid isopropyl ester.

15. The compound of claim 14, wherein the compound is 2(S)-(3S-Hydroxycarbamoyl-2R-isobutyl-hex-5-enoylamino)-2-phenylethanoic acid isopropyl ester.

16. A pharmaceutical or veterinary composition useful for treating a cell-proliferative growth disorder characterized by hyper-proliferative cell growth, comprising a compound of claim 15 in combination with a pharmaceutically or veterinarily acceptable carrier or diluent.

17. A method of treating a subject suffering from a proliferative cell growth disorder characterized by hyper-proliferative cell growth comprising administering to the subject a composition comprising a pharmaceutically or veterinarily acceptable carrier in combination with the compound of claim 15 or a pharmaceutically acceptable salt, hydrate or solvate thereof for a time and under conditions effective to inhibit growth and proliferation of said cells.

18. The compound of claim 1, wherein said compound is 2(R or S)-(3S-Hydroxycarbamoyl-2R-isobutyl-hex-5-enoylamino)-2-(4-methoxyphenyl)ethanoic acid cyclopentyl ester.

19. The compound of claim 18, wherein the compound is 2(S)-(3S-Hydroxycarbamoyl-2R-isobutyl-hex-5-enoylamino)-2-(4-methoxyphenyl)ethanoic acid cyclopentyl ester.

20. A pharmaceutical or veterinary composition useful for treating a cell-proliferative growth disorder characterized by hyper-proliferative cell growth, comprising a compound of claim 19 in combination with a pharmaceutically or veterinarily acceptable carrier or diluent.

21. A method of treating a subject suffering from a proliferative cell growth disorder characterized by hyper-proliferative cell growth comprising administering to the subject a composition comprising a pharmaceutically or veterinarily acceptable carrier in combination with the compound of claim 19 or a pharmaceutically acceptable salt, hydrate or solvate thereof for a time and under conditions effective to inhibit growth and proliferation of said cells.

22. The compound of claim 1, wherein the compound is 2(R or S)-(3S-Hydroxycarbamoyl-2R-isobutyl-hex-5-enoylamino)-2-(thien-2-yl)ethanoic acid cyclopentyl ester.

23. The compound of claim 22, wherein the compound is 2(S)-(3S-Hydroxycarbamoyl-2R-isobutyl-hex-5-enoylamino)-2-(thien-2-yl)ethanoic acid cyclopentyl ester.

24. A pharmaceutical or veterinary composition useful for treating a cell-proliferative growth disorder characterized by hyper-proliferative cell growth, comprising a compound of claim 23 in combination with a pharmaceutically or veterinarily acceptable carrier or diluent.

25. A method of treating a subject suffering from a proliferative cell growth disorder characterized by hyper-proliferative cell growth comprising administering to the subject a composition comprising a pharmaceutically or veterinarily acceptable carrier in combination with the compound of claim 23 or a pharmaceutically acceptable salt, hydrate or solvate thereof for a time and under conditions effective to inhibit growth and proliferation of said cells.

26. The compound of claim 1, wherein the compound is 2(R or S)-(3S-Hydroxycarbamoyl-2R-isobutyl-hex-5-enoylamino)-2-(thien-3-yl) ethanoic acid cyclopentyl ester.

27. The compound of claim 26, wherein the compound is 2(S)-(3S-Hydroxycarbamoyl-2R-isobutyl-hex-5-enoylamino)-2-(thien-3-yl)ethanoic acid cyclopentyl ester.

28. A pharmaceutical or veterinary composition useful for treating a cell-proliferative growth disorder characterized by hyper-proliferative cell growth, comprising a compound of claim 27 in combination with a pharmaceutically or veterinarily acceptable carrier or diluent.

29. A method of treating a subject suffering from a proliferative cell growth disorder characterized by hyper-proliferative cell growth comprising administering to the subject a composition comprising a pharmaceutically or veterinarily acceptable carrier in combination with the compound of claim 27 or a pharmaceutically acceptable salt, hydrate or solvate thereof for a time and under conditions effective to inhibit growth and proliferation of said cells.

30. A pharmaceutical or veterinary composition useful for treating a cell-proliferative growth disorder characterized by hyper-proliferative cell growth, comprising a compound of claim 1 in combination with a pharmaceutically or veterinarily acceptable carrier or diluent.

31. A method of treating a subject suffering from a proliferative cell growth disorder characterized by hyper-proliferative cell growth comprising administering to the subject a composition comprising a pharmaceutically or veterinarily acceptable carrier in combination with the compound of claim 1 or a pharmaceutically acceptable salt, hydrate or solvate thereof for a time and under conditions effective to inhibit growth and proliferation of said cells.

32. The method of claims 31, 4, 17, 13, 21, 25, or 29, wherein the disorder is selected from the group consisting of lymphoma, leukemia, myeloma, adenocarcinoma, carcinoma, mesothelioma, teratocarcinoma, choriocarcinoma, small cell carcinoma, large cell carcinoma, melanoma, retinoblastoma, fibrosarcoma, leiomyosarcoma, glioblastoma and endothelioma.

* * * * *